(12) United States Patent
Campbell et al.

(10) Patent No.: US 10,570,156 B2
(45) Date of Patent: *Feb. 25, 2020

(54) SUBSTITUTED IMIDAZO[1,2-A]PYRIDINES AS PDE-10 INHIBITORS

(71) Applicant: SUNOVION PHARMACEUTICALS INC., Marlborough, MA (US)

(72) Inventors: John Emmerson Campbell, Cambridge, MA (US); Philip Wendell Jones, Danvers, MA (US); Michael Charles Hewitt, Somerville, MA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,044

(22) Filed: Nov. 20, 2017

(65) Prior Publication Data
US 2018/0072759 A1    Mar. 15, 2018

Related U.S. Application Data

(60) Continuation of application No. 14/884,397, filed on Oct. 15, 2015, now Pat. No. 9,856,274, which is a division of application No. 14/298,691, filed on Jun. 6, 2014, now Pat. No. 9,249,162, which is a division of application No. 13/347,541, filed on Jan. 10, 2012, now Pat. No. 8,765,760.

(60) Provisional application No. 61/431,769, filed on Jan. 11, 2011.

(51) Int. Cl.
| | | |
|---|---|---|
| *A61K 31/437* | (2006.01) |
| *C07D 471/04* | (2006.01) |
| *C07D 519/00* | (2006.01) |
| *A61K 45/06* | (2006.01) |
| *C07D 487/04* | (2006.01) |
| *A61K 31/4375* | (2006.01) |
| *A61K 31/4745* | (2006.01) |
| *A61K 31/4985* | (2006.01) |
| *A61K 31/519* | (2006.01) |
| *A61K 31/5383* | (2006.01) |

(52) U.S. Cl.
CPC ........ *C07D 519/00* (2013.01); *A61K 31/4375* (2013.01); *A61K 31/4745* (2013.01); *A61K 31/4985* (2013.01); *A61K 31/519* (2013.01); *A61K 31/5383* (2013.01); *A61K 45/06* (2013.01); *C07D 471/04* (2013.01); *C07D 487/04* (2013.01)

(58) Field of Classification Search
CPC .................. A61K 31/437; C07D 471/04
USPC ........................ 514/300; 546/121
See application file for complete search history.

(56) References Cited

U.S. PATENT DOCUMENTS

| | | |
|---|---|---|
| 3,897,432 A | 7/1975 | Shen et al. |
| 6,355,460 B1 | 3/2002 | Clark et al. |
| 8,067,612 B2 | 11/2011 | Krull et al. |
| 2003/0191320 A1 | 10/2003 | Eliu et al. |
| 2004/0006011 A1 | 1/2004 | Gour et al. |
| 2007/0112048 A1 | 5/2007 | Bavari et al. |
| 2010/0016303 A1 | 1/2010 | Ritzen et al. |
| 2010/0076040 A1 | 3/2010 | Krull |
| 2011/0284799 A1 | 11/2011 | Stoessel et al. |
| 2012/0129836 A1 | 5/2012 | Kehler et al. |
| 2012/0178748 A1* | 7/2012 | Campbell .............. A61K 45/06 514/230.2 |
| 2014/0288062 A1 | 9/2014 | Campbell et al. |

FOREIGN PATENT DOCUMENTS

| | | |
|---|---|---|
| EP | 0334289 A1 | 9/1989 |
| GB | 1356763 A | 6/1974 |
| JP | 54039093 B2 | 3/2014 |
| WO | 8705021 A1 | 8/1987 |
| WO | 0023449 A1 | 4/2000 |
| WO | 2006084184 A2 | 8/2006 |
| WO | WO-2008/051808 A2 | 5/2008 |
| WO | 2009039246 A2 | 3/2009 |
| WO | WO-2009/070583 A1 | 6/2009 |
| WO | WO-2009/152825 A1 | 12/2009 |
| WO | WO-2009/158393 A1 | 12/2009 |
| WO | WO-2009/158467 A2 | 12/2009 |
| WO | WO-2009/158473 A1 | 12/2009 |
| WO | WO-2010/006130 A2 | 1/2010 |
| WO | WO-2010/017236 A1 | 2/2010 |
| WO | WO-2010/027097 A1 | 3/2010 |
| WO | WO-2010/054253 A1 | 5/2010 |
| WO | WO-2010/054260 A1 | 5/2010 |
| WO | WO-2010/057121 A1 | 5/2010 |
| WO | WO-2010/057126 A1 | 5/2010 |
| WO | WO-2010/062559 A1 | 6/2010 |
| WO | WO-2010/083625 A1 | 7/2010 |
| WO | 2010086089 A1 | 8/2010 |
| WO | WO-2011/072694 A1 | 6/2011 |
| WO | WO-2011/072695 A1 | 6/2011 |
| WO | WO-2011/072696 A1 | 6/2011 |

(Continued)

OTHER PUBLICATIONS

Jordan, V. C. Nature Reviews: Drug Discovery, Feb. 2003, 205.*

(Continued)

*Primary Examiner* — Douglas M Willis

(57) ABSTRACT

Provided herein are cyclic nucleotide phosphodiesterase inhibitors of Formula (I) of claim 1, and pharmaceutical compositions thereof, useful for the treatment of, for example, central nervous system and metabolic diseases and disorder.

18 Claims, No Drawings

(56) References Cited

FOREIGN PATENT DOCUMENTS

| WO | WO-2011/072697 A1 | 6/2011 |
|----|-------------------|--------|
| WO | WO-2011/150156 A2 | 12/2011 |
| WO | 2012/065612 A1 | 5/2012 |
| WO | 2012065612 A1 | 5/2012 |
| WO | 2012096929 A2 | 7/2012 |

OTHER PUBLICATIONS

Hackam, et al. JAMA, 296(14), 2006, 1731-1732.*
The English translation of the Japanese Office Action, dated Jan. 24, 2017, in the related Japanese Application No. 2016-028453.
RN 300814-78-2, Database Registry[Online], Nov. 2, 2000, Retrived from STN.
RN 300571.85-1, Database Registry[Online], Oct. 31, 2000, Retrived from STN.
RN 1223523-16-7, Database Registry[Online], May 14, 2010, Retrived from STN.
RN 1223366-42-4, Database Registry[Online], May 14, 2010, Retrived from STN.
RN 950451-93-1, Database Registry[Online], Oct. 12, 2007, Retrived from STN.
RN 924412-49-7, Database Registry[Online], Mar. 2, 2007, Retrived from STN.
RN 893707-76-1, Database Registry[Online], Jul. 17, 2006, Retrived from STN.
RN 874778-18-4, Database Registry[Online], Feb. 21, 2006, Retrived from STN.
RN 585556-61-2, Database Registry[Online], Sep. 15, 2003, Retrived from STN.
RN 521320-13-8, Database Registry[Online], May 28, 2003, Retrived from STN.
RN 521319-93-7, Database Registry[Online], May 28, 2003, Retrived from STN.
The extended European search report, dated May 24, 2017, in the related European Application No. 17160357.4.
Database Caplus [Online], Chemical Abstracts Service, Columbus, Ohio, US; 1963, Levin, Ya. et al., "Condensed heterocycles II. Condensation of 5-alkyl-3-amino-1,2,4-triazoles with acetoacetic ester," XP002724419, retrieved from STN, Database accession No. 1963:469152, abstract; compounds CRN 101609-97-6.
Chappie, J.S. et al., PDE10A inhibitors: an assesment of the current CNS drug discovery landscape. Current Opihton on Drud Development, 12(4):458-467 (2009).
Chen, Q.P. and Deady, L.W., Synthesis of some benzo[b][1,6]naphthyridines and benzo[b][1,7]naphthyridines, Australian Journal of Chemistry, 46:987-993 (1993).
CID: 20880401, PubChem, Open Chemistry Database (2007), 3 pages, cited in the First Office Action issued by SIPO in CN Application No. 201280011263.1, dated Jan. 19, 2015, Chemistry Invention Examination Department, Jiangsu Patent Examination Cooperation Center.
CID: 20880403, PubChem, Open Chemistry Database (2007), 3 pages, cited in the First Office Action issued by SIPO in CN Application No. 201280011263.1, dated Jan. 19, 2015, Chemistry Invention Examination Department, Jiangsu Patent Examination Cooperation Center.
CID: 20880414, PubChem, Open Chemistry Database (2007), 3 pages, cited in the First Office Action issued by SIPO in CN Application No. 201280011263.1, dated Jan. 19, 2015, Chemistry Invention Examination Department, Jiangsu Patent Examination Cooperation Center.
CID: 20880420, PubChem, Open Chemistry Database (2007), 3 pages, cited in the First Office Action issued by SIPO in CN Application No. 201280011263.1, dated Jan. 19, 2015, Chemistry Invention Examination Department, Jiangsu Patent Examination Cooperation Center.
CID: 20927916, PubChem, Open Chemistry Database (2007), 3 pages, cited in the First Office Action issued by SIPO in CN Application No. 201280011263.1, dated Jan. 19, 2015, Chemistry Invention Examination Department, Jiangsu Patent Examination Cooperation Center.
CID: 46280257, PubChem, Open Chemistry Database (2010), 3 pages, cited in the First Office Action issued by SIPO in CN Application No. 201280011263.1, dated Jan. 19, 2015, Chemistry Invention Examination Department, Jiangsu Patent Examination Cooperation Center.
CID: 854795 PubChem, Open Chemistry Database (2005), 3 pages cited in the First Office Action issued by SIPO in CN Application No. 201280011263.1, dated Jan. 19, 2015, Chemistry Invention Examination Department, Jiangsu Patent Examination Cooperation Center.
D'Amico, J. J. and Campbell, R. H., 2,2'-Thiobis(benzoxazole) and 3-(2-Benzoxazolyl)-2-benzoazolinethione, The Journal of Organic Chemistry, vol. 32(10):3196-3197 (1967).
Gellibert, F. et al., Identification of 1,5-napththyridine derivatives as a novel series of potent and selective TGF-beta type I receptor inhibitors, Journal of Medicinal Chemistry, 47(18):4494-4506 (2004).
Grauer, S.M. et al., Phosphodiesterase 10A inhibitor activity in preclinical models of the postive, cognitive, and negative symptoms of schizophrenia, Journal of Pharmacology and Experimental Therapeutics, 331(2):574-590 (2009).
Kaizerman, J.A. et al., DNA binding ligands targeting drug-resistant bacteria: structure, activity, and pharmacology, Journal of Medicinal Chemistry, 46(18):3914-3929 (2003).
Kehler, J. et al., Patented PDE 10A inhibitors: novel compounds since 2007, Expert Opinion on Therpeutic Patents, 19(12):1715-1725 (2009).
Kehler, J. et al., The Potential Therapeutic Use of Phosphodiesterase 10 Inhibitors, Expert Opinion on Therapeutic Patents, 17(2):147-158 (2007).
Kitagawa, H. et al., Phenylimidazole derivatives of 4-pyridone as dual inhibitors of bacterial enoyl-acyl carrier protein reductases Fabi and Fabk, Journal of Medicinal Chemistry, 50(19):4710-4720 (2007).
Leonard, K. et al., Non-peptidic alpha(v)beta3 antagonist containing indol-1-yl propionic acids, Bioorganic Medicinal Chemistry Letters, 15(10):2679-2684 (2005).
Menniti, F.S. et al., Phosphodiesterase 10A inhibitors: a novel approach to the treatment of the symptoms of schizophrenia, Current Opinion on Investigative Drugs, 8(1):54-59 (2007).
Rai, C. et al., Synthesis of Bisnaphthoxazoles, Canadian Journal of Chemistry, 42:179-181 (1964).
Reiser, A. et al., Fluorescence Aromatic Benzoxazole Derivatives, Journal of the American Chemical Society, 94(7):2414-2421 (1972).
Ried, V. W. and Patschorke, J., Uber a,w-heterocyclisch disubstituierte Paraffine, Justus Liebigs Annalen Der Chemie, 599:44-50 (1956).
RN: 1110986-63-4, ACS, STN Registry Database (2009), 1 page, cited in the First Office Action issued by SIPO in CN Application No. 201280011263.1, dated Jan. 19, 2015, Chemistry Invention Examination Department, Jiangsu Patent Examination Cooperation Center.
RN: 1112330-69-4, ACS, STN Registry Database (2009), 1 page, cited in the First Office Action issued by SIPO in CN Application No. 201280011263.1, dated Jan. 19, 2015, Chemistry Invention Examination Department, Jiangsu Patent Examination Cooperation Center.
Sakamoto, T. et al., Condensed heteroaromatic ring systems. III. Synthesis of naphthyridine derivatives by cyclization of ethynylpyridinecarboxamides, Chemical Pharmaceutical Bulletin, 33(2):626-633 (1985).
Schmidt, C.J. et al., Preclinical characteriation of selective phosphodiesterase 10A inhibitors: a new therapeutic approach to the treatment of schizophrenia, Journal of Pharmacological Experimental Therapies, 325(2):681-690 (2008).
Tamura, Y. et al., 1,3-Dipolar cycloaddition reaction of benzodiazinium and naphthyridinium N-imines with acetylenic esters, Journal of Heterocyclic Chemistry, 12(1):119-122 (1975).
Threlfell, S. et al., Inhibition of phosphodiesterase 10A increases the responsiveness of striatal projection neurons to cortical stimulation, 328(3):785-795 (2009).

(56) References Cited

OTHER PUBLICATIONS

The English translation of the Chinese Office Action, dated Sep. 28, 2018, in the related Chinese Patent Appl. No. 201710186503.6.

* cited by examiner

SUBSTITUTED IMIDAZO[1,2-A]PYRIDINES AS PDE-10 INHIBITORS

I. CROSS-REFERENCE TO RELATED APPLICATION

This application claims priority to and is a continuation of pending U.S. patent application Ser. No. 14/884,397, file Oct. 15, 2015, which in turn claims priority to and is a divisional of U.S. patent application Ser. No. 14/298,691, filed Jun. 6, 2014, and patented as U.S. Pat. No. 9,249,162 on Sep. 25, 2014; which in turn claims priority to and is a divisional of U.S. patent application Ser. No. 13/347,541, filed Jan. 10, 2012, and patented as U.S. Pat. No. 8,765,760 on Jul. 1, 2014, which in turn claims benefit from U.S. Provisional Patent Application Ser. No. 61/431,769 filed Jan. 11, 2011, all of which are hereby incorporated by reference in their entireties.

II. FIELD

Provided herein are heteroaryl compounds useful for treating various disorders or diseases, such as disorders or diseases of the central nervous system and metabolic disorders. Also provided herein are compositions comprising the compounds, and methods of use thereof.

III. BACKGROUND

Central nervous system (CNS) disorders affect a wide range of the population with differing severity. For example, schizophrenia is a psychopathological disorder of unknown origin, which usually appears for the first time in early adulthood and is marked by characteristics, such as, psychotic symptoms, phasic progression and development, and deterioration in social behavior and professional capability. Characteristic psychotic symptoms include disorders of thought content (e.g., multiple, fragmentary, incoherent, implausible or simply delusional contents, or ideas of persecution) and of mentality (e.g., loss of association, flight of imagination, incoherence, or incomprehensibility), as well as disorders of perceptibility (e.g., hallucinations), emotions (e.g., superficial or inadequate emotions), self-perceptions, intentions, impulses, and inter-human relationships, and psychomotoric disorders (e.g., catatonia). Other symptoms are also associated with this disorder. See, e.g., *Diagnostic and Statistical Manual of Mental Disorders*, 4$^{th}$ Ed., American Psychiatric Association (1997) (DSM-IV™).

Schizophrenia can be classified into various subgroups. For example, the paranoid type is characterized by delusions and hallucinations and absence of thought disorder, disorganized behavior, and affective flattening. The disorganized type, also named hebephrenic schizophrenia, is characterized by the presence of both thought disorder and affective flattening. The catatonic type is characterized by prominent psychomotor disturbances, including symptoms of catatonic stupor and waxy flexibility. In the undifferentiated type, psychotic symptoms are present but the criteria for paranoid, disorganized, or catatonic types have not been met.

The symptoms of schizophrenia normally manifest themselves in three broad categories, i.e., positive, negative and cognitive symptoms. Positive symptoms are those that represent an excess of normal experiences, such as hallucinations, disorganized speech, and delusions. Negative symptoms are those where the patient suffers from a lack of normal experiences, such as anhedonia, lack of motivation, inability to experience pleasure, and lack of social interaction. The cognitive symptoms relate to cognitive impairment in schizophrenics, such as lack of sustained attention, impairment of memory, and deficits in decision making. The current anti-psychotics are somewhat effective in treating the positive symptoms but are less effective in treating the negative or cognitive symptoms. For instance, the current typical or atypical anti-psychotics do not address cognitive or negative symptoms of schizophrenia, and only treat the positive symptoms in approximately 40% of patients.

Cognitive impairments include a decline in cognitive functions or cognitive domains, e.g., working memory, attention and vigilance, verbal learning and memory, visual learning and memory, reasoning and problem solving, e.g., executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts, difficulties in integrating thoughts, feelings and behavior, or difficulties in extinction of irrelevant thoughts.

Agitation is a well-recognized behavioral disorder with a range of symptoms, including hostility, extreme excitement, poor impulse control, tension, and uncooperativeness. Agitation is common in the elderly and often associated with dementia such as those caused by Alzheimer's disease, Parkinson's disease, and Huntington's disease, and by diseases that affect blood vessels, such as stroke or multi-infarct dementia, which is caused by multiple strokes in the brain. An estimated five percent of people aged 65 and older and up to 20 percent of those aged 80 and older are affected by dementia. Of these sufferers, nearly half exhibit behavioral disturbances, such as agitation, wandering, and violent outbursts. Agitated behaviors can also be manifested in cognitively intact elderly people and by those with psychiatric disorders other than dementia.

Dementia is characterized by several cognitive impairments including significant memory deficit and can stand alone, or be an underlying characteristic feature of a variety of diseases, including but not limited to, Alzheimer's disease, Parkinson's disease, Huntington's disease, and multiple sclerosis.

Thus, there remains a great need for effective treatments of various CNS disorders.

Cyclic nucleotide phosphodiesterases (PDEs) are a super family of enzymes encoded by twenty-one genes, and are subdivided into eleven known families based on structure and function. PDEs are modular enzymes having a catalytic domain in the C-terminal portion of the protein and regulatory elements in the N-terminal portion. PDEs hydrolyze the phosphodiester bond of cyclic nucleotides, e.g., cyclic adenosine monophosphate (cAMP) and cyclic guanosine monophosphate (cGMP), converting them into the corresponding monophosphates. cAMP and cGMP function as intracellular second messengers regulating a wide range of intracellular processes. For instance, in neurons cAMP and cGMP activate cyclic-nucleotide-dependent kinases and the subsequent phosphorylation of proteins involved in acute regulation of synaptic transmission and in neuronal differentiation and survival. PDEs are therefore important regulators of a wide variety of physiological processes. PDEs are expressed differentially throughout the organism and cyclic nucleotide signaling is highly compartmentalized within individual cells. Thus, different PDE isozymes can serve distinct physiological functions. Compounds that can selectively inhibit distinct PDE families or isozymes may offer additional therapeutic benefits, fewer side effects, or both.

PDE-10 was first reported in 1999 (Soderling et al., *Proc. Natl. Acad. Sci.*, 1999, 96, 7071-76; Loughney et al., *Gene*, 1999, 234, 109-17; Fujishige et al., *J. Biol. Chem.*, 1999, 274, 18438-45). Homology screening revealed mouse PDE-10A as the first member of the PDE-10 family of enzymes. The human PDE-10 sequence is highly homologous to both the rat and mouse PDE-10 enzymes. The PDE-10 family of enzymes has a lower degree of sequence homology as compared to previously identified PDE families. PDE-10 can hydrolyze both cAMP ($K_m$=0.26 µM) and cGMP ($K_m$=7.2 µM), and has a five-fold greater $V_{max}$ for cGMP than for cAMP.

PDE-10A is primarily expressed in the brain, also found in testes. PDE-10A mRNA and protein are abundant in brain tissues, and are mainly detected at high levels in the medium spiny neurons (MSN) of the striatum, a distribution conserved across mammalian species. The striatal MSNs provide input to the basal ganglia circuit, affecting action selection and execution, and suppressing undesired responses to sensory stimuli. PDE-10A has become an emerging target for the development of new anti-psychotics. Inhibitors of PDE-10A have been shown to increase cAMP and cGMP levels in striatal tissue and have demonstrated efficacy against not only positive but also negative and cognitive symptoms in animal models of schizophrenia. PDE-10A is also useful in treating metabolic disorders, such as diabetes, obesity, and metabolic syndrome.

Citation of any references in this Section of the application is not to be construed as an admission that such reference is prior art to the present application.

IV. SUMMARY

Provided herein are compounds of formula (I), or pharmaceutically acceptable salts or stereoisomers thereof:

A-L-B      (I), wherein A, L, and B are defined herein elsewhere. The compounds are useful for treating various diseases or disorders, such as CNS disorders and metabolic disorders.

Also provided herein are compositions and dosage forms comprising, a compound provided herein, and one or more pharmaceutically acceptable excipient(s). Compositions and dosage forms provided herein may further comprise one or more additional active ingredients.

Also provided herein are methods for the treatment, prevention, and/or management of various disorders, such as a CNS disorder or a metabolic disorder, e.g., the treatment, prevention, and/or amelioration of one or more symptoms of a disorder, using the compounds and compositions provided herein. In one embodiment, the disorders provided herein include, but are not limited to, schizophrenia, psychosis, cognitive disorders, mood disorders, attention deficit disorders, and neurodegenerative diseases. In one embodiment, the disorders include, but are not limited to, neurological disorder, schizophrenia, schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia.

In one embodiment, provided herein is a method of treating, preventing, and/or managing schizophrenia or related disorders, including but not limited to, schizoaffective disorder, schizophreniform disorder, paraphrenia, paranoid personality disorder, schizoid personality disorder, and schizotypal personality disorder; a disease having a psychosis component, including but not limited to, Alzheimer's psychosis, Parkinson's psychosis, shared psychotic disorder, and substance-induced psychotic disorder; cognitive impairment, including but not limited to, cognitive impairment associated with schizophrenia, cognitive deficit in Alzheimer's disease, and cognitive deficit in Parkinson's disease; mood disorder, including but not limited to, bipolar disorder; attention deficit disorder, including but not limited to attention deficit hyperactive disorder; neurodegenerative disease, including but not limited to, Huntington's disease; or depression, including but not limited to, major depressive disorder, unipolar depression, and treatment resistant depression. In one embodiment, provided herein is a method of treating, preventing, and/or managing a disorder provided herein elsewhere (e.g., a CNS disorder or a metabolic disorder), in a subject, such as a mammal, e.g., human, rodent (e.g., mice and rats), cat, dog, and non-human primate, among others. In one embodiment, provided herein is a method of treating, preventing, and/or ameliorating one or more symptoms associated with a disorder provided herein elsewhere (e.g., a CNS disorder or a metabolic disorder), in a subject, such as a mammal, e.g., human, rodent (e.g., mice and rats), cat, dog, and non-human primate, among others. In one embodiment, the method comprises contacting a compound provided herein with a PDE enzyme. In one embodiment, the method comprises contacting a compound provided herein with a PDE enzyme expressed in the central nervous system. In one embodiment, the method comprises contacting a compound provided herein with PDE-10A. In one embodiment, the method comprises contacting a cell with a compound provided herein. In an exemplary embodiment, the cell is a brain cell, such as, e.g., a MSN cell, a neuronal cell, or a glial cell.

V. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may be optionally substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{1-6}$ alkyl groups are also referred as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere. In some embodiments, the alkenyl is optionally substituted with one or more halo.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere. In some embodiments, the alkynyl is optionally substituted with one or more halo.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere. In some embodiments, the cycloalkyl is optionally substituted with one or more halo.

As used herein, and unless otherwise specified, the term "heteroalkyl" refers to a stable straight or branched chain, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O and N can be placed at any interior position of the heteroalkyl group. In one embodiment, the heteroatom(s) S and Si can be placed at any position of the heteroalkyl group (e.g., interior or terminal position), including the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms can be consecutive, such as, for example, —CH$_2$—NH—O—CH$_3$ and —CH$_2$—O—Si(CH$_3$)$_3$. In certain embodiments, the heteroalkyl is optionally substituted as described herein elsewhere. In some embodiments, the heteroalkyl is optionally substituted with one or more halo.

As used herein, and unless otherwise specified, the term "alkoxyl" or "alkoxy" refers to a stable straight or branched chain, or cyclic hydrocarbon radical, or combinations thereof, consisting of the stated number of carbon atoms and from one or more, in one embodiment, one to three, O atoms, wherein at least one O atom is at the position where the alkoxyl or alkoxy group is attached to the remainder of the molecule. Examples of alkoxyl include, but are not limited to, —O—CH$_3$, —O—CF$_3$, —O—CH$_2$—CH$_3$, —O—CH$_2$—CH$_2$—CH$_3$, —O—CH—(CH$_3$)$_2$, and —O—CH$_2$—CH$_2$—O—CH$_3$. In one embodiment, the alkoxyl is optionally substituted as described herein elsewhere. In some embodiments, the alkoxyl is optionally substituted with one or more halo.

As used herein, and unless otherwise specified, the term "aminoalkyl" or "alkylamino" refers to a stable straight or branched chain, or cyclic hydrocarbon radical, or combinations thereof, consisting of the stated number of carbon atoms and from one or more, in one embodiment, one to three, N atoms, wherein at least one N atom is at the position where the aminoalkyl or alkylamino group is attached to the remainder of the molecule. Examples of aminoalkyl include, but are not limited to, —NH—CH$_3$, —N(CH$_3$)$_2$, —NH—CH$_2$—CH$_3$, —N(CH$_3$)—CH$_2$—CH$_3$, —NH—CH—(CH$_3$)$_2$, and —NH—CH$_2$—CH$_2$—N(CH$_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. An example of aralkyl includes, but is not limited to, benzyl. In certain embodiments, both alkyl and aryl may be optionally substituted with one or more substituents as described herein elsewhere.

As used herein, and unless otherwise specified, the term "heteroarylalkyl" or "heteroaralkyl" refers to a monovalent alkyl group substituted with heteroaryl. In certain embodiments, both alkyl and heteroaryl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, periinidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocotimarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the term "optionally substituted" is intended to mean that a group, such as an alkyl, alkenyl, alkynyl, cycloalkyl, heteroalkyl, alkoxyl, aminoalkyl, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—$NO_2$), oxo (=O), —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases. In one embodiment, suitable non-toxic acids include, but are not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, prop ionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein, and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., —CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, depression (e.g., major depressive disorder, dysthymia, and bipolar depressive disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder.

As used herein, and unless otherwise specified, the terms "psychosis," "schizophrenia," "obsessive-compulsive disorder," "substance abuse," "anxiety," "eating disorders," "migraine," and other CNS disorders described herein elsewhere are used herein in a manner consistent with their accepted meanings in the art. See, e.g., *Diagnostic and Statistical Manual of Mental Disorders*, 4$^{th}$ Ed., American Psychiatric Association (1997) (DSM-IV™).

As used herein, and unless otherwise specified, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD), dysthymia, and treatment resistant depression. "Major depressive disorder" is used herein interchangeably with "unipolar depression" and "major depression." "Depression" may also include any condition commonly associated with depression, such as all forms of fatigue (e.g., chronic fatigue syndrome) and cognitive deficits.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, The term "pain" includes pain resulting from dysfunction of the nervous system: organic pain states that share clinical features of neuropathic pain and possible common pathophysiology mechanisms, but are not initiated by an identifiable lesion in any part of the nervous system.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the terms "overweight" and "obese" refer to adult persons 18 years or older having a greater than ideal body weight (e.g., greater than ideal body fat) that can be measured by the body mass index (BMI), which is generally correlated with total body fat and the relative risk of suffering from premature death or disability due to diseases as a consequence of the overweight or obese condition. BMI is calculated by weight in kilograms divided by height in meters squared (kg/m$^2$), or alternatively by weight in pounds, multiplied by 703, divided by height in inches squared (lbs×703/in$^2$). Overweight individuals typically have a BMI of between about 25 and about 29, whereas obese individuals typically have a BMI of about 30 or more (see, e.g., National Heart, Lung, and Blood Institute, Clinical Guidelines on the Identification, Evaluation, and Treatment of Overweight and Obesity in Adults, The Evidence Report, Washington, D.C., U.S. Department of Health and Human Services, NIH publication no. 98-4083, 1998). Other means for indicating excess body weight, excess body fat, and obesity include direct measure of body fat and/or waist-to-hip ratio measurements.

As used herein, and unless otherwise specified, the term "metabolic syndrome" is used according to its usual meaning in the art. The American Heart Association characterizes metabolic syndrome as having at least three or more of the following symptoms: 1) elevated waist circumference [>102 cm (40 inches) in men; >88 cm (35 inches) in women]; 2) elevated triglycerides [≥150 mg/dL (>1.695 mmol/L) or drug treatment for elevated triglycerides]; 3) reduced HDL cholesterol [<40 mg/dL (1.036 mmol/L) in men; <50 mg/dL (1.295 mmol/L) in women; or drug treatment for reduced HDL-C]; 4) elevated blood pressure [≥130/85 mmHg or drug treatment for hypertension]; and 5) elevated fasting glucose [≥110 mg/dL or drug treatment for elevated glucose]. According to the World Health Organization, metabolic syndrome includes individuals suffering from diabetes, impaired glucose tolerance, impaired fasting glucose, or insulin resistance plus two or more of the following symptoms: 1) high blood pressure [≥160/90 mmHg]; 2) hyperlipdemia [triglyceride concentration ≥150 mg/dL (1.695 mmol/L) and/or HDL cholesterol <35 mg/dL (0.9 mmol/L) in men and <39 mg/dL (1.0 mmol/L) in women]; 3) central obesity [waist-to-hip ratio of >0.90 for men and >0.85 for women and/or BMI >30 kg/m$^2$]; and 4) microalbuminuria [urinary albumin excretion rate ≥20 μg/min or an albumin-to-creatinine ratio ≥20 mg/kg).

B. Compounds

In one embodiment, provided herein is a compound of formula (I):

A-L-B (I), or a pharmaceutically acceptable salt or stereoisomer thereof, wherein L is —(C(R$^{10}$)$_2$)$_m$—, —CR$^{10}$=CR$^{10}$—,

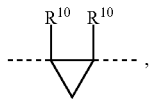

—K—C(R$^{10}$)$_2$—, —C(R$^{10}$)$_2$—K—, or —S—;
K is —NR$^{11}$—, —O—, or —S—;
m is 2 or 3;

A is

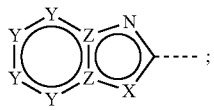

X is (i) CR¹ or N; or (ii) O or NR²;
each Y is independently N or CR³;
each Z is independently N or C;
provided that A contains 1, 2, 3, or 4 nitrogen ring atoms;
B is

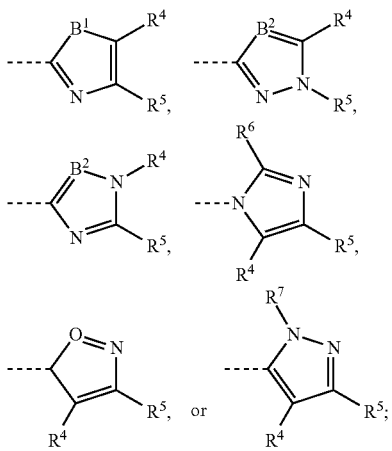

B¹ is O, S, or NR⁸;
B² is CR⁹ or N;
R¹ is hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl;
R² is hydrogen, alkyl, alkenyl, heteroalkyl, cycloalkyl, aryl, heteroaryl, heterocyclyl, carbonyl, or sulfonyl;
each R³ is independently (i) hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl; or (ii) two adjacent occurrences of R³ together with the atoms to which they are attached form an aryl or heteroaryl ring;
R⁴ and R⁵ together with the atoms to which they are attached form a monocyclic or multicyclic aryl, heteroaryl, cycloalkyl, or heterocyclyl ring;
R⁶ is hydrogen, halo, cyano, alkyl, alkenyl, alkoxyl, aminoalkyl, heteroalkyl, cycloalkyl, aralkyl, heteroaralkyl, aryl, heteroaryl, heterocyclyl, amino, amido, carbonyl, thiol, sulfinyl, or sulfonyl;
R⁷ is hydrogen, alkyl, alkenyl, heteroalkyl, cycloalkyl, aryl, heteroaryl, heterocyclyl, carbonyl, or sulfonyl;
R⁸ is hydrogen, alkyl, alkenyl, heteroalkyl, cycloalkyl, aryl, heteroaryl, heterocyclyl, carbonyl, or sulfonyl;
R⁹ is hydrogen, halo, cyano, alkyl, alkenyl, alkoxyl, aminoalkyl, heteroalkyl, cycloalkyl, aralkyl, heteroaralkyl, aryl, heteroaryl, heterocyclyl, amino, amido, carbonyl, thiol, sulfinyl, or sulfonyl;
each R¹⁰ is independently hydrogen, halo, or alkyl; and
each R¹¹ is hydrogen or alkyl.
In one embodiment, L is —(C(R¹⁰)₂)ₘ— or —CR¹⁰=CR¹⁰—. In one embodiment, each R¹⁰ is independently hydrogen or methyl. In one embodiment, R¹⁰ is hydrogen. In one embodiment, at least one R¹⁰ is methyl. In one embodiment, at least two occurrences of R¹⁰ are methyl. In one embodiment, at least one R¹⁰ is methyl and the other one or more R¹⁰ is/are hydrogen. In one embodiment, L is —(CH₂)ₘ—. In one embodiment, L is —CH=CH—. In one embodiment, L is —CH₂—CH₂—, —CH(Me)-CH₂—, —CH₂—CH(Me)-, —CH₂—CH₂—CH₂—, or —CH=CH—. In one embodiment, L is —CH₂—CH₂—, —CH(Me)-CH₂—, or —CH₂—CH(Me)-. In one embodiment, L is —CH(Me)-CH₂— or —CH₂—CH(Me)-. In one embodiment, L is —CH₂—CH₂—. In one embodiment, L is —CH₂—CH₂—CH₂—. In specific embodiments, m is 2. In specific embodiments, in is 3.
In one embodiment, L is

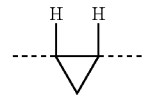

(i.e., a cyclopropylene linker). In one embodiment, L is trans-cyclopropylene. In one embodiment, L is cis-cyclopropylene.
In one embodiment, L is —(C(R¹⁰)₂)ₘ— or

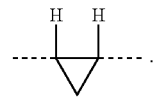

In one embodiment, L is —NR¹¹—C(R¹⁰)₂—, —O—C(R¹⁰)₂—, —S—C(R¹⁰)₂—, —C(R¹⁰)₂—NR¹¹—, —C(R¹⁰)₂)—O—, —C(R¹⁰)₂—S—, or —S—. In one embodiment, each R¹⁰ and R¹¹ is independently hydrogen or methyl. In one embodiment, L is —NR¹¹—CH₂—, —O—CH₂—, —S—CH₂—, —CH₂—NR¹¹—, —CH₂—O—, —CH₂—S—, or —S—. In one embodiment, each R¹¹ is independently hydrogen or methyl.
In one embodiment, A contains from 1 to 2, from 1 to 3, from 1 to 4, from 2 to 3, from 2 to 4, or from 3 to 4 nitrogen ring atoms. In one embodiment, A contains one nitrogen ring atom. In one embodiment, A contains two nitrogen ring atoms. In one embodiment, A contains three nitrogen ring atoms. In one embodiment, A contains four nitrogen ring atoms.
In one embodiment, A is:

wherein Y is defined herein elsewhere.
In one embodiment, A is:

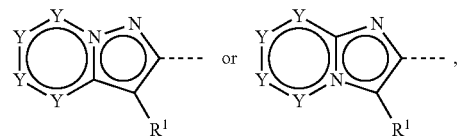

wherein Y and R¹ are defined herein elsewhere. In one embodiment, R¹ is H, halo, cyano, methyl, or CF₃.

In one embodiment, A is:

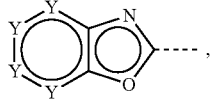

wherein Y is defined herein elsewhere.

In one embodiment, A is:

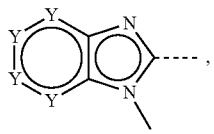

wherein Y is defined herein elsewhere.

In one embodiment, A is:

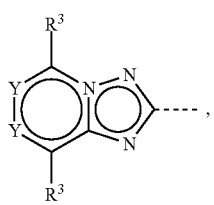

wherein R³ and Y are defined herein elsewhere.

In one embodiment, A is:

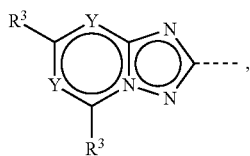

wherein R³ and Y are defined herein elsewhere.

In one embodiment, A is:

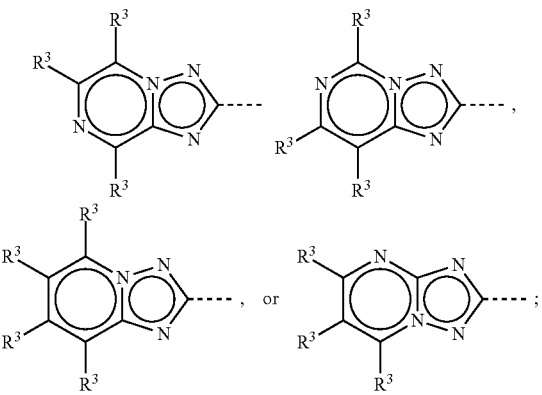

wherein R³ is defined herein elsewhere.

In one embodiment, A is:

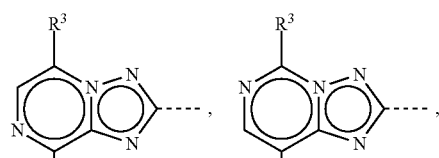
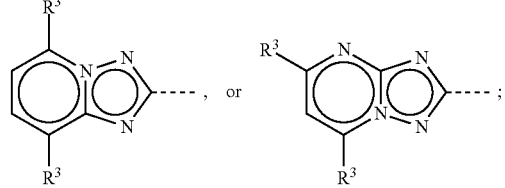

wherein R³ is defined herein elsewhere.

In one embodiment, A is:

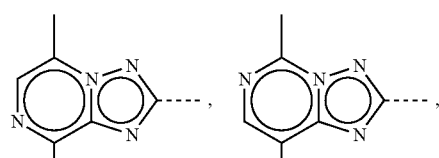
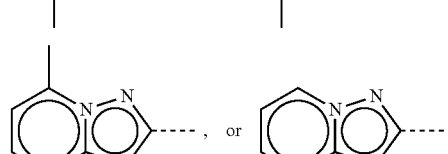

In one embodiment, A is:

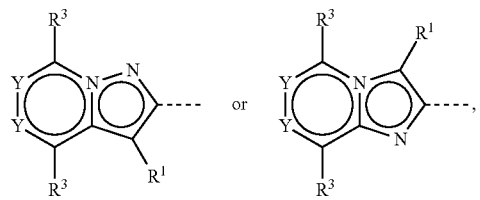

wherein R¹, R³, and Y are defined herein elsewhere. In one embodiment, R¹ is H, halo, cyano, methyl, or CF₃.

In one embodiment, A is:

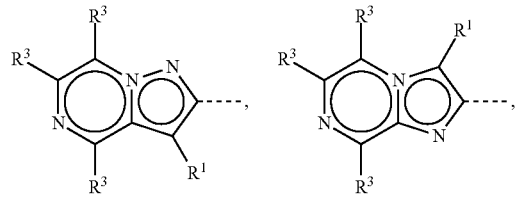
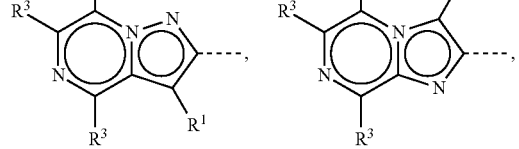

-continued

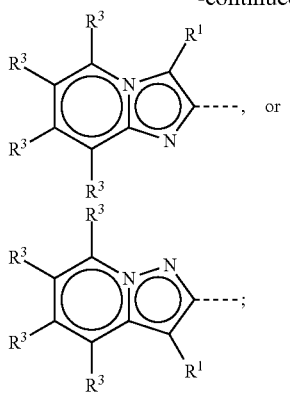

wherein R¹ and R³ are defined herein elsewhere.

In one embodiment, A is:

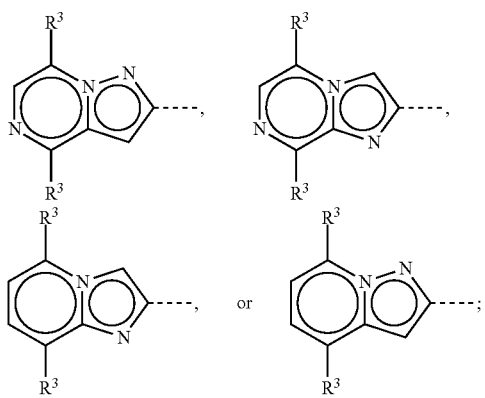

wherein R³ is defined herein elsewhere.

In one embodiment, A is:

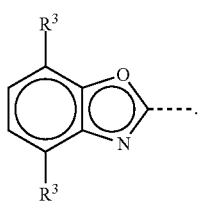

wherein R³ is defined herein elsewhere.

In one embodiment, A is:

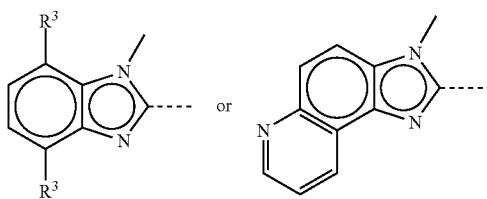

wherein R³ is defined herein elsewhere.

In one embodiment, A is optionally substituted with up to three substituents. In one embodiment, up to three occurrences of R³ substituting A are not hydrogen.

In one embodiment, each $R^3$ is independently hydrogen, halo, cyano, $(C_1$-$C_6)$alkyl, $(C_1$-$C_6)$alkoxyl, $(C_1$-$C_6)$aminoalkyl, $(C_1$-$C_6)$heteroalkyl, aryl, or heteroaryl. In one embodiment, each $R^3$ is independently hydrogen, halo, cyano, $(C_1$-$C_6)$alkyl, or $(C_1$-$C_6)$alkoxyl. In one embodiment, each $R^3$ is independently hydrogen, halo (e.g., F, Cl, or Br), cyano, methyl, ethyl, methoxyl, ethoxyl, $CF_3$, or $OCF_3$. In one embodiment, each $R^3$ is independently hydrogen, F, Cl, cyano, methyl, ethyl, methoxyl, ethoxyl, $CF_3$, or $OCF_3$. In one embodiment, each $R^3$ is independently hydrogen, F, Cl, methyl, ethyl, or $CF_3$. In one embodiment, each $R^3$ is independently hydrogen, Cl, methyl, or $CF_3$. In one embodiment, each $R^3$ is independently hydrogen or methyl. In one embodiment, two adjacent occurrences of $R^3$ together with the atoms to which they are attached form a 5- or 6-membered aryl to heteroaryl ring (e.g., optionally substituted benzene or pyridine).

In one embodiment, X is $CR^1$ or N. In one embodiment, X is O, S, or $NR^2$. In one embodiment, X is O or $NR^2$. In one embodiment, $R^1$ is hydrogen or methyl. In one embodiment, $R^2$ is hydrogen or methyl.

In one embodiment, Y is N. In one embodiment, Y is $CR^3$. In one embodiment, each $R^3$ is independently hydrogen, methyl, ethyl, chloro, or $CF_3$. In one embodiment, each $R^3$ is independently hydrogen or methyl. One occurrence of Y may be the same or different from another occurrence of Y.

In one embodiment, Z is N. In one embodiment, Z is C. One occurrence of Z may be the same or different from another occurrence of Z. In one embodiment, one of the two occurrences of Z is C and the other is N. In one embodiment, one of the two occurrences of Z is N. In one embodiment, at least one of the two occurrences of Z is N. In one embodiment, both occurrences of Z is C.

In one embodiment, B is

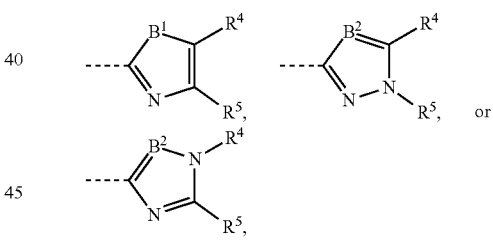

wherein $B^1$, $B^2$, $R^4$, and $R^5$ are defined herein elsewhere. In one embodiment, $R^4$ and $R^5$ together form a monocyclic ring and B is a bicyclic ring system. In one embodiment, $R^4$ and $R^5$ together form a multicyclic ring and B is a tricyclic ring system.

In one embodiment, $B^1$ is —$NR^8$ and $B^2$ is $CR^9$ or N.

In one embodiment, $B^1$ is NH or $NCH_3$. In one embodiment, $B^2$ is CH or N.

In one embodiment, B is a bicyclic ring. In one embodiment, B is a tricyclic ring. In one embodiment, B contains from 1 to 6, from 1 to 5, from 1 to 4, from 2 to 6, from 2 to 5, from 2 to 4, from 2 to 3, from 3 to 4, or from 3 to 5 nitrogen ring atoms. In one embodiment, B contains one nitrogen ring atom. In one embodiment, B contains two nitrogen ring atoms. In one embodiment, B contains three nitrogen ring atoms. In one embodiment, B contains four nitrogen ring atoms. In one embodiment, B contains five nitrogen ring atoms. In one embodiment, B contains six nitrogen ring atoms.

In one embodiment, B is optionally substituted with up to one, up to two, up to three, up to four, up to five, or up to six substituents. In one embodiment, B is optionally substituted with one or more halo, cyano, or methyl.

In one embodiment, B is a bicyclic ring system. In one embodiment, B is:

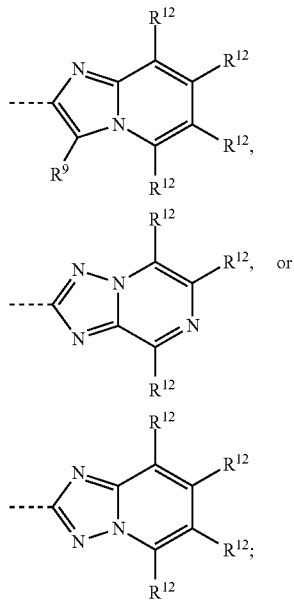

wherein $R^9$ is defined herein elsewhere: and each $R^{12}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, $C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring.

In one embodiment, B is a tricyclic ring system. In one embodiment, B is:

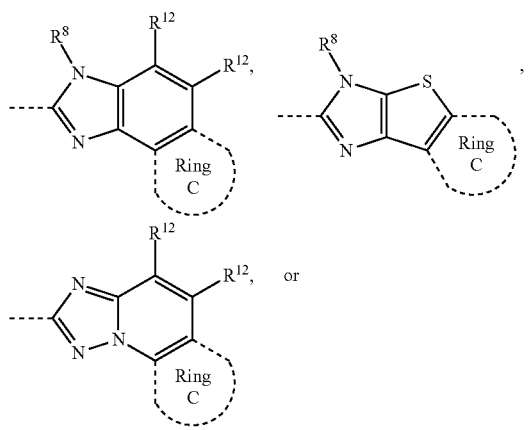

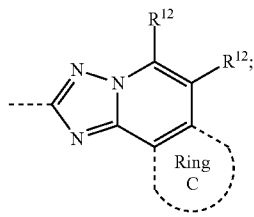

wherein $R^8$ is defined herein elsewhere; each $R^{12}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring; and Ring C is a 5- or 6-membered heteroaryl ring or a 5- to 7-membered cycloalkyl or heterocyclyl ring. In one embodiment, Ring C is a 5- or 6-membered heteroaryl ring (e.g., an optionally substituted pyridine, pyrimidine, pyrazine, pyridazine, thiophene, furan, pyrrole, imidazole, pyrazole, oxazole, isoxazole, thiazole, or isothiazole ring). In another embodiment, Ring C is a 5- to 7-membered cycloalkyl or heterocyclyl ring (e.g., an optionally substituted cyclohexene or dihydrofuran ring). In some embodiments, the heterocyclyl ring contains one to two heteroatom(s) independently selected from N, O, and S. In yet another embodiment, Ring C is a 6-membered aryl ring (e.g., an optionally substituted benzene ring). In one embodiment, Ring C is optionally substituted with one or more $R^{12}$, wherein $R^{12}$ is defined herein elsewhere. In specific embodiments, $R^8$ is hydrogen or methyl. In specific embodiments, $R^{12}$ is hydrogen.

In one embodiment, B is:

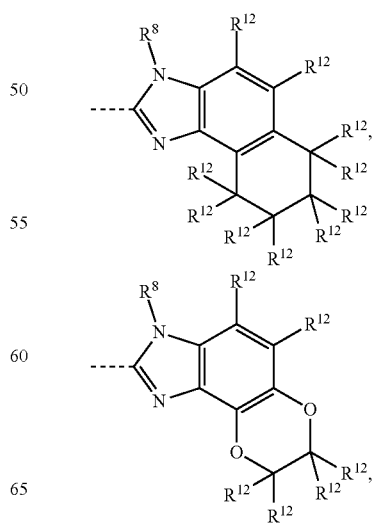

-continued

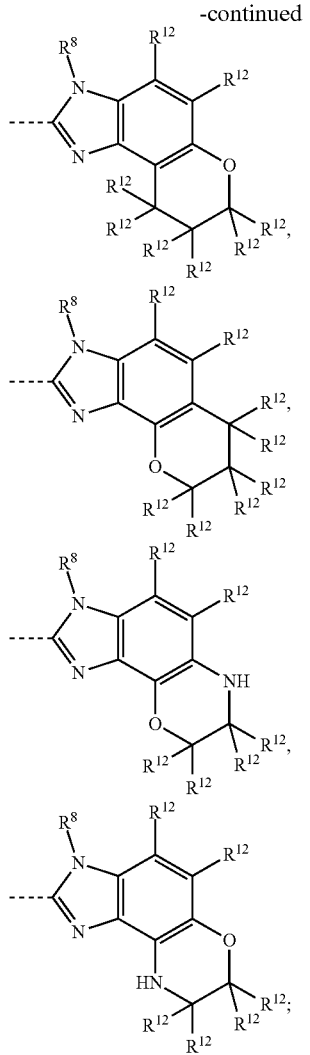

wherein $R^8$ and $R^{12}$ are defined herein elsewhere.

In one embodiment, B is:

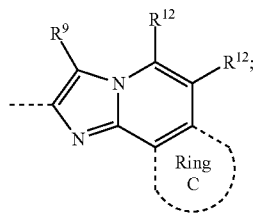

wherein $R^9$ is defined herein elsewhere; each $R^{12}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring; and Ring C is a 5- or 6-membered heteroaryl ring or a 5- to 7-membered cycloalkyl or heterocyclyl ring. In one embodiment, Ring C is a 5- or 6-membered heteroaryl ring (e.g., an optionally substituted pyridine, pyrimidine, pyrazine, pyridazine, thiophene, furan, pyrrole, imidazole, pyrazole, oxazole, isoxazole, thiazole, or isothiazole ring). In another embodiment, Ring C is a 5- to 7-membered cycloalkyl or heterocyclyl ring (e.g., an optionally substituted cyclohexene or dihydrofuran ring). In some embodiments, the heterocyclyl ring contains one to two heteroatom(s) independently selected from N, O, and S. In yet another embodiment, Ring C is a 6-membered aryl ring (e.g., an optionally substituted benzene ring). In one embodiment, Ring C is optionally substituted with one or more $R^{12}$, wherein $R^{12}$ is defined herein elsewhere. In specific embodiments, $R^9$ is hydrogen or methyl. In specific embodiments, $R^{12}$ is hydrogen.

In one embodiment, B is:

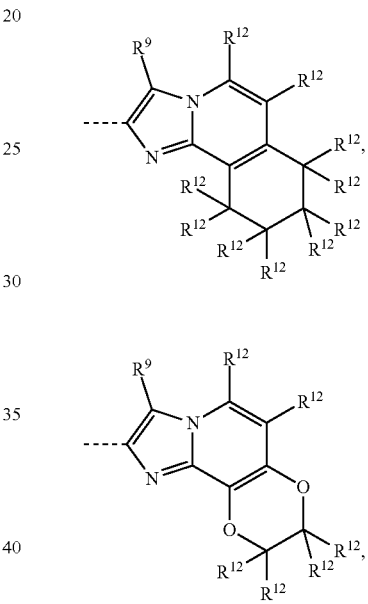

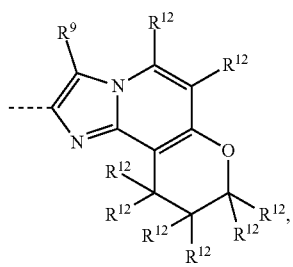

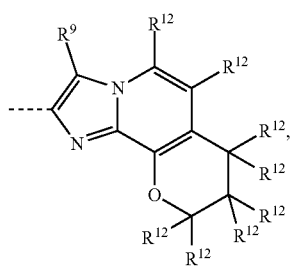

-continued

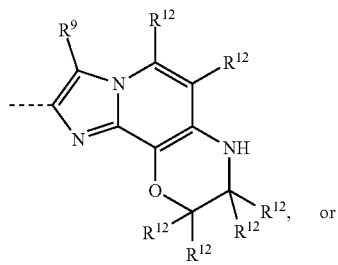, or

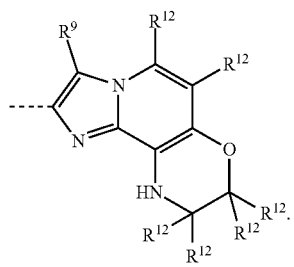

wherein R⁹ and R¹² are defined herein elsewhere.

In one embodiment, B is:

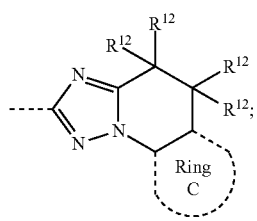

wherein each R¹² is independently hydrogen, halogen, cyano, =O, —OR¹³, —NR¹³R¹⁴, —N(R¹³)C(O)R¹⁴, —C(O)NR¹³R¹⁴, —C(O)R¹³, —C(O)OR¹³, —OC(O)R¹³, —SR¹³, —S(O)R¹³, —S(O)₂R¹³, —S(O)₂NR¹³R¹⁴, alkyl, heteroalkyl, cycloalkyl, aralkyl, heteroaralkyl, aryl, heteroaryl, or heterocyclyl; wherein each R¹³ and R¹⁴ is independently hydrogen, alkyl, heteroalkyl, cycloalkyl, aralkyl, heteroaralkyl, aryl, heteroaryl, or heterocyclyl; or when R¹³ and R¹⁴ are both attached to one nitrogen atom, R¹³ and R¹⁴ together with the nitrogen atom to which they are attached form a 3 to 10 membered ring; and Ring C is a 5- or 6-membered heteroaryl ring, a 5- to 7-membered cycloalkyl or heterocyclyl ring, or a 6-membered aryl ring. In one embodiment, Ring C is optionally substituted with one or more R¹², wherein R¹² is defined herein elsewhere.

In one embodiment, B is:

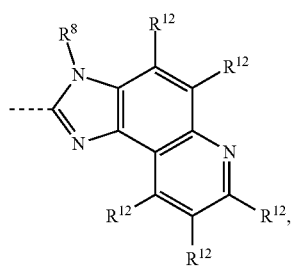

-continued

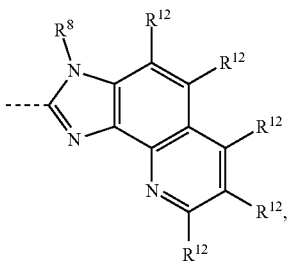

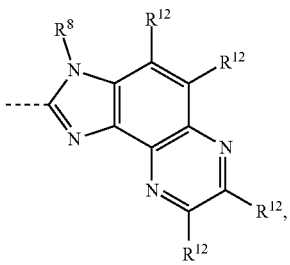

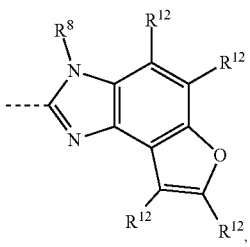

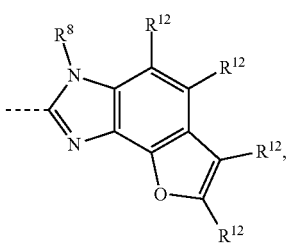

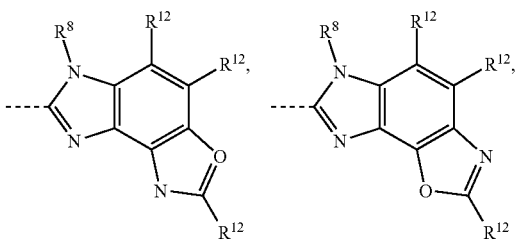

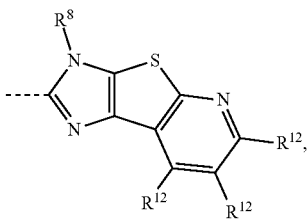

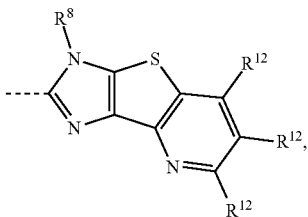

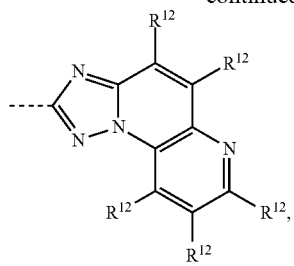
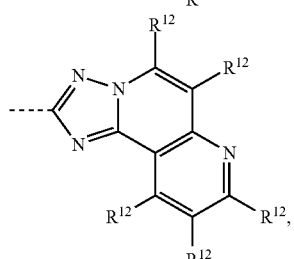
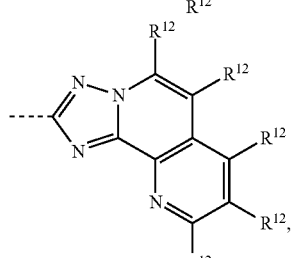
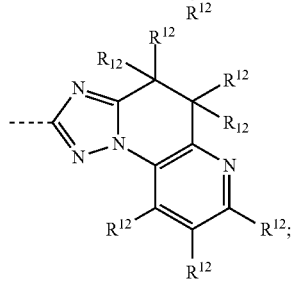
wherein R⁸ and R¹² are defined herein elsewhere.
In one embodiment, B is:
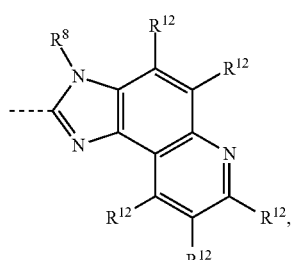
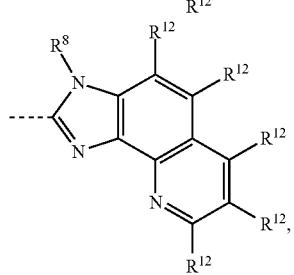
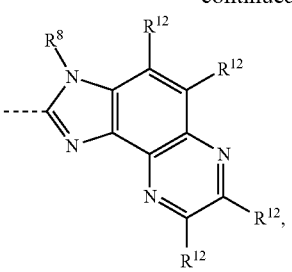
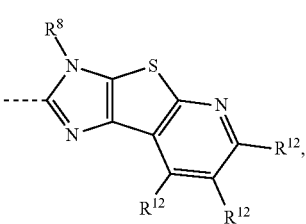
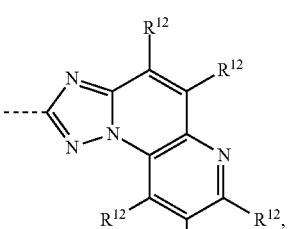
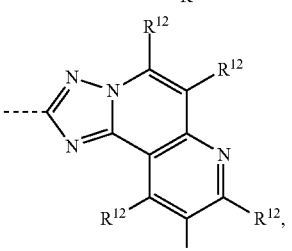
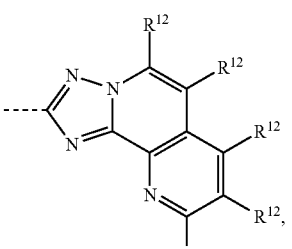
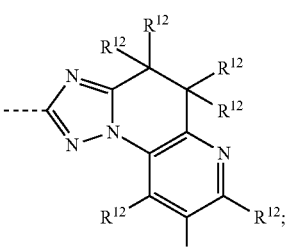
wherein R⁸ and R¹² are defined herein elsewhere.

In one embodiment, B is:

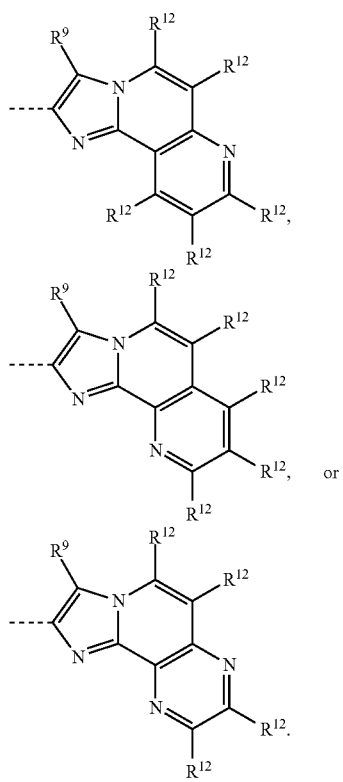

wherein $R^9$ and $R^{12}$ are defined herein elsewhere.

In one embodiment, each $R^8$ and $R^{12}$ is independently hydrogen, halo, cyano, alkyl, or alkoxyl. In one embodiment, each $R^8$ and $R^{12}$ is independently hydrogen, halo (e.g., F or Cl), cyano, $(C_1-C_4)$alkyl (e.g., methyl or $CF_3$), or $(C_1-C_4)$alkoxyl (e.g., methoxyl or $OCF_3$). In one embodiment, each $R^8$ and $R^{12}$ is independently hydrogen or methyl. In one embodiment, $R^8$ is hydrogen or alkyl. In one embodiment, each $R^{12}$ is independently hydrogen, halo, cyano, alkyl, or alkoxyl (e.g., $-OR^{13}$). In one embodiment, $R^8$ is hydrogen or $(C_1-C_4)$alkyl (e.g., methyl or ethyl). In one embodiment, each $R^{12}$ is independently hydrogen, halo (e.g., F or Cl), cyano, $(C_1-C_4)$alkyl (e.g., methyl or $CF_3$), or $(C_1-C_4)$alkoxyl (e.g., methoxyl or $OCF_3$). In one embodiment, $R^8$ is hydrogen or methyl. In one embodiment, each $R^{12}$ is independently hydrogen or methyl. In one embodiment, each $R^9$ and $R^{12}$ is independently hydrogen, halo, cyano, alkyl, or alkoxyl. In one embodiment, each $R^9$ and $R^{12}$ is independently hydrogen, halo (e.g., F or Cl), cyano, $(C_1-C_4)$alkyl (e.g., methyl or $CF_3$), or $(C_1-C_4)$alkoxyl (e.g., methoxyl or $OCF_3$). In one embodiment, each $R^9$ and $R^{12}$ is independently hydrogen or methyl.

In one embodiment, two occurrences of $R^3$ together with the atoms to which they are attached form an aryl, heteroaryl, cycloalkyl, or heterocyclyl ring, including but not limited to, an optionally substituted phenyl, pyridyl, pyrimidyl, pyrazinyl, pyridazinyl, imidazolyl, thienyl, or thiazolyl, or a 5- or 6-membered heterocyclyl ring. In one embodiment, two adjacent occurrences of $R^3$ together with the atoms to which they are attached form an aryl or heteroaryl ring, including but not limited to, an optionally substituted phenyl, pyridyl, pyrimidyl, pyrazinyl, pyridazinyl, imidazolyl, thienyl, or thiazolyl. In one embodiment, $R^4$ and $R^5$ together with the atoms to which they are attached form an aryl, heteroaryl, cycloalkyl, or heterocyclyl ring, including but not limited to, an optionally substituted phenyl, pyridyl, pyrimidyl, pyrazinyl, pyridazinyl, imidazolyl, thienyl, or thiazolyl, or a 5- or 6-membered heterocyclyl ring.

In one embodiment, provided herein is a compound of formula (II-A):

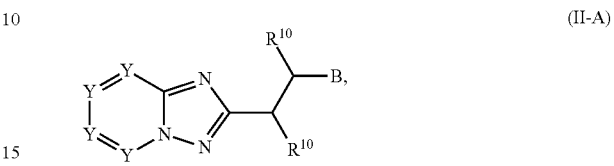

(II-A)

or a pharmaceutically acceptable salt or stereo isomer thereof, wherein Y, $R^{10}$, and B are defined herein elsewhere.

In one embodiment, provided herein is a compound of the formula:

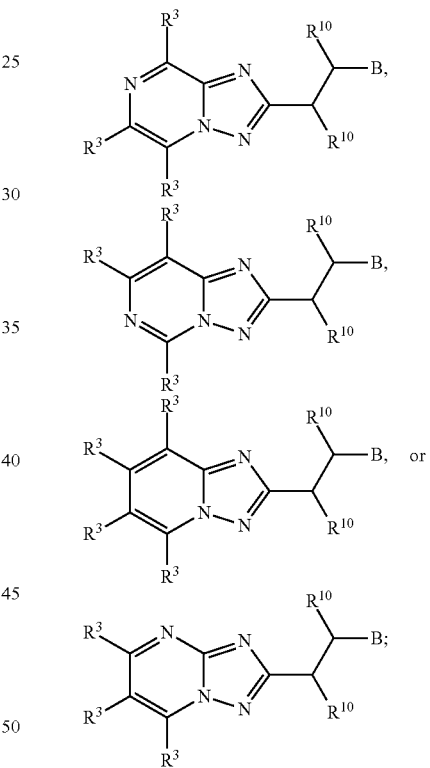

or a pharmaceutically acceptable salt or stereoisomer thereof, wherein $R^3$, $R^{10}$, and B are defined herein elsewhere. In specific embodiments, each $R^3$ is independently hydrogen, methyl, ethyl, $CF_3$, or halo. In specific embodiments, $R^{10}$ is hydrogen. In specific embodiments, $R^{10}$ is hydrogen or methyl.

In one embodiment, B is

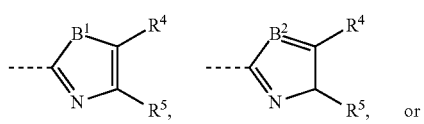

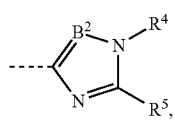
wherein $B^1$, $B^2$, $R^4$, and $R^5$ are defined herein elsewhere.
In one embodiment, B is a bicyclic ring system. Examples include, but are not limited to:
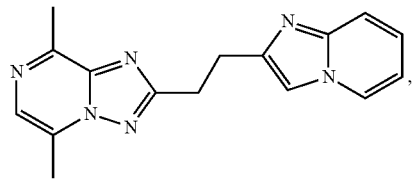
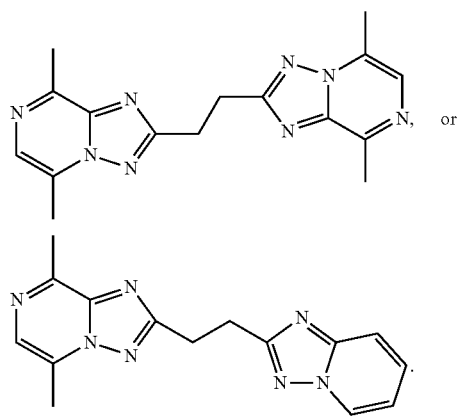
In one embodiment, B is a tricyclic ring system. Examples include, but are not limited to:
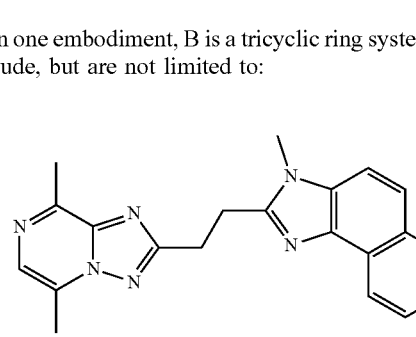
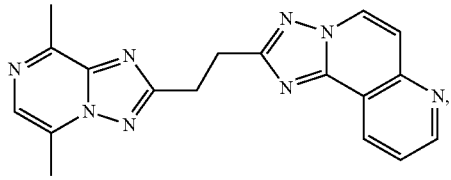
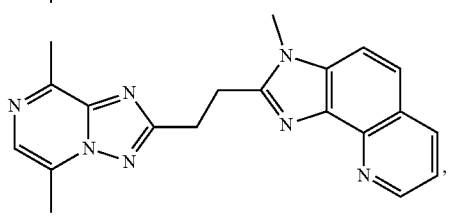
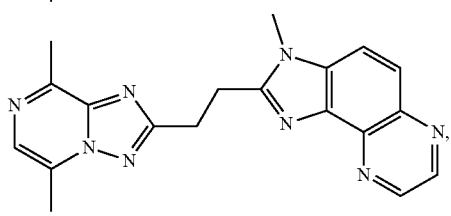
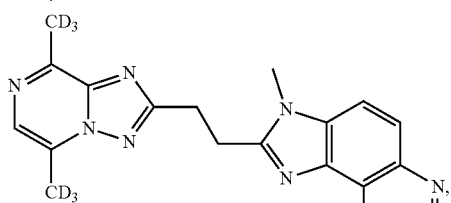
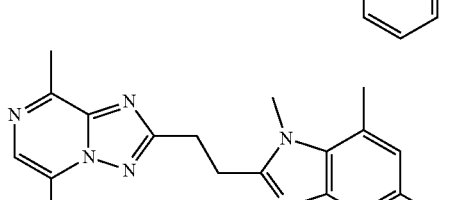
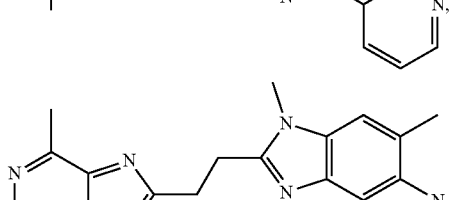
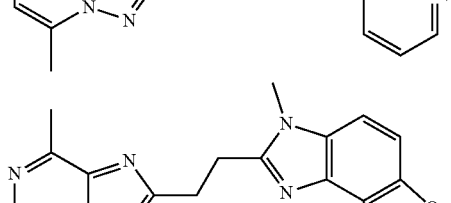
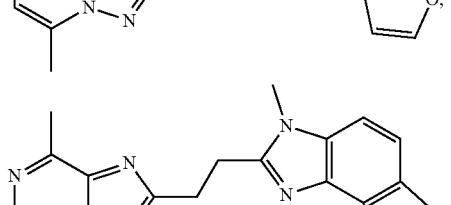

-continued
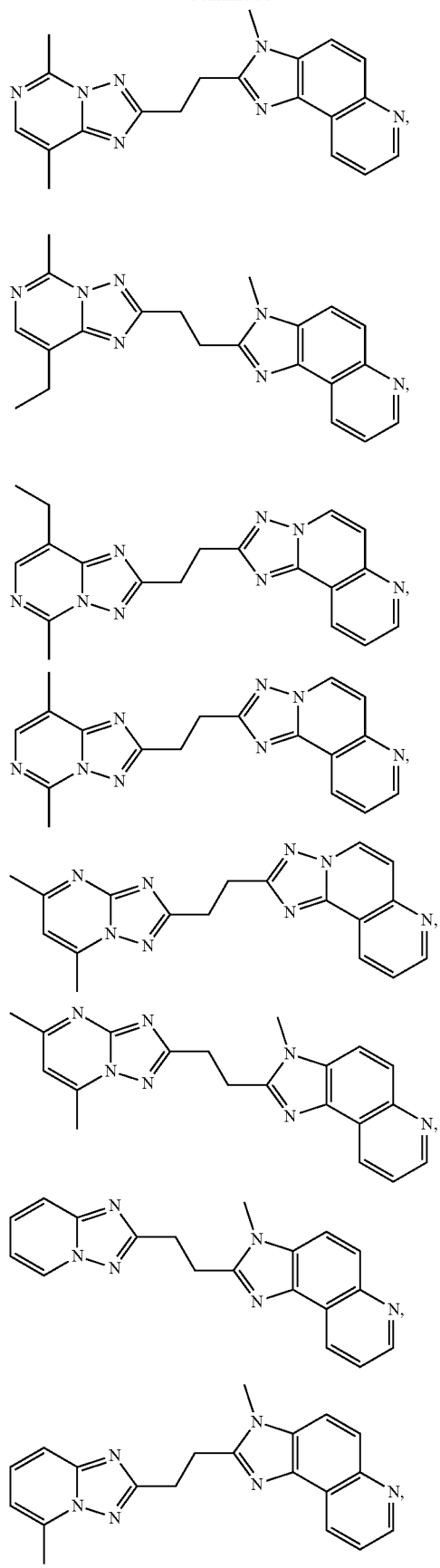
-continued
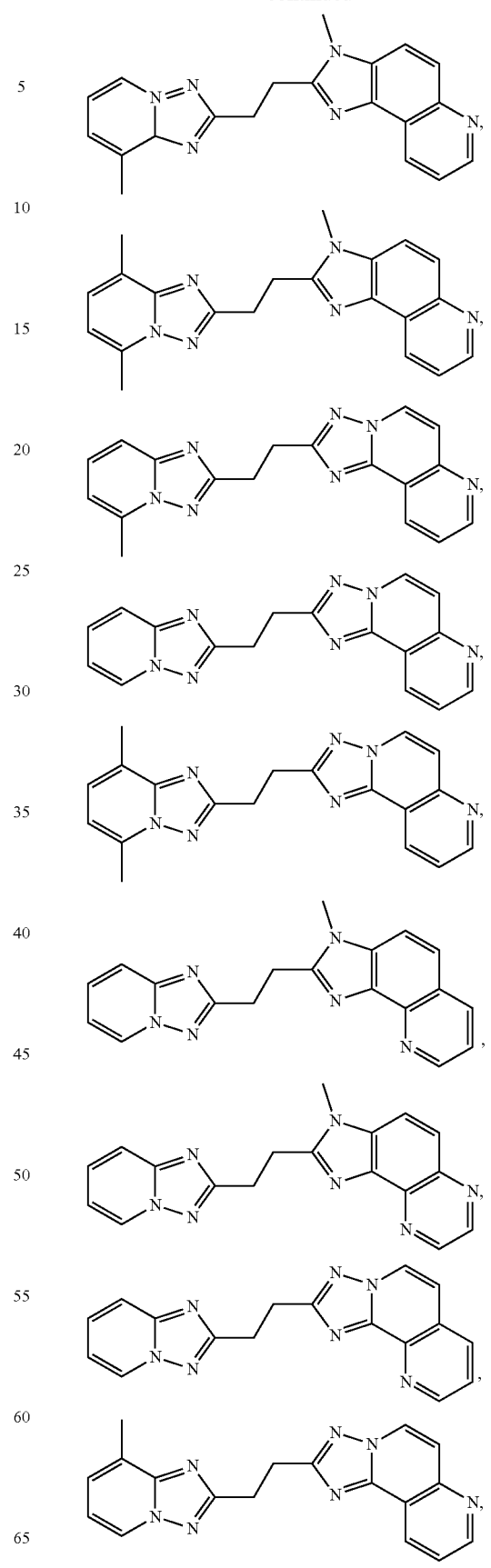

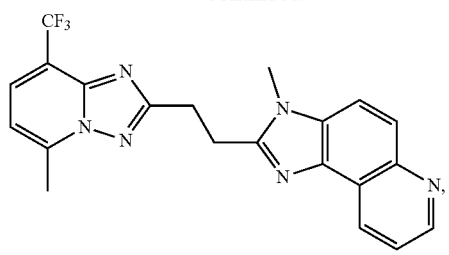
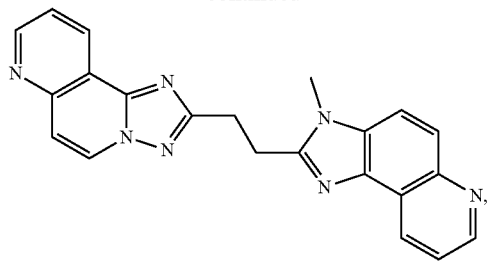
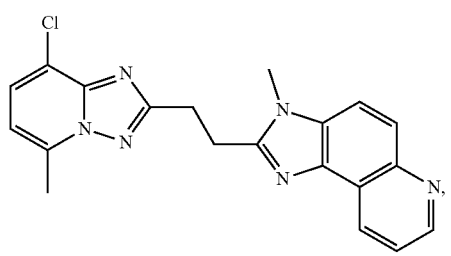
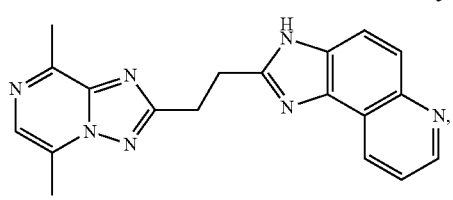
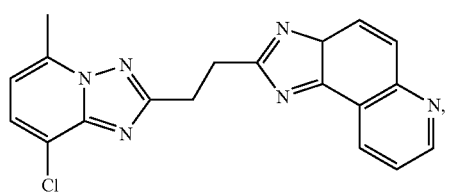
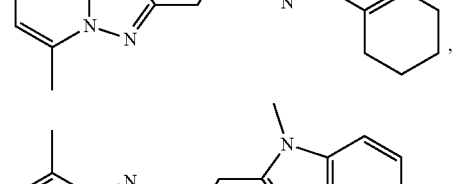
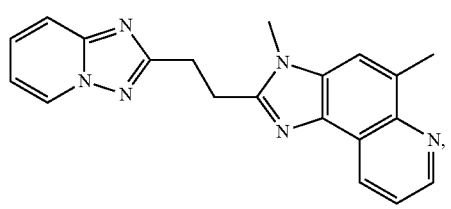 [SMILES: Cn1c(CCc2nc3ccccc3o2)nc2c3cccnc3ccc21]
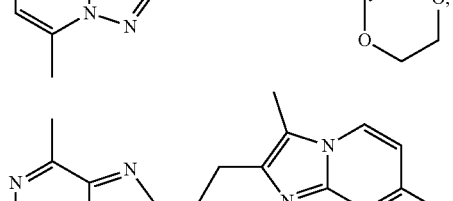
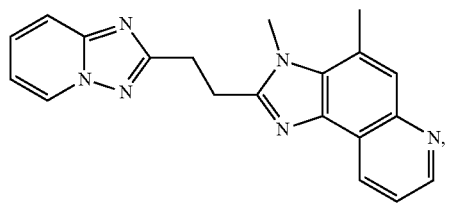
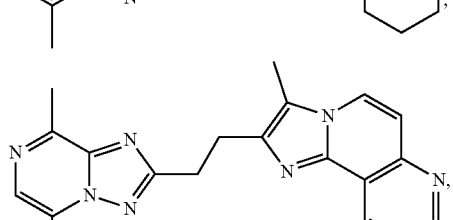
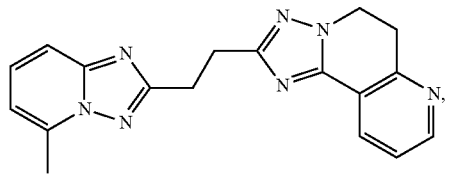
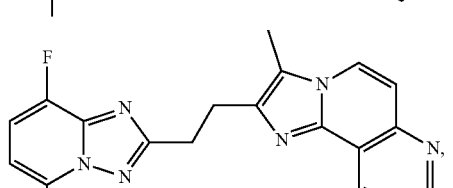
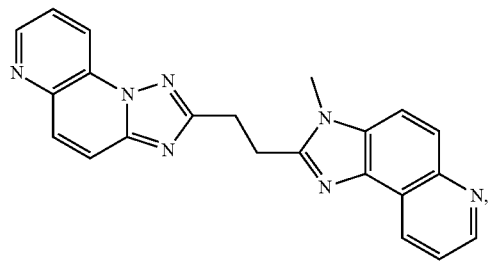
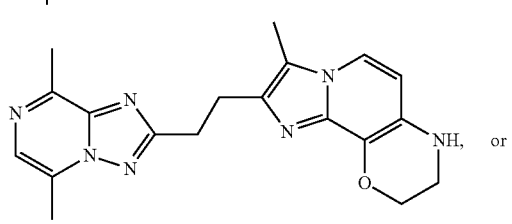

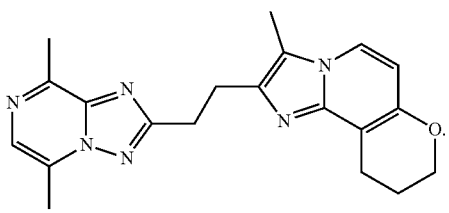

In one embodiment, each $R^{10}$ is independently hydrogen or methyl. In one embodiment, at least one $R^{10}$ is methyl. Examples include, but are not limited to:

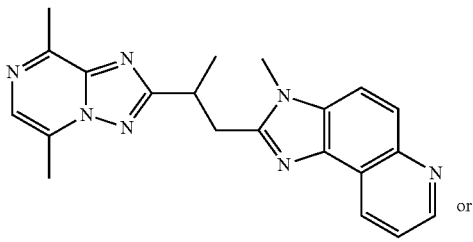
or

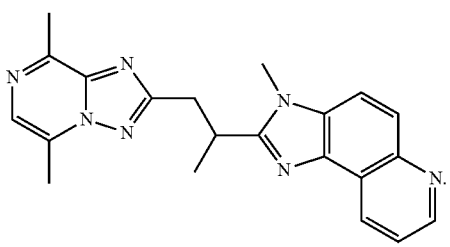

In one embodiment, provided herein is a compound of formula (II-B):

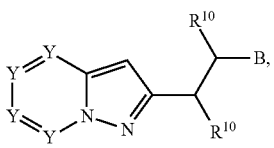
(II-B)

or a pharmaceutically acceptable salt or stereoisomer thereof, wherein Y, $R^{10}$, and B are defined herein elsewhere.

In one embodiment, provided herein is a compound of the formula:

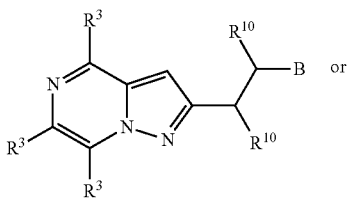
or

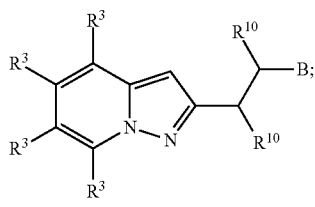

or a pharmaceutically acceptable salt or stereoisomer thereof, wherein $R^3$, $R^{10}$, and B are defined herein elsewhere. In specific embodiments, each $R^3$ is independently hydrogen, methyl, ethyl, CF3, or halo. In specific embodiments, $R^{10}$ is hydrogen. In specific embodiments, $R^{10}$ is hydrogen or methyl.

In one embodiment, B is

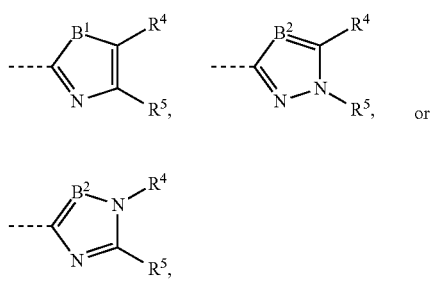
or wherein $B^1$, $B^2$, $R^4$, and $R^5$ are defined herein elsewhere. In one embodiment, B is a tricyclic ring system. Examples include, but are not limited to:

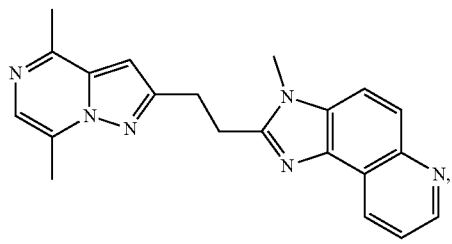

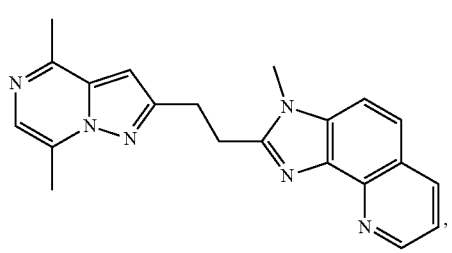

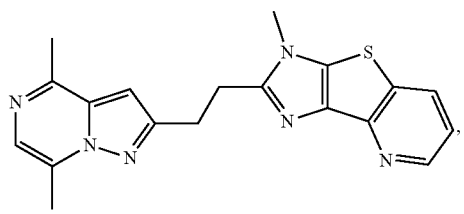

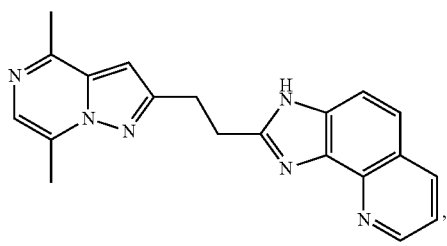

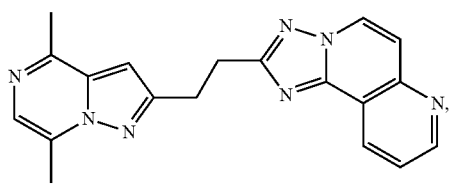

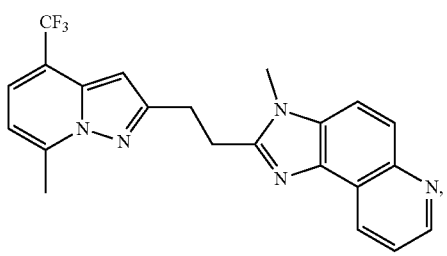

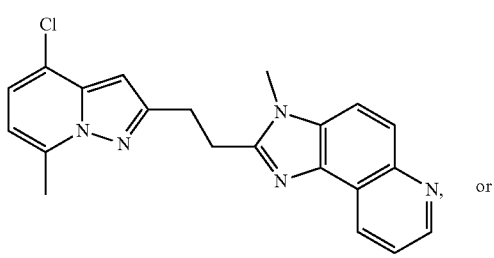

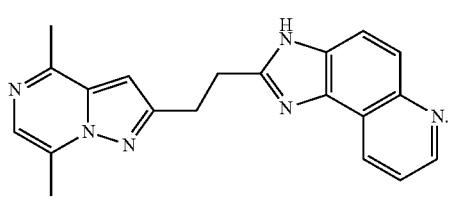

In one embodiment, provided herein is a compound of formula (II-C):

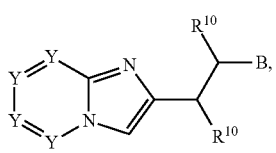
(II-C)

or a pharmaceutically acceptable salt or stereoisomer thereof, wherein Y, $R^{10}$, and B are defined herein elsewhere.

In one embodiment, provided herein is a compound of the formula:

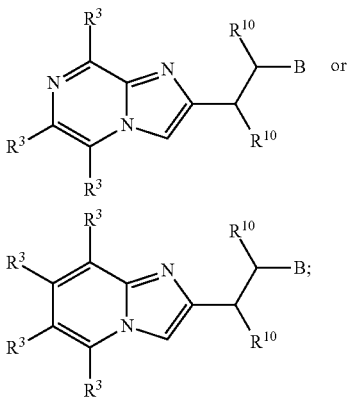

or a pharmaceutically acceptable salt or stereoisomer thereof, wherein $R^3$, $R^{10}$, and B are defined herein elsewhere. In specific embodiments, each $R^3$ is independently hydrogen, methyl, ethyl, CF3, or halo. In specific embodiments, $R^{10}$ is hydrogen. In specific embodiments, $R^{10}$ is hydrogen or methyl.

In one embodiment, B is

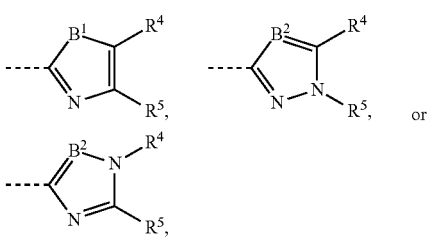

wherein $B^1$, $B^2$, $R^4$, and $R^5$ are defined herein elsewhere. In one embodiment, B is a tricyclic ring system. Examples include, but are not limited to:

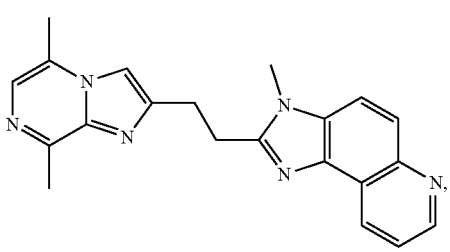

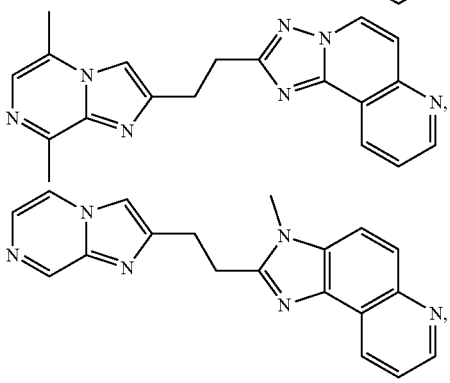

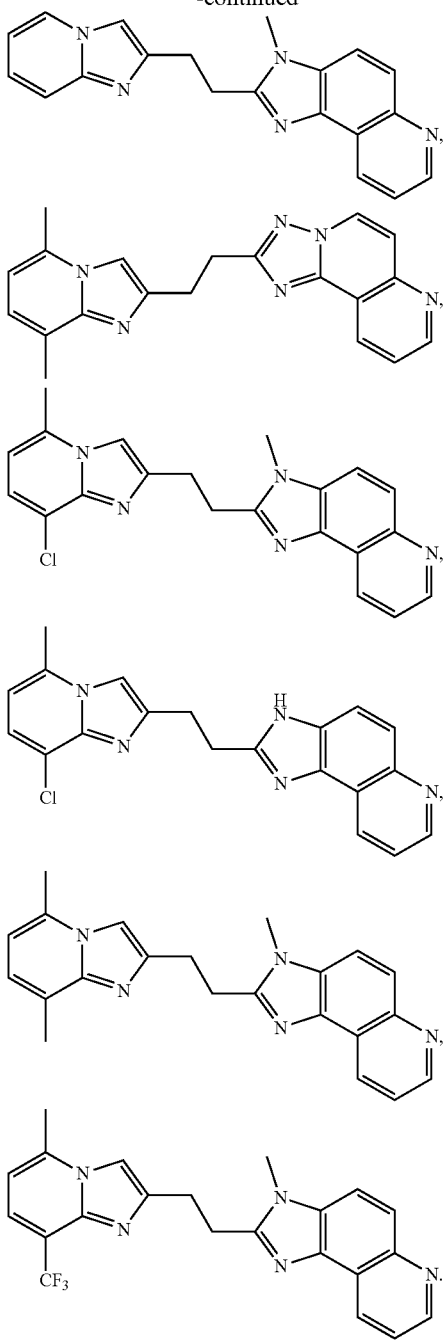

In one embodiment, provided herein is a compound of formula (II-D):

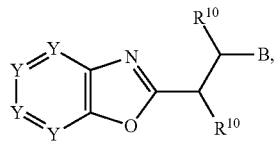

or a pharmaceutically acceptable salt or stereoisomer thereof, wherein Y, $R^{10}$, and B are defined herein elsewhere.

In one embodiment, B is a tricyclic ring system. An example includes, but is not limited to:

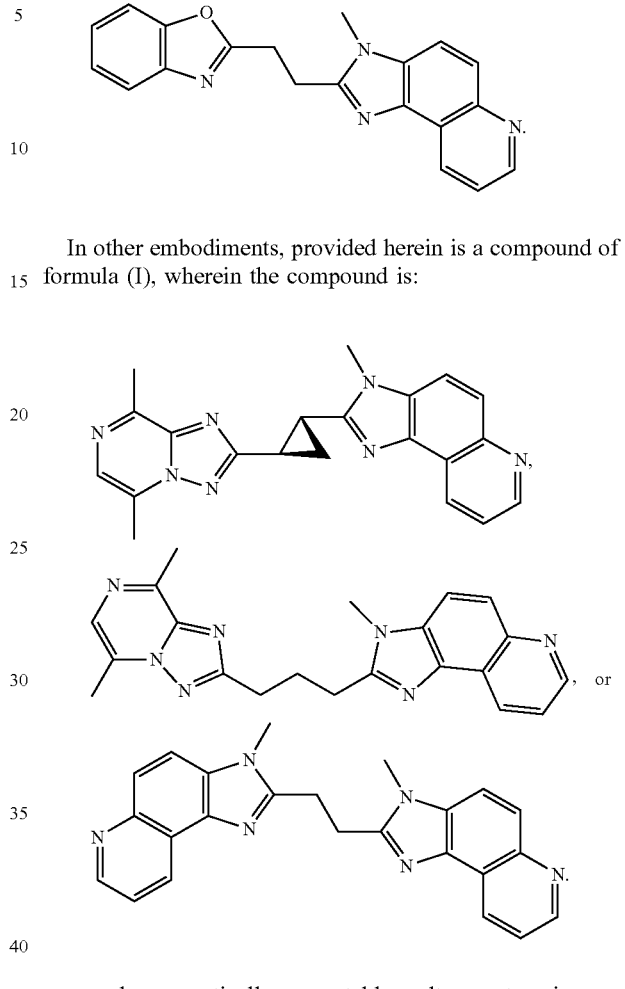

In other embodiments, provided herein is a compound of formula (I), wherein the compound is:

or a pharmaceutically acceptable salt or stereoisomer thereof.

In other embodiments, provided herein is a compound having the structure:

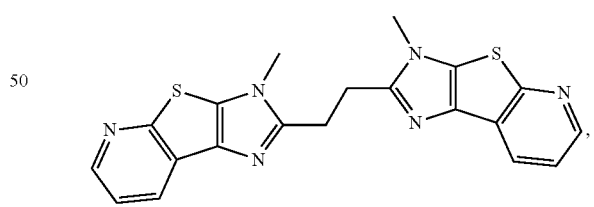

or a pharmaceutically acceptable salt or stereoisomer thereof.

In one embodiment, $R^1$ is (i) hydrogen, halo, or cyano; or (ii) ($C_1$-$C_6$)alkyl, ($C_2$-$C_6$)alkenyl, ($C_1$-$C_6$)alkoxyl, ($C_1$-$C_6$) aminoalkyl, ($C_1$-$C_6$)heteroalkyl, ($C_3$-$C_6$)cycloalkyl, aryl, heteroaryl, heterocyclyl, amino, amido, carbonyl, thiol, sulfinyl, or sulfonyl, each of which is optionally substituted with one or more $R^{12}$, wherein $R^{12}$ is defined herein.

In one embodiment, $R^2$ is (i) hydrogen; or (ii) ($C_1$-$C_6$) alkyl, ($C_2$-$C_6$)alkenyl, ($C_1$-$C_6$)heteroalkyl, ($C_3$-$C_6$) cycloalkyl, aryl, heteroaryl, heterocyclyl, carbonyl, or sulfonyl, each of which is optionally substituted with one or more $R^{12}$, wherein $R^{12}$ is defined herein.

In one embodiment, each $R^3$ is independently (i) hydrogen, halo, or cyano; (ii) ($C_1$-$C_6$)alkyl, ($C_2$-$C_6$)alkenyl, ($C_1$-$C_6$)alkoxyl, ($C_1$-$C_6$)aminoalkyl, ($C_1$-$C_6$)heteroalkyl, ($C_3$-$C_6$)cycloalkyl, aryl, heteroaryl, heterocyclyl, amino, amido, carbonyl, thiol, sulfinyl, or sulfonyl, each of which is optionally substituted with one or more $R^{12}$; or (iii) two adjacent occurrences of $R^3$ together with the atoms to which they are attached form an aryl or heteroaryl ring optionally substituted with one or more $R^{12}$; wherein $R^{12}$ is defined herein.

In one embodiment, $R^4$ and $R^5$ together with the atoms to which they are attached form a monocyclic or multicyclic aryl, heteroaryl, cycloalkyl, or heterocyclyl ring, each of which is optionally substituted with one or more $R^{12}$; wherein $R^{12}$ is defined herein.

In one embodiment, $R^6$ is (i) hydrogen, halo, or cyano; or (ii) ($C_1$-$C_6$)alkyl, ($C_2$-$C_6$)alkenyl, ($C_1$-$C_6$)alkoxyl, ($C_1$-$C_6$)aminoalkyl, ($C_1$-$C_6$)heteroalkyl, ($C_3$-$C_6$)cycloalkyl, aralkyl, heteroaralkyl, aryl, heteroaryl, heterocyclyl, amino, amido, carbonyl, thiol, sulfinyl, or sulfonyl, each of which is optionally substituted with one or more $R^{12}$; wherein $R^{12}$ is defined herein.

In one embodiment, $R^7$ is (i) hydrogen; or (ii) ($C_1$-$C_6$)alkyl, ($C_2$-$C_6$)alkenyl, ($C_1$-$C_6$)heteroalkyl, ($C_3$-$C_6$)cycloalkyl, aryl, heteroaryl, heterocyclyl, carbonyl, or sulfonyl, each of which is optionally substituted with one or more $R^{12}$; wherein $R^{12}$ is defined herein.

In one embodiment, $R^8$ is (i) hydrogen; or (ii) ($C_1$-$C_6$)alkyl, ($C_2$-$C_6$)alkenyl, ($C_1$-$C_6$)heteroalkyl, ($C_3$-$C_6$)cycloalkyl, aryl, heteroaryl, heterocyclyl, carbonyl, or sulfonyl, each of which is optionally substituted with one or more $R^{12}$; wherein $R^{12}$ is defined herein.

In one embodiment, $R^9$ is (i) hydrogen, halo, or cyano; or (ii) ($C_1$-$C_6$)alkyl, ($C_2$-$C_6$)alkenyl, ($C_1$-$C_6$)alkoxyl, ($C_1$-$C_6$)aminoalkyl, ($C_1$-$C_6$)heteroalkyl, ($C_3$-$C_6$)cycloalkyl, aralkyl, heteroaralkyl, aryl, heteroaryl, heterocyclyl, amino, amido, carbonyl, thiol, sulfinyl, or sulfonyl, each of which is optionally substituted with one or more $R^{12}$; wherein $R^{12}$ is defined herein.

In one embodiment, each $R^{10}$ is independently hydrogen, halo, or ($C_1$-$C_6$)alkyl optionally substituted with one or more $R^{12}$; wherein $R^{12}$ is defined herein.

In one embodiment, each $R^{11}$ is hydrogen or ($C_1$-$C_6$)alkyl optionally substituted with one or more $R^{12}$; wherein $R^{12}$ is defined herein.

In one embodiment, each $R^{12}$ is independently (i) hydrogen, halogen, cyano, =O, —$OR^{13}$, —$NR^{13}R^{14}$, —$N(R^{13})$$C(O)R^{14}$, —$C(O)NR^{13}R^{14}$, —$C(O)R^{13}$, —$C(O)$$OR^{13}$, —$OC(O)R^{13}$, —$SR^{13}$, —$S(O)R^{13}$, —$S(O)_2R^{13}$, —$S(O)_2NR^{13}R^{14}$; or (ii) ($C_1$-$C_{10}$)alkyl optionally substituted with one or more $R^{15}$, ($C_1$-$C_{10}$) heteroalkyl optionally substituted with one or more $R^{15}$, ($C_3$-$C_{10}$)cycloalkyl optionally substituted with one or more $R^{15}$, ($C_7$-$C_{12}$)aralkyl optionally substituted with one or more $R^{15}$, ($C_3$-$C_{12}$)heteroaralkyl optionally substituted with one or more $R^{15}$, (6 to 10 membered)aryl optionally substituted with one or more $R^{15}$, (5 to 10 membered)heteroaryl optionally substituted with one or more $R^{15}$, or (3 to 12 membered)heterocyclyl optionally substituted with one or more $R^{15}$; wherein $R^{13}$, $R^{14}$, and $R^{15}$ are defined herein.

In one embodiment, each occurrence of $R^{15}$ is independently hydrogen, ($C_1$-$C_6$)alkyl optionally substituted with one or more $R^{13}$, ($C_3$-$C_6$)cycloalkyl optionally substituted with one or more $R^{13}$, halogen, cyano, =O, —$OR^{13}$, —$NR^{13}R^{14}$, —$N(R^{13})C(O)R^{14}$, —$C(O)NR^{13}R^{14}$, —$C(O)$$R^{13}$, —$C(O)OR^{13}$, —$OC(O)R^{13}$, —$SR^{13}$, —$S(O)R^{13}$, —$S(O)_2R^{13}$, or —$S(O)_2NR^{13}R^{14}$; wherein $R^{13}$ and $R^{14}$ are defined herein.

In one embodiment, each $R^{13}$ and $R^{14}$ is independently hydrogen, ($C_1$-$C_6$)alkyl, ($C_1$-$C_6$)heteroalkyl, ($C_3$-$C_6$)cycloalkyl, ($C_7$-$C_{10}$)aralkyl; ($C_3$-$C_{12}$)heteroaralkyl, (6 to 10 membered) aryl, (5 to 10 membered)heteroaryl, or (3 to 12 membered)heterocyclyl; or when $R^{13}$ and $R^{14}$ are both attached to one nitrogen atom, $R^{13}$ and $R^{14}$ together with the nitrogen atom to which they are attached form a 3 to 10 membered ring.

Any of the combinations of A, B, L, m, K, X, Y, Z, $B^1$, $B^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and Ring C, are encompassed by this disclosure and specifically provided herein.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one geometric (i.e., cis/trans) isomer or a mixture of geometric (i.e., cis/trans) isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism.

Unless otherwise specified, the term "compound" referred to herein, such as, a compound of formula (I), (II-A), (II-B), (II-C), or (II-D) is intended to encompass one or more of the following: a free base of the compound or a salt thereof, a stereoisomer or a mixture of two or more stereoisomers, a solid form (e.g., a crystal form or an amorphous form) or a mixture of two or more solid forms thereof, or a solvate (e.g., a hydrate) thereof. In certain embodiments, the term "compound" referred to herein is intended to encompass a pharmaceutical acceptable form of the compound, including but not limited to, a free base, a pharmaceutically acceptable salt, a stereoisomer or a mixture of two or more stereoisomers, a solid form (e.g., a crystal form or an amorphous form) or a mixture of two or more solid forms, a solvate (e.g., a hydrate), or a cocrystal thereof. In one embodiment, the term "compound" referred to herein, such as, e.g., a compound of formula (I), (II-A), (II-B), (II-C), or (II-D) is intended to encompass a solvate (e.g., a hydrate) thereof.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharma. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In one embodiment, the compounds provided herein are modulators of a PDE enzyme. In one embodiment, the compounds provided herein are inhibitors of a PDE enzyme. In one embodiment, the compounds provided herein are inhibitors of PDE-10. In one embodiment, the compounds provided herein are inhibitors of PDE-10A. In one embodiment, the compounds provided herein are selective inhibitors of PDE-10. In one embodiment, the compounds provided herein are selective inhibitors of PDE-10A. In one embodiment, the compounds provided herein are active in one or more animal models for a disorder provided herein elsewhere. In one embodiment, the compounds provided herein are active in one or more animal models for a CNS disorder provided herein elsewhere. In one embodiment, the compounds provided herein are active in one or more animal models for psychosis, schizophrenia, or antipsychotic activity, including without limitation, the conditioned avoidance response (CAR) assay, and any other animal models for psychosis, schizophrenia or antipsychotic activity that are known in the art. In one embodiment, the compounds provided herein are active in one or more animal models for psychosis, schizophrenia, or antipsychotic activity, including but not limited to, conditioned avoidance response (CAR), pre-pulse inhibition (PPI), PCP-induced hyperlocomotion, and other animal models provided herein elsewhere. In one embodiment, compounds that are active in in vitro assays (e.g., PDE-10A inhibition) or in vivo models for psychosis, schizophrenia or antipsychotic activity (e.g., CAR) are further optimized to improve the potency in in vitro and in vivo assays and drug-like properties such as, e.g., solubility and lipophilicity. In one embodiment, the compounds provided herein are useful for treating, preventing, or ameliorating one or more symptoms of schizophrenia, including, positive, negative, and cognitive symptoms. In one embodiment, the compounds provided herein induce fewer side effects, such as weight gain, in a subject treated with the compound. In one embodiment, the compounds provided herein induce fewer side effects, such as extrapyramidal side effects, in a subject treated with the compound.

In one embodiment, the compounds provided herein are active in one or more animal models for obesity, undesirable weight retention or weight gain, metabolic syndrome, diabetes, non-insulin dependent diabetes, impaired glucose tolerance, or hyperglycemia, including without limitation, in vivo glucose tolerance test (GTT), diet-induced obesity model, obesity food intake model, and any other animal models known in the art or provided herein elsewhere. In one embodiment, compounds that are active in in vitro assays (e.g., PDE-10A inhibition) or in vivo models for obesity, undesirable weight retention or weight gain, metabolic syndrome, diabetes, non-insulin dependent diabetes, impaired glucose tolerance, or hyperglycemia are further optimized to improve the potency in in vitro and in vivo assays and drug-like properties such as, e.g., solubility and lipophilicity.

C. Synthetic Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In one embodiment, the compound of formula (I) may be prepared following Schemes 1-4, using suitable starting materials known in the art and/or available from a commercial source. In one embodiment, the starting materials of Schemes 1-4 may be prepared from commercially available compounds using procedures and conditions known in the art. Exemplary procedures and conditions are provided herein elsewhere.

Scheme 1

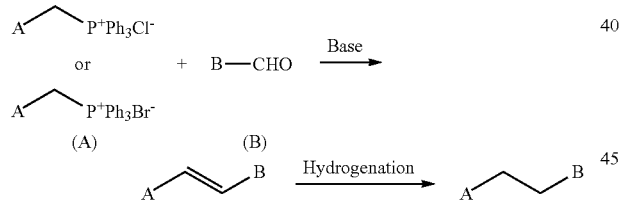

In one embodiment, a suitable triphenylphosphine halide (e.g., a substituted methyltriphenylphosphine chloride or bromide) is reacted with a suitable aldehyde or ketone in the presence of a base to render a substituted ethylene (Scheme 1), which may be further reduced (e.g., by hydrogenation) to render a substituted ethane compound as shown in Scheme 1. In one embodiment, A or B may be further converted into other suitable embodiments of A or B (e.g., transformation of substitution groups) using procedures and conditions known in the art.

Scheme 2

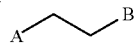

In one embodiment, a suitable A-CH$_3$ is reacted with a suitable aldehyde in the presence of acid (e.g., acetic acid, zinc chloride, heating) to render a substituted ethylene (Scheme 2), which may be further reduced (e.g., by hydrogenation) to render a substituted ethane compound as shown in Scheme 2. In one embodiment, A or B may be further converted into other suitable embodiments of A or B (e.g., transformation of substitution groups) using procedures and conditions known in the art.

Scheme 3

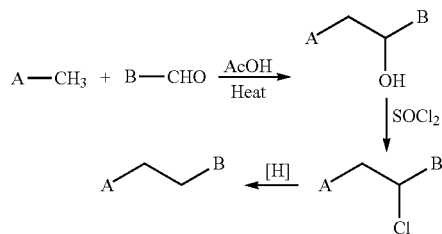

In another embodiment, a suitable A-CH$_3$ is reacted with a suitable aldehyde in the presence of acid (e.g., acetic acid, heating) to render a substituted hydroxylethylene compound (Scheme 3), which is converted to the corresponding chloride (e.g., using SOCl$_2$) and reduced (e.g., using Pd on Carbon) to render a substituted ethane compound as shown in Scheme 3. In one embodiment, A or B may be further converted into other suitable embodiments of A or B (e.g., transformation of substitution groups) using procedures and conditions known in the art.

Scheme 4

In one embodiment, a suitable substituted diaminoaryl or substituted diaminoheteroaryl is reacted with a suitable substituted propionic acid under amide coupling conditions to yield the corresponding amide (Scheme 4), which is cyclized under acidic condition (e.g., acetic acid) to render a substituted ethyl-imidazole compound as shown in Scheme 4. In one embodiment, the diaminoaryl or diaminoheteroaryl compound is substituted with one or more R, a suitable substituent, which may be the same or different, and two adjacent occurrences of R may together with the atoms to which they are attached form a ring (e.g., aryl, heteroaryl, heterocyclyl, or cycloalkyl ring, which is optionally substituted as defined herein elsewhere). In one embodiment, Ar or R may be further converted into other suitable embodiments of Ar or R. (e.g., transformation of substitution groups) using procedures and conditions known in the art. In one embodiment, the imidazole ring may be further alkylated to render an N-substituted imidazole compound.

In other embodiments, the compounds provided herein may be prepared using the general procedures described herein below. In one embodiment, the compounds provided herein may be prepared using General Procedure A. In one embodiment, the compounds provided herein may be prepared using General Procedure B. In one embodiment, the compounds provided herein may be prepared using General Procedure C. In one embodiment, the compounds provided herein may be prepared using General Procedure D. In one embodiment, the compounds provided herein may be prepared using General Procedure E. In one embodiment, the compounds provided herein may be prepared using General Procedure F. In one embodiment, the compounds provided herein may be prepared using General Procedure G. In one embodiment, the compounds provided herein may be prepared using General Procedure H. In one embodiment, the compounds provided herein may be prepared using General Procedure I. In one embodiment, the compounds provided herein may be prepared using General Procedure J. In one embodiment, the compounds provided herein may be prepared using General Procedure K. In one embodiment, the compounds provided herein may be prepared using General Procedure L. In one embodiment, the compounds provided herein may be prepared using General Procedure M. In one embodiment, the compounds provided herein may be prepared using General Procedure N. In one embodiment, the compounds provided herein may be prepared using General Procedure O. In one embodiment, the compounds provided herein may be prepared using General Procedure P. In one embodiment, the compounds provided herein may be prepared using General Procedure Q. In one embodiment, the compounds provided herein may be prepared using General Procedure R. In one embodiment, the compounds provided herein may be prepared using General Procedure S. In one embodiment, the compounds provided herein may be prepared using General Procedure T. In one embodiment, the compounds provided herein may be prepared using General Procedure U. In one embodiment, the compounds provided herein may be prepared using General Procedure V. In one embodiment, the compounds provided herein may be prepared using General Procedure W. In one embodiment, the compounds provided herein may be prepared using General Procedure X. In one embodiment, the compounds provided herein may be prepared using General Procedure Y. In one embodiment, the compounds provided herein may be prepared using General Procedure Z.

In certain embodiments, the compounds provided herein are prepared as a mixture of two or more stereoisomers or diastereoisomers. In one embodiment, the stereoisomers or diastereoisomers are separated using techniques known to those skilled in the art, including but not limited to, chiral column chromatography and chiral resolution by forming a salt with a suitable chiral counterion. In certain embodiments, the compounds provided herein are prepared following one or more stereoselective reaction(s). In some embodiment, the compounds provided herein are prepared as a substantially pure stereoisomer.

D. Methods of Use

1. Modulation of PDE Enzyme Activity

In one embodiment, provided herein is a method of binding a compound provided herein to a PDE enzyme, such as, PDE-10, in one embodiment, PDE-10A. The method comprises contacting the PDE enzyme with a compound provided herein. In one embodiment, the binding to PDE enzyme is assessed using an in vitro binding assay, such as those known in the art.

In one embodiment, provided herein is a method of modulating (e.g., inhibiting or augmenting) the activity of a PDE enzyme, such as, PDE-10, in one embodiment, PDE-10A. In one embodiment, provided herein is a method of inhibiting the activity of a PDE enzyme, such as, PDE-10, in one embodiment, PDE-10A. In one embodiment, the method comprises contacting a PDE enzyme, such as PDE-10A, with a compound provided herein, in vitro or in vivo. In one embodiment, the PDE enzyme, such as PDE-10A, is contacted by a compound provided herein by administering to a subject a therapeutically effective amount of the compound provided herein, or a pharmaceutically acceptable salt or stereoisomer thereof. The subject may be a human. In one embodiment, the PDE enzyme is PDE-10. In one embodiment, the PDE enzyme is PDE-10A.

In other embodiments, the compound provided herein inhibits the activity of a PDE enzyme, such as PDE-10A. Inhibition of PDE activity may be measured using assays known in the art. In some embodiments, the activity of the PDE enzyme is inhibited or reduced by about 1%, about 5%, about 10%, about 20%, about 30%, about 40%, about 50%, about 60%, about 70%, about 80%, about 90%, about 95%, about 99% or more than about 99%, as compared with activity without contacting the PDE enzyme with a compound provided herein (e.g., vehicle condition). In one embodiment, the inhibition of enzyme activity is dose dependent. Exemplary assay methods include, but are not limited to, in vitro binding assays and in vitro functional assays. In one embodiment, the functional assay utilizes an appropriate cell-line expressing a desired PDE enzyme, such as PDE-10A. In one embodiment, the functional assay utilizes a PDE enzyme purified following expression using an appropriate recombinant system. In one embodiment, inhibition of PDE enzyme activity may be assessed using a fluorescent assay, e.g., utilizing a Fluorescein-labeled cAMP/cGMP substrate. In one embodiment, the functional assay utilizes synaptosomes isolated from brain tissue of an appropriate organism. In one embodiment, the assay is carried out in vivo and involves treatment of a test subject (e.g., a rodent) with a compound provided herein. In one embodiment, a test subject is treated with a reference compound or vehicle, as positive or negative controls. In one embodiment, the assay is followed by isolation of brain tissue and ex vivo analysis of substrate concentration (e.g., cAMP or cGMP) in the brain tissue. In one embodiment, the assay is followed by isolation of brain microdialysates and ex vivo analysis of substrate concentration (e.g., cAMP or cGMP) in the microdialysates.

In certain embodiments, provided herein are methods of inhibiting the activity of a PDE enzyme, e.g., PDE-10A, in a subject (e.g., human) comprising administering to the subject an effective amount of a compound provided herein. In some embodiments, the activity of PDE enzyme is inhibited by about 1%, about 5%, about 10%, about 20%, about 30%, about 40%, about 50%, about 60%, about 70%, about 80%, about 90%, about 95%, about 99%, or more than about 99%, when measured using an assay described herein elsewhere.

In one embodiment, provided herein is a method of inhibiting a PDE enzyme to increase the concentration of a cyclic nucleotide substrate. In one embodiment, the method includes contacting the cell with a compound provided herein. In one embodiment, the cell is a brain cell, such as a medium spiny neuron. In one embodiment, the enzyme inhibition occurs in vitro. In one embodiment, the enzyme inhibition occurs in vivo. Thus, in certain embodiments, provided herein are methods of increasing the level of a cyclic nucleotide substrate (e.g., cAMP or cGMP) comprising administering to a subject (e.g., human) an effective amount of a compound provided herein.

Inhibition of PDE enzyme can be shown, for example, by performing various in vitro functional assays utilizing a cell type which expresses a certain type of PDE enzyme, such as PDE-10A, together with an appropriate labeled cyclic nucleotide substrate. In some embodiments, the compounds provided herein inhibit the PDE enzyme in a dose-dependent manner, with an $EC_{50}$ of, for example, between about 0.1 nM and about 10 nM, between about 1 nM and about 1 µM, between about 1 nM and about 500 nM, and between about 1 nM and about 100 nM, in a functional PDE inhibition assay, such as those described herein. In one embodiment, the $EC_{50}$ is less than about 0.01 nM, less than about 0.1 nM, less than about 1 nM, less than about 3 nM, less than about 10 nM, less than about 30 nM, less than about 100 nM, less than about 300 nM, less than about 1000 nM, less than about 3000 nM, or less than about 10000 nM. In one embodiment, the $EC_{50}$ is about 0.01 nM, about 0.1 nM, about 1 nM, about 3 nM, about 10 nM, about 30 nM, about 100 nM, about 300 nM, about 1000 nM, about 3000 nM, or about 10000 nM.

2. Treatment, Prevention, and/or Management of Disorders

In one embodiment, provided herein is a method for the treatment, prevention, and/or management of various disorders, including a disorder of the central nervous system, comprising administering a compound or a composition provided herein. In one embodiment, provided herein is a method for the treatment, prevention, and/or amelioration of one or more symptoms of a disorder (e.g., a CNS disorder), comprising administering a compound or a composition provided herein. In one embodiment, the disorders provided herein include, but are not limited to, schizophrenia, psychosis, cognitive disorders, mood disorders, depression, attention deficit disorders, and neurodegenerative diseases. In one embodiment, the disorders include, but are not limited to, neurological disorder, schizophrenia, schizophrenia-related disorders, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia. In one embodiment, the disorder provided herein is a disorder known in the art that affects the central nervous system (i.e., a CNS disorder).

In one embodiment, provided herein is a method of administering a compound provided herein in a disease model that is known in the art. In one embodiment, the disease model is an animal model. In one embodiment, provided herein is a method of administering the compound provided herein in an animal model that is predictive of efficacy in the treatment of certain diseases in a human. The method comprises administering a compound provided herein in a subject. In one embodiment, the method comprises administering to a subject a therapeutically effective amount of a compound provided herein, or a pharmaceutically acceptable salt or stereoisomer thereof. In one embodiment, the method comprises treatment of a test subject (e.g., a mice or rat) with a compound provided herein. In one embodiment, the method comprises treatment of a test subject (e.g., a mice or rat) with a compound provided herein as well as a reference compound. In one embodiment, the in vivo activity of the compound provided herein is dose dependent. In one embodiment, without being limited to a particular theory, the method provided herein comprises administering an effective amount of a compound provided herein to inhibit PDE-10 activity in a subject. In one embodiment, without being limited to a particular theory, the method provided herein comprises administering an effective amount of a compound provided herein to inhibit PDE-10A activity in a subject.

In one embodiment, the compounds provided herein are active in one or more animal models of schizophrenia or psychosis, such as conditioned avoidance responding (CAR), auditory gating (e.g., amphetamine-induced deficit in auditory gating), phencyclidine (PCP)-induced hyperlocomotion, stimulant-induced hyperlocomotion/hyperactivity, PCP-induced hyperactivity, and amphetamine-induced hyperactivity. In one embodiment, the compounds provided herein inhibit exploratory locomotor activity and/or hyperactivity caused by a dopamine releasing agent, such as amphetamine, and/or a NMDA receptor antagonist, such as phencyclidine (PCP). In one embodiment, the compounds provided herein inhibit conditioned avoidance responding. In one embodiment, the compounds provided herein are active in pre-pulse inhibition (PPI) of acoustic startle response model. In one embodiment, the compounds provided herein inhibit spontaneous locomotor activity. In one embodiment, the compounds provided herein improve cognitive function in a treated subject. In one embodiment, the compounds provided herein improve social interaction in a treated subject. In one embodiment, the compounds provided herein improve social cognition in a treated subject. In one embodiment, the compounds provided herein improve executive function in a treated subject. In one embodiment, the compounds provided herein caused reduced Parkinsonian side effects in a treated subject. In one embodiment, the compounds provided herein produce relatively low levels of catalepsy, as compared to other therapeutic agents. In one embodiment, the compounds provided herein provide a neuron-protective effect on neurons, such as medium spiny neurons, in a treated subject. In one embodiment, the compounds provided herein are active in a striatal quinolinic acid lesion model for Huntington's disease. In one embodiment, the compounds provided herein are active in dizocilpine-induced hyperactivity and stereotyped sniffing model for psychosis. In one embodiment, the compounds provided herein inhibit apomorphine-induced climbing. In one embodiment, the compounds provided herein inhibit N-methyl-D-aspartate antagonist-induced deficits in pre-pulse inhibition of acoustic startle response. In one embodiment, the compounds provided herein improve baseline sensory gating. In one embodiment, the compounds provided herein increase sociality in a social approach/social avoidance assay. In one embodiment, the compounds provided herein enhance social odor recognition. In one embodiment, the compounds provided herein improve novel object recognition. In one embodiment, the compounds provided herein are active in a disease model for a disorder provided herein elsewhere, which is known in the art. See, e.g., Grauer et al., Phosphodiesterase 10A Inhibitor Activity in Preclinical Models of the Positive, Cognitive, and Negative Symptoms of Schizophrenia, *Journal of Pharmacology and Experimental Therapeutics,* 2009, 331(2), 574-90; Threlfell et al., Inhibition of Phosphodiesterase 10A Increases the Responsiveness of Striatal Projection Neurons to Cortical Stimulation, *Journal of Pharmacology and Experimental Therapeutics,* 2009, 328(3), 785-95; Schmidt et al., Preclinical Characterization of Selective Phosphodiesterase 10A Inhibitors: A New Therapeutic Approach to the Treatment of Schizophrenia, *Journal of Pharmacology and Experimental Therapeutics,* 2008, 325(2), 681-90.

In one embodiment, provided herein is a method of treating, preventing, and/or managing various disorders, including, but not limited to, a disorder of the central nervous system. In one embodiment, the method comprises administering to a subject (e.g., human) a therapeutically or prophylactically effective amount of a composition or a compound provided herein. In one embodiment, the subject is a human. In one embodiment, the subject is an animal. In one embodiment, the compounds provided herein are highly brain penetrable in the subject. In certain embodiments, the efficacious concentration of the compounds provided herein is less than 10 nM, less than 100 nM, less than 1 µM, less than 10 µM, less than 100 µM, or less than 1 mM. In one embodiment, the compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of efficacy in humans.

In one embodiment, provided herein is a method of treating, preventing, and/or managing a disorder related to a CNS disorder, a neurological disorder, schizophrenia, a schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, a disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesias, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, or hyperglycemia, comprising administering to a subject an effective amount of a compound provided herein. In one embodiment, provided herein is a method of treating, preventing, and/or managing a disorder selected from schizophrenia, cognitive impairment associated with schizophrenia, cognitive impairment, psychosis, depression, and Huntington's disease, comprising administering to a subject an effective amount of a compound provided herein.

In one embodiment, provided herein is a method of treating, preventing, and/or managing a neurological disorder as provided herein elsewhere, such as schizophrenia, psychosis, cognitive impairment, depression, Alzheimer's disease, Parkinson's disease, and attention deficit hyperactivity disorder (ADHD), and the like, comprising administering to a subject an effective amount of a compound provided herein.

In one embodiment, provided herein is a method of treating, preventing, and/or managing schizophrenia or a schizophrenia-related disorder, including but not limited to schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, and psychosis, comprising administering to a subject an effective amount of a compound provided herein. In one embodiment, the compounds provided herein treat, prevent, and/or ameliorate one or more positive symptoms of schizophrenia. In one embodiment, the compounds provided herein treat, prevent, and/or ameliorate one or more negative symptoms of schizophrenia. In one embodiment, the compounds provided herein treat, prevent, and/or ameliorate one or more cognitive symptoms of schizophrenia.

In one embodiment, provided herein is a method of treating, preventing, and/or managing a disease having a psychosis component, including but not limited to psychotic disorder, brief psychotic disorder, Alzheimer's psychosis, Parkinson's psychosis, shared psychotic disorder, substance-induced psychotic disorder (e.g., cocaine, alcohol, or amphetamine), psychotic disorder due to a general medical condition, psychoaffective disorder, aggression, delirium, excitative psychosis, Tourette's syndrome, manic disorder, organic psychosis, and NOS psychosis, comprising administering to a subject an effective amount of a compound provided herein.

In one embodiment, provided herein is a method of treating, preventing, and/or managing cognitive impairment, including but not limited to cognitive impairment associated with schizophrenia, cognitive deficit in Alzheimer's disease, cognitive deficit in Parkinson's disease, comprising administering to a subject an effective amount of a compound provided herein.

In one embodiment, provided herein is a method of treating, preventing, and/or managing mood disorder, bipolar disorder, anxiety, depression, major depressive disorder, unipolar depression, treatment resistant depression, dysthymia, affective disorder, seasonal affective disorder, or obsessive-compulsive disorder, comprising administering to a subject an effective amount of a compound provided herein.

In one embodiment, provided herein is a method of treating, preventing, and/or managing attention deficit disorder (ADD) or attention deficit hyperactivity disorder (ADHD), comprising administering to a subject an effective amount of a compound provided herein.

In one embodiment, provided herein is a method of treating, preventing, and/or managing a neurodegenerative disease, including but not limited to Huntington's disease, Alzheimer's disease, and Parkinson's disease, comprising administering to a subject an effective amount of a compound provided herein. In one embodiment, provided herein is a method of treating, preventing, and/or managing Huntington's disease, comprising administering to a subject an effective amount of a compound provided herein.

In one embodiment, provided herein is a method of treating, preventing, and/or managing agitation, posttraumatic stress disorder, or behavior disorder, comprising administering to a subject an effective amount of a compound provided herein.

In one embodiment, provided herein is a method of treating, preventing, and/or managing dementia, comprising administering to a subject an effective amount of a compound provided herein.

In one embodiment, provided herein is a method of treating, preventing, and/or managing vertigo, comprising administering to a subject an effective amount of a compound provided herein.

In one embodiment, provided herein is a method of treating, preventing, and/or managing pain, neuropathic pain, sensitization accompanying neuropathic pain, inflammatory pain, migraine or fibromyalgia, comprising administering to a subject an effective amount of a compound provided herein.

In one embodiment, provided herein is a method of treating, preventing, and/or managing movement disorder or restless leg syndrome (RLS), comprising administering to a subject an effective amount of a compound provided herein.

In one embodiment, provided herein is a method of treating, preventing, and/or managing multiple sclerosis, sleep disorder, substance abuse or dependency (e.g., nicotine, cocaine), addiction, eating disorder, or autism, comprising administering to a subject an effective amount of a compound provided herein.

In one embodiment, provided herein is a method of treating, preventing, and/or managing a disorder related to cognitive impairments, such as those associated with Alzheimer's disease, Parkinson's disease, schizophrenia, and attention deficit hyperactivity disorder (ADHD), and the like, comprising administering to a subject an effective amount of a compound provided herein. For example, without being limited by a particular theory, the compounds provided herein may have pro-cognitive effects, such as passive avoidance, novel object recognition, social recognition, and attention-set shifting. Further, without being limited by a particular theory, the compounds provided herein may improve social memory, increase the acquisition of an environment, and reverse scopolamine-induced deficits. The compounds provided herein may also reverse scopolamine-induced deficits in a passive avoidance memory test.

In one embodiment, provided herein is a method of treating, preventing, and/or managing a psychotic disorder or psychotic condition, including but not limited to, schizophrenia, delusional disorders and drug induced psychosis, comprising administering to a subject an effective amount of a compound provided herein.

In one embodiment, provided herein is a method of treating, preventing, and/or managing an anxiety disorder, including but not limited to, panic and obsessive-compulsive disorder, comprising administering to a subject an effective amount of a compound provided herein.

In one embodiment, provided herein is a method of treating, preventing, and/or managing a movement disorder, including but not limited to, Parkinson's disease and Huntington's disease, comprising administering to a subject an effective amount of a compound provided herein.

In one embodiment, the psychotic disorders provided herein that can be treated, prevented, and/or managed using a compound or a pharmaceutical composition provided herein include, but are not limited to, schizophrenia, e.g., of the paranoid, disorganized, catatonic, undifferentiated, and/or residual type; schizophreniform disorder; schizoaffective disorder, e.g., of the delusional and/or depressive type; delusional disorder; substance-induced psychotic disorder, e.g., psychosis induced by alcohol, amphetamine, cannabis, cocaine, hallucinogens, inhalants, opioids, and/or phencyclidine; personality disorder of the paranoid type; and personality disorder of the schizoid type.

In one embodiment, the movement disorders provided herein that can be treated, prevented, and/or managed using a compound or a pharmaceutical composition provided herein include, but are not limited to, Huntington's disease, dyskinesia associated with dopamine agonist therapy, Parkinson's disease, restless leg syndrome, and essential tremor.

In one embodiment, other disorders provided herein that can be treated, prevented, and/or managed using a compound or a pharmaceutical composition provided herein include, but are not limited to, obsessive-compulsive disorder, Tourette's syndrome, and tic disorders.

In one embodiment, provided herein is a method of treating, preventing, and/or managing an anxiety disorder, including but not limited to, panic disorder, agoraphobia, specific phobia, social phobia, obsessive-compulsive disorder, post-traumatic stress disorder, acute stress disorder, and generalized anxiety disorder, comprising administering to a subject an effective amount of a compound provided herein.

In one embodiment, provided herein is a method of treating, preventing, and/or managing a drug addiction, including but not limited to, an alcohol, amphetamine, cocaine, and/or opiate addiction, comprising administering to a subject an effective amount of a compound provided herein. In one embodiment, the drug addiction provided herein represents an abnormal desire for a drug and is generally characterized by motivational disturbances such a compulsion to take the desired drug and episodes of intense drug craving.

In one embodiment, provided herein is a method of treating, preventing, and/or managing a disorder comprising a symptom of deficiency in attention and/or cognition, comprising administering to a subject an effective amount of a compound provided herein. In one embodiment, deficiency in attention and/or cognition provided herein may represent a subnormal functioning in one or more cognitive aspects, such as, e.g., memory, intellect, learning ability, and/or logic ability, in a particular subject relative to other subjects within the same general population and/or age group. In one embodiment, deficiency in attention and/or cognition provided herein may represent a reduction in a particular sub-population's functioning in one or more cognitive aspects, such as, e.g., in age-related cognitive decline.

In one embodiment, the disorders comprising a symptom of deficiency in attention and/or cognition provided herein that can be treated, prevented, and/or managed with a compound or a pharmaceutical composition provided herein, include, but are not limited to, dementia, e.g., dementia in Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, or AIDS-related dementia; delirium; amnestic disorder; post-traumatic stress disorder; mental retardation; learning disorder, e.g., reading disorder, mathematics disorder, or a disorder of written expression; attention-deficit/hyperactivity disorder; and age-related cognitive decline.

In one embodiment, provided herein is a method of treating, preventing, and/or managing a mood disorder or a mood episode, comprising administering to a subject an effective amount of a compound provided herein. In one embodiment, the mood disorders or mood episodes provided herein that can be treated, prevented, and/or managed with a compound or a pharmaceutical composition provided herein include, but are not limited to, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, e.g., bipolar I disorder, bipolar II disorder, and cyclothymic disorder.

In one embodiment, provided herein is a method of treating, preventing, and/or managing a neurodegenerative disorder or neurodegenerative condition, comprising administering to a subject an effective amount of a compound provided herein. In one embodiment, the neurodegenerative disorder or neurodegenerative condition provided herein that can be treated, prevented, and/or managed with a compound or a pharmaceutical composition provided herein represents a disorder or condition that is caused by the dysfunction and/or death of neurons in the central nervous system. The treatment of these disorders and conditions can be facilitated by administration of an agent which prevents the dysfunction or death of neurons at risk and/or enhances the function of damaged or healthy neurons to compensate for the loss of function caused by the dysfunction or death of at-risk neurons. In one embodiment, the neurodegenerative disorders or neurodegenerative conditions provided herein that can be treated, prevented, and/or managed with a compound or a pharmaceutical composition provided herein include, but are not limited to, Parkinson's disease; Huntington's disease; dementia, e.g., Alzheimer's disease, multi-infarct dementia, AIDS-related dementia, and Fronto temporal dementia; neurodegeneration associated with cerebral trauma; neurodegeneration associated with stroke; neurodegeneration associated with cerebral infarct; hypoglycemia-induced neurodegeneration; neurodegeneration associated with neurotoxin poisoning; and multi-system atrophy. In one embodiment, the neurodegenerative disorders or neurodegenerative conditions provided herein comprise neurodegeneration of striatal medium spiny neurons in a subject. In one embodiment, the neurodegenerative disorder or neurodegenerative condition is Huntington's disease.

In one embodiment, provided herein is a method of treating, preventing, and/or managing psychotic disorder, delusional disorder, drug induced psychosis, anxiety disorder, movement disorder, mood disorder, neurodegenerative disorder, or drug addiction, comprising administering to a subject an effective amount of a compound provided herein.

In one embodiment, provided herein is a method of treating, preventing, and/or managing a neurologic disorder, including but not limited to, dementia, Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, AIDS-related dementia, delirium, amnestic disorder, post-traumatic stress disorder, mental retardation, learning disorder, reading disorder, mathematics disorder, disorder of written expression, attention-deficit-hyperactivity disorder, age-related cognitive decline, major depressive episode of the mild, moderate or severe type, manic or mixed mood episode, hypomanic mood episode, depressive episode with atypical features, depressive episode with melancholic features, depressive episode with catatonic features, mood episode with postpartum onset, post-stroke depression, major depressive disorder, dysthymic disorder, minor depressive disorder, premenstrual dysphoric disorder, post-psychotic depressive disorder of schizophrenia, a major depressive disorder superimposed on a psychotic disorder comprising a delusional disorder or schizophrenia, bipolar disorder, bipolar I disorder, bipolar II disorder, cyclothytnic disorder, Parkinson's disease, Huntington's disease, dementia, Alzheimer's disease, multi-infarct dementia, AIDS-related dementia, Fronto temporal dementia, neurodegeneration associated with cerebral trauma, neurodegeneration associated with stroke, neurodegeneration associated with cerebral infarct, hypoglycemia-induced neurodegeneration, neurodegeneration associated with neurotoxin poisoning, multi-system atrophy, schizophrenia of a paranoid, disorganized, catatonic, undifferentiated or residual type, schizophreniform disorder; schizoaffective disorder of the delusional type or the depressive type, delusional disorder, substance-induced psychotic disorder, psychosis induced by alcohol, amphetamine, cannabis, cocaine, hallucinogens, inhalants, opioids, or phencyclidine, personality disorder of the paranoid type, and personality disorder of the schizoid type, comprising administering to a subject an effective amount of a compound provided herein.

In one embodiment, provided herein is a method of treating, preventing, and/or managing a neurologic disorder, including but not limited to, psychotic disorders, delusional disorders, drug induced psychosis, anxiety disorders, movement disorders, mood disorders, neurodegenerative disorders, and drug addiction, comprising administering to a subject an effective amount of a compound provided herein.

In one embodiment, provided herein is a method of treating, preventing, and/or managing substance abuse, comprising administering to a subject an effective amount of a compound provided herein. For example, without being limited by a particular theory, the compounds provided herein may alter methamphetamine self-administration in rats, and therefore the compounds provided herein may ameliorate the craving for addictive drugs.

In one embodiment, provided herein is a method of using the compounds provided herein as psycho-stimulants, which may lack the abuse liabilities generally associated with other classes of psycho-stimulants.

In one embodiment, provided herein is a method of treating, preventing, and/or managing movement disorders, such as Parkinson's disease, L-dopa induced dyskineasias, peak dose dyskinesas, restless leg syndrome (RLS), and Huntington's disease, comprising administering to a subject an effective amount of a compound provided herein.

In some embodiments, the compounds provided herein are active in at least one model, which can be used to measure the activity of the compounds and estimate their efficacy in treating a CNS disorder. For example, the compounds provided herein are active in at least one model for schizophrenia, such as, e.g., conditioned avoidance responding, amphetamine-induced deficit in auditory gating, phencyclidine-induced hyperlocomotion or hyperactivity, and amphetamine-induced hyperactivity models. The compounds are active when they induce a desired response in the animal (e.g., mice) by a statistically significant amount compared to vehicle-treated animals.

In other embodiments, provided herein is a method of effecting a therapeutic effect as described herein elsewhere. The method comprises administering to a subject (e.g., a mammal) a therapeutically effective amount of a compound or a composition provided herein. The particular therapeutic effects may be measured using any model system known in the art and described herein, such as those involving an animal model of a disease.

In some embodiments, the neurological disorder provided herein is: depression (e.g., major depressive disorder, bipolar disorder, unipolar disorder, treatment resistant depression, dysthymia, and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, lowering of attention, speech disorders, autism, and hyperkinetic syndrome.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity, overweight, metabolic syndrome, diabetes, non-insulin dependent diabetes, impaired glucose tolerance, and hyperglycemia.

In one embodiment, the neurological disorder is excessive daytime sleepiness. In another embodiment, the neurological disorder is cognitive impairment. In another embodiment, the neurological disorder is mood disorders. In another embodiment, the neurological disorder is movement disorders. In another embodiment, the neurological disorder is schizophrenia. In another embodiment, the neurological disorder is attention disorders. In another embodiment, the neurological disorder is anxiety disorder. In another embodiment, the neurological disorder is seizure. In another embodiment, the neurological disorder is psychosis. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the compounds described herein treat, prevent, and/or manage a central nervous disorder, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. The dosage may be formulated as a single or multiple unit dosage formulation. In one embodiment, the compound is given in single or divided doses per day.

In some embodiments, the compounds disclosed herein may be used in combination with one or more second active agents to treat, prevent, and/or manage disorders described herein (e.g., administered to a subject need thereof). In certain embodiments, the second active agent is an antipsychotic agent. In certain embodiments, the second active agent is an atypical antipsychotic agent. In certain embodiments, the second active agent is an agent that is useful for the treatment of Alzheimer's disease. In certain embodiments, the second active agent is a cholinesterase inhibitor. In certain embodiments, the second active agent is an antidepressant agent. In certain embodiments, the second active agent is selected from an SSRI, SNRI, and tricyclic antidepressants. In certain embodiments, the second active agent is lurasidone, olanzapine, risperidone, aripiprazole, amisulpride, asenapine, blonanserin, clozapine, clotiapine, illoperidone, mosapratnine, paliperidone, quetiapine, remoxipride, sertindole, sulpiride, ziprasidone, zotepine, pimavanserin, loxapine, donepezil, rivastigmine, memantine, galantamine, tacrine, amphetamine, methylphenidate, atomoxetine, modafinil, sertraline, fluoxetine, venlafaxine, duloxetine, or L-DOPA.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients (e.g., a second active agent provided herein elsewhere). Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising, active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In other embodiments, dosage forms comprise the second active ingredient. The specific amount of the second active agent will depend on the specific agent used, the diseases or disorders being treated or managed, and the amount(s) of a compound provided herein, and any optional additional active agents concurrently administered to the patient.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy*, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

VI. EXAMPLES

Certain embodiments are illustrated by the following non-limiting examples.

A. General Procedures for Compound Synthesis

In the examples below, unless otherwise indicated, all temperatures are set forth in degrees Celsius and all parts and percentages are by weight. Reagents may be purchased from commercial suppliers, such as Sigma-Aldrich® Chemical Company, and may be used without further purification unless otherwise indicated. Reagents may also be prepared following standard literature procedures known to those skilled in the art. Solvents may be purchased from Aldrich in Sure-Seal® bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates and eluted with appropriate solvent ratios (v/v). Reactions were assayed by TLC or liquid chromatography mass spectroscopy (LCMS), and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (see, e.g., Still et al., *J. Org. Chem.*, 43: 2923 (1978)) was performed using silica gel 60 or various medium-pressure liquid chromatography (MPLC) systems (such as Biotage® or ISCO® separation systems).

The compound structures in the examples below were confirmed by one or more of the following methods: proton magnetic resonance spectroscopy, mass spectroscopy, elemental microanalysis, and melting point. Proton nuclear magnetic resonance ($^1H$ NMR) spectra were determined using a NMR spectrometer operating at a certain field strength. Chemical shifts are reported in parts per million (ppm, δ) downfield from an internal standard, such as tetramethylsilane (TMS). Alternatively, $^1H$ NMR spectra were referenced to signals from residual protons in deuterated solvents as follows: $CDCl_3$=7.25 ppm; $DMSO-d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

1. General Procedure A

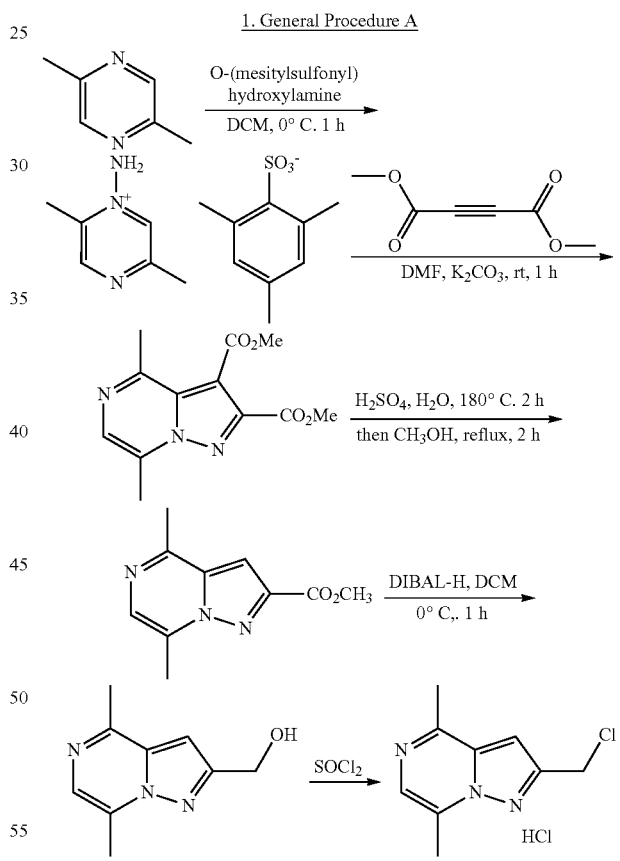

a. 1-Amino-2,5-dimethylpyrazin-1-ium-2,4,6-trimethylbenzenesulfonate

A solution of 2,5-dimethylpyrazine (3.24 g, 30.0 mmol) in dichloromethane (DCM) (30 mL) was cooled to 0° C. A solution of O-(mesitylsulfonyl)hydroxylamine (12.9 g, 60.0 mmol) in DCM (30 mL) was added. The mixture was stirred at 0° C. for 1 h. Then diethyl ether ($Et_2O$) (150 mL) was added. The precipitate was filtered and collected to give 9.42 g (97% yield) of the title compound as a white solid. ESI MS: m/z 124.1 [M+H]+.

b. Dimethyl 4,7-dimethylpyrazolo[1,5-a]pyrazine-2,3-dicarboxylate

To a solution of 1-amino-2,5-dimethylpyrazin-1-ium-2,4,6-trimethylbenzene-sulfonate (4.72 g, 14.6 mmol) in N,N-dimethylformamide (DMF) (50 mL) was added potassium carbonate (4.44 g, 32.1 mmol). The mixture was stirred at room temperature for 10 min. Then a solution of dimethyl but-2-ynedioate (1.87 g, 13.2 mmol) in DMF (30 mL) was added. The resulting mixture was stirred at room temperature for 1 h. Then the mixture was poured into water (400 mL), extracted with EtOAc (3×200 mL). The combined organic layer was dried over sodium sulfate, filtered, evaporated, and chromatographed on silica gel using 20% ethyl acetate (EtOAc) in petroleum ether (PE) as eluent to give 1.04 g (27% yield) of the title compound as a yellow solid. ESI MS: m/z 124.1 [M+H]+. 1H NMR (400 MHz, CDCl3) δ 7.82 (d, J=0.8 Hz, 1H), 4.03 (s, 3H), 4.00 (s, 3H), 2.81 (s, 3H), 2.75 (s, 3H).

c. Methyl 4,7-dimethylpyrazolo[1,5-a]pyrazine-2-carboxylate

A solution of dimethyl 4,7-dimethylpyrazolo[1,5-a]pyrazine-2,3-dicarboxylate (900 mg, 3.42 mmol) in sulfuric acid (4 mL) and water (1 mL) was stirred and heated to 180° C. After stirring for 2 h at that temperature, the reaction mixture was cooled, and 40 mL of methanol (MeOH) was added. The mixture was refluxed at 70° C. for 2 h. Then the mixture was concentrated to dryness. The residue was treated with water and adjusted with saturated sodium bicarbonate solution to pH 8, then extracted with EtOAc (3×100 mL). The combined organic layer was washed with brine, dried over sodium sulfate, filtered, and evaporated to give 560 mg (80% yield) of the title compound as a yellow solid. ESI MS: m/z 206.1 [M+H]+. 1H NMR (400 MHz, CDCl3) δ 7.73 (d, J=0.8 Hz, 1H), 7.36 (s, 1H), 4.03 (s, 3H), 2.77 (s, 3H), 2.75 (s, 3H).

d. (4,7-Dimethylpyrazolo[1,5-a]pyrazin-2-yl)methanol

A solution of methyl 4,7-dimethylpyrazolo[1,5-a]pyrazine-2-carboxylate (62 mg, 0.30 mmol) in DCM (5 mL) was cooled to 0° C. Diisobutylaluminium hydride (DIBAL-H) (1 M in cyclohexane, 1 mL, 0.33 mmol) was added to the above solution dropwise over 5 min. After addition, the mixture was stirred at 0° C. for 1 h. Saturated aqueous ammonium chloride solution (2 mL) was added to quench the reaction. Then 5 mL of saturated sodium bicarbonate aqueous solution was added. The mixture was extracted with DCM (3×15 mL). The combined organic layer was washed with brine, dried over sodium sulfate, filtered, evaporated, and chromatographed on silica gel using 5% MeOH in DCM as eluent to give 41 mg (77% yield) of the title compound as a yellow solid. ESI MS: m/z 178.1 [M+H]+. 1H NMR (400 MHz, CDCl3) δ 7.60 (s, 1H), 6.77 (s, 1H), 4.98 (d, J=6.0 Hz, 2H), 2.71 (s, 3H), 2.67 (s, 3H).

e. 2-(Chloromethyl)-4,7-dimethylpyrazolo[1,5-a]pyrazine hydrochloride

A solution of (4,7-dimethylpyrazolo[1,5-a]pyrazin-2-yl) methanol (41 mg, 0.23 mmol) in thionyl chloride (2 mL) was stirred at room temperature for 5 min. The mixture was concentrated to dryness to give 53 mg (100% yield) of the title compound as a yellow solid. ESI MS: m/z 196.1 [M+H]+.

2. General Procedure B

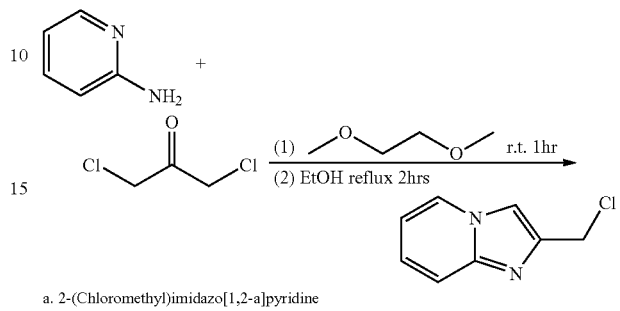

a. 2-(Chloromethyl)imidazo[1,2-a]pyridine

To a solution of 1,3-dichloropropan-2-one (1.40 g, 11 mmol) in 1,2-dimethoxyethane (5 mL), pyridin-2-amine (0.94 g 10 mmol) was added. The solid dissolved immediately and a white precipitate was observed. The mixture was stirred at room temperature for 1 h, and then was cooled to 0° C. for 20 min. The resulting mixture was filtered to give a white solid. The precipitate was suspended in ethanol (EtOH) (40 mL) and heated at reflux to render a clear solution. After refluxing for 2 h, the reaction mixture was concentrated under reduced pressure. The residue was dissolved in water and saturated aqueous NaHCO3 solution was added to adjust the pH to ~7.0. A white suspension formed during the course of addition. The resulting mixture was stirred for 20 min and then filtered to give the title compound as a white solid (0.5 g, 30% yield). ESI MS: m/z 167 [M+H]+. 1H NMR (400 MHz, DMSO-d6) δ 8.49 (d, J=6.8 Hz, 1H), 7.97 (s, 1H), 7.49 (d, J=8.8 Hz, 1H), 7.23 (t, J=7.6 Hz, 1H), 6.88 (t, J=6.4 Hz, 1H), 4.82 (s, 2H).

3. General Procedure C

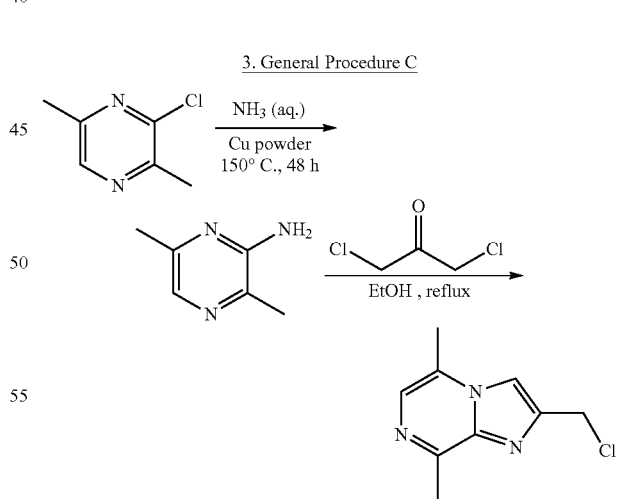

a. 3,6-Dimethylpyrazin-2-amine

A 100 mL autoclave vessel was charged with 3-chloro-2,5-dimethylpyrazine (25.0 g, 176 mmol), NH3 (aq. 25~28% w/w, 80 mL) and Cu powder (1.69 g, 26.4 mmol) and the autoclave vessel was sealed. The resulting mixture was heated to 150° C. and stirred vigorously for 48 h. The reaction mixture was cooled to room temperature and concentrated under reduced pressure. The residue was diluted with brine (100 mL) and extracted with EtOAc (4×100 mL). The combined extracts were dried over $Na_2SO_4$, filtered, and concentrated under reduced pressure. The residue was washed with PE to render the title compound as a light yellow solid (17.6 g, yield 81%). ESI MS: m/z 124 [M+H]$^+$.

b. 2-(Chloromethyl)-5,8-dimethylimidazo[1,2-a] pyrazine

To a solution of 3,6-dimethylpyrazin-2-amine (1.0 g, 8.1 mmol) in EtOH (20 mL) was added 1,3-dichloropropan-2-one (1.03 g, 8.1 mmol). The reaction mixture was stirred at reflux for 1 h. Then the solvent was removed. The product was purified by reverse column chromatography to give the title compound as a brown solid (570 mg, yield 85%). ESI MS: m/z 196 [M+H]$^+$. $^1$H NMR (400 MHz, DMSO-d$_6$): δ 8.10 (s, 1H), 7.65 (s, 1H), 4.94 (s, 2H), 2.70 (s, 3H), 2.54 (s, 3H).

4. General Procedure D

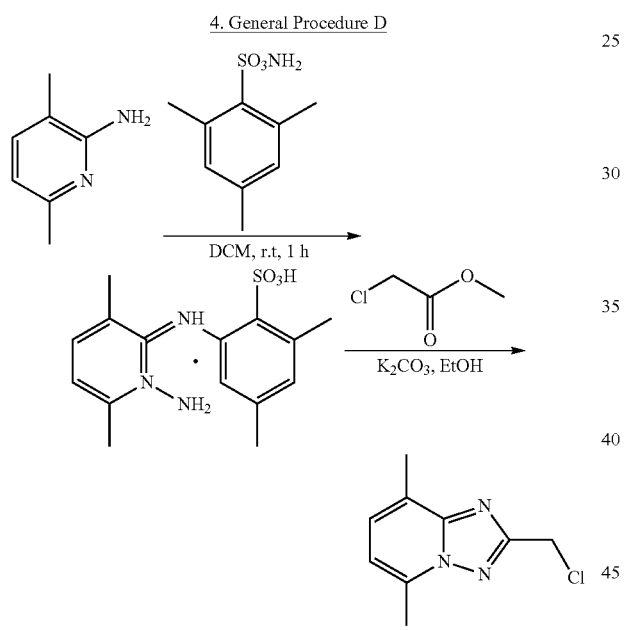

a. 1-Amino-3,6-dimethylpyridin-2(1H)-iminium-2,4,6-trimethylbenzenesulfonate

A solution of O-(mesitylsulfonyl)hydroxylamine (5.3 g, 24.6 mmol) in DCM (20 mL) was slowly added to a solution of 3,6-dimethylpyridin-2-amine (1.0 g, 8.2 mmol) in DCM (5 mL). A yellow precipitate was formed gradually, and after stirring for 1 h, the precipitate was collected by filtration and used for the next step without further purification. ESI MS: m/z 138 [M+H]$^+$.

b. 2-(Chloromethyl)-5,8-dimethyl[1,2,4]triazolo[1,5-a]pyridine

A suspension of 1-amino-3,6-dimethylpyridin-2(1H)-iminium-2,4,6-trimethyl-benzenesulfonate (crude product from the previous step, 8.2 mmol), methyl 2-chloroacetate (1.78 g, 16.4 mmol) and potassium carbonate (2.26 g, 16.4 mmol) in EtOH (30 mL) was stirred at 80° C. for 16 h. After cooled to room temperature, the reaction mixture was concentrated and the residue was purified by silica gel column chromatography (eluting with 20% v/v EtOAc in PE) to give the title compound (920 mg, yield 36%, 2 steps). ESI MS: m/z 196, 198 [M+H]$^+$. $^1$H NMR (400 MHz, CDCl$_3$): δ 7.24 (d, J=7.2 Hz, 1H), 6.77 (d, J=7.2 Hz, 1H), 4.85 (s, 2H), 2.74 (s, 3H), 2.62 (s, 3H).

5. General Prodcedure E

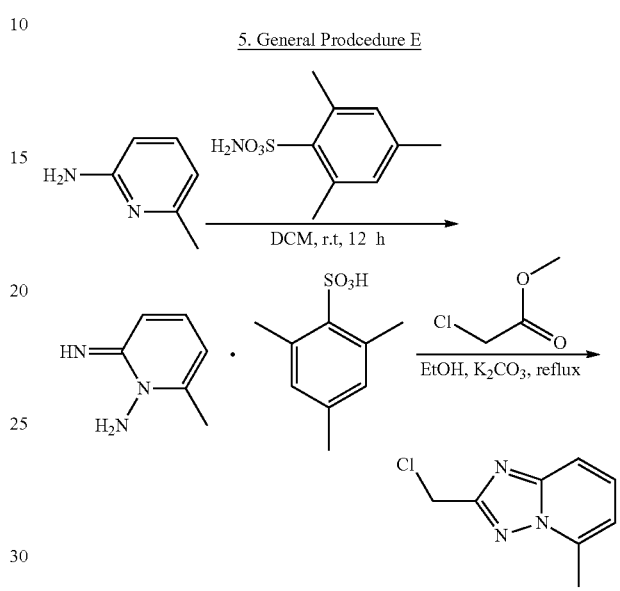

a. 1-Amino-6-methylpyridin-2(1H)-iminium-2,4,6-trimethyl-benzenesulfonate

A solution of O-(mesitylsulfonyl)hydroxylamine (6.45 g, 30.0 mmol) in DCM (30 mL) was stirred at room temperature, then 2-amino-6-methylpyridine (1.08 g, 10.0 mmol) was added slowly. The reaction mixture was stirred at room temperature for 12 h, and filtered to remove the solvent. A yellow solid was collected which was used for the next step without further purification. ESI MS: m/z 124 [M+H]$^+$.

b. 2-(Chloromethyl)-5-methyl-[1,2,4]triazolo[1,5-a]pyridine

A suspension of 1-amino-6-methylpyridin-2(1H)-iminium-2,4,6-trimethyl-benzenesulfonate (520 mg, crude product from the previous step, 1.61 mmol), methyl 2-chloroacetate (700 mg, 7.80 mmol) and potassium carbonate (444 mg, 3.22 mmol) in EtOH (10 mL) was stirred at 80° C. for 16 h. After cooled to room temperature, the reaction mixture was concentrated and purified by silica gel column chromatography (eluting with EtOAc in PE, a gradient from 17% to 30% v/v) to give the title compound (290 mg, yield 84%). ESI MS: m/z 182, 184 [M+H]$^+$.

6. General Prodcedure F

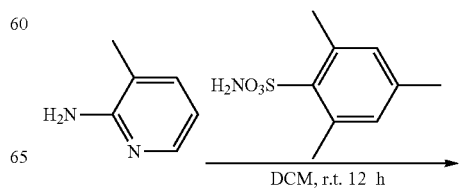

73
-continued

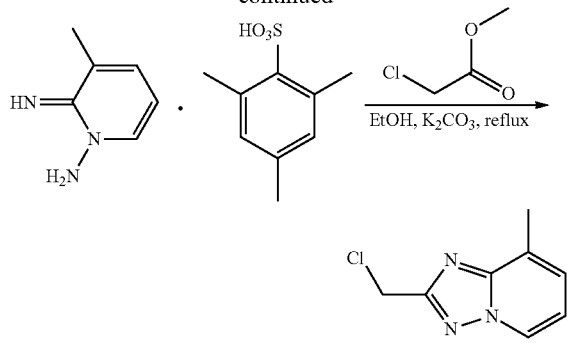

a. 1-Amino-3-methylpyridin-2(1H)-iminium-2,4,6-trimethyl-benzenesulfonate

A solution of O-(mesitylsulfonyl)hydroxylamine (6.45 g, 30.0 mmol) in DCM (30 mL) was stirred at room temperature, then 2-amino-3-methylpyridine (1.08 g, 10.0 mmol) was added slowly. The reaction mixture was stirred at room temperature for 12 h, the solvent was removed under vacuum, and the crude product was used for the next step without further purification. ESI MS: m/z 124 [M+H]$^+$.

b. 2-(Chloromethyl)-8-methyl-[1,2,4]triazolo[1,5-a]pyridine

A suspension of 1-amino-3-methylpyridin-2(1H)-iminium-2,4,6-trimethyl-benzenesulfonate (630 mg, crude product from the previous step, 1.95 mmol), methyl 2-chloroacetate (423 mg, 3.90 mmol) and potassium carbonate (540 mg, 3.9 mmol) in EtOH (10 mL) was stirred at 80° C. for 4 h. After cooled to room temperature, the reaction mixture was concentrated and the residue was purified by silica gel column chromatography (eluting with 25% v/v EtOAc in PE) to give the title compound (95 mg, yield 27%). ESI MS: m/z 182, 184 [M+H]$^+$.

74 a. 1-Aminopyridin-2(1H)-iminium-2,4,6-trimethyl-benzenesulfonate

A mixture of pyridin-2-amine (6.6 g, 20.0 mmol) in DCM (15 mL) was stirred at room temperature, and O-(mesitylsulfonyl)hydroxylamine (1.0 g, 10.0 mmol) was added slowly. The reaction mixture was stirred at room temperature for 12 h, and the solvent was removed under vacuum. The crude product was used for next step without further purification. ESI MS: m/z 110 [M+H]$^+$.

b. 2-(Chloromethyl)-[1,2,4]triazolo[1,5-a]pyridine

A mixture of 1-aminopyridin-2(1H)-iminium-2,4,6-trimethylbenzenesulfonate (crude product from the previous step) and sodium hydroxide (NaOH) (0.55 g, 13.8 mmol) in EtOH (30 mL) was stirred at 60° C. for 1 h, then methyl 2-chloroacetate (1.12 g, 10.4 mmol) was added. The reaction mixture was refluxed for 4 h, then the solvent was removed. The product was purified by silica gel column chromatography (eluting with 20% v/v EtOAc in PE) to give the title compound (512 mg, yield: 29%, 2 steps). ESI MS: m/z 168 [M+H]$^+$.

c. [1,2,4]Triazolo[1,5-a]pyridin-2-ylmethanol

To a solution of 1-aminopyridin-2(1H)-iminium-2,4,6-trimethylbenzenesulfonate (1.24 g, 4 mmol) in EtOH (15 mL) was added NaOH (320 mg, 8 mmol). The mixture was heated to 60° C. and stirred for 1 h. Then methyl 2-hydroxyacetate (720 mg, 8 mmol) was added and the mixture was heated to 80° C. and stirred for 3 h. The resulting mixture was cooled to room temperature and concentrated under reduced pressure. The residue was washed with water (10 mL) and extracted with DCM (15 mL×3). The combined organic layers were washed with brine (10 mL), dried over anhydrous sodium sulfate and concentrated under reduced pressure to afford the title compound as a pale yellow solid (350 mg, 59% yield). ESI MS: m/z 150 [M+H]$^+$.

7. General Procedure G

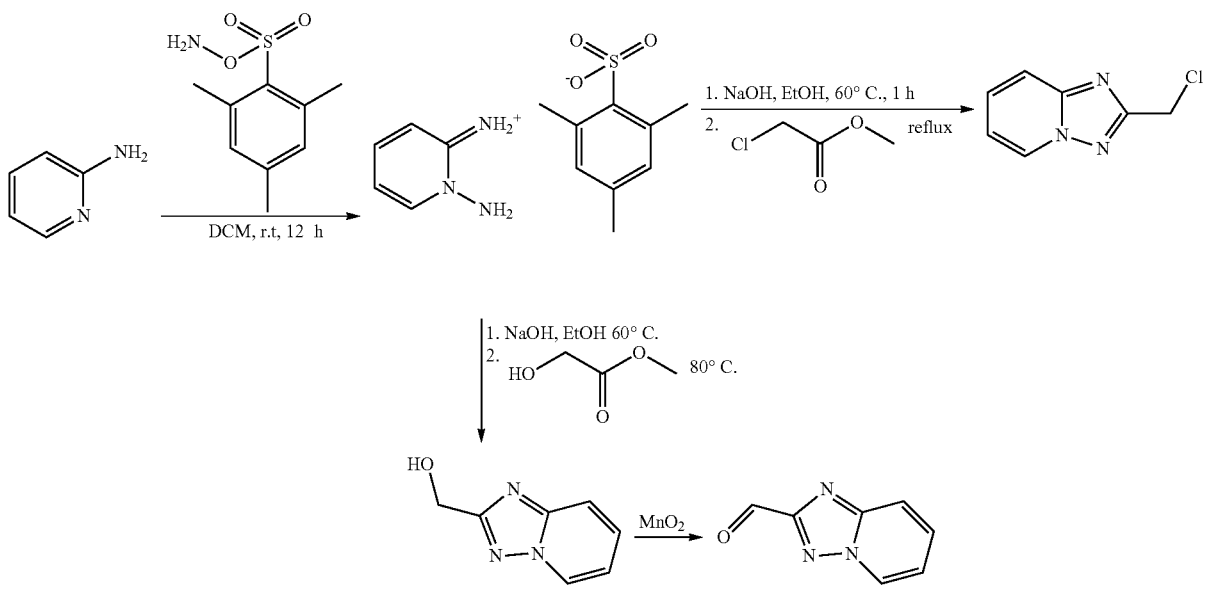

d. [1,2,4]Triazolo[1,5-a]pyridine-2-carbaldehyde

To a solution of [1,2,4]triazolo[1,5-a]pyridin-2-ylmethanol (0.35 g, 2.3 mmol) in EtOH (50 mL) was added manganese (IV) oxide (1.02 g, 11.5 mmol). The mixture was refluxed for 2 days. After cooling to room temperature, the mixture was filtered through Celite. The filtrate was concentrated, and the residue was purified by reverse phase column chromatography (eluting with 10% v/v acetonitrile in water, with 0.01% $NH_3.H_2O$) to afford the title compound (0.15 g, 43% yield) as a white solid. ESI MS: m/z 148 $[M+H]^+$.

8. General Procedure H

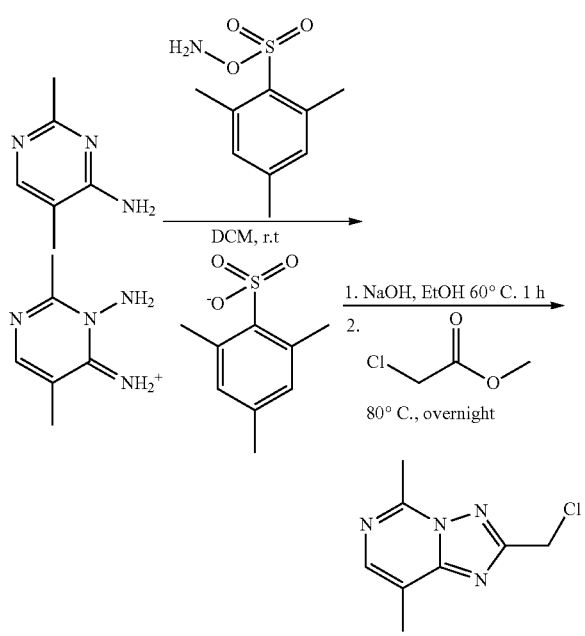

a. 3-Amino-2,5-dimethylpyrimidin-4(3H)-iminium-2,4,6-trimethylbenzenesulfonate A mixture of 2,5-dimethylpyrimidin-4-amine (15.2 g, 49.0 mmol) in DCM (30 mL) was stirred at room temperature, and O-(mesitylsulfonyl)hydroxylamine (2.0 g, 16.0 mmol) was added slowly. The reaction mixture was stirred at room temperature for 12 h, then the solvent was removed under reduced pressure. The crude product was used for the next step without further purification. ESI MS: m/z 139 $[M+H]^+$.

b. 2-(Chloromethyl)-5,8-dimethyl-[1,2,4]triazolo[1,5-f]pyrimidine

A mixture of 3-amino-2,5-dimethylpyrimidin-4(3H)-iminium-2,4,6-trimethylbenzenesulfonate (crude product from the previous step), NaOH (1.33 g, 33.1 mmol) in EtOH (100 mL) was stirred at 60° C. for 1 h, and then methyl 2-chloroacetate (10.8 g, 99.3 mmol) was added. The reaction mixture was stirred and refluxed overnight, and then the solvent was removed under reduced pressure. The product was purified by silica gel column (eluting with 20% v/v EtOAc in PE) to give the title compound (72 mg, yield 2%, 2 steps). ESI MS: m/z 197 $[M+H]^+$.

9. General Procedure I

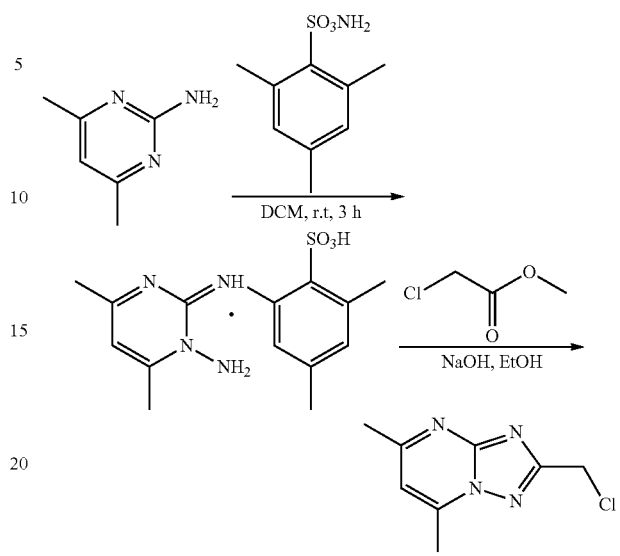

a. 1-Amino-4,6-dimethylpyridin-2(1H)-iminium-2,4,6-trimethyl-benzenesulfonate A solution of O-(mesitylsulfonyl)hydroxylamine (1.65 g, 7.65 mmol) in DCM (20 mL) was stirred at room temperature, and 4,6-dimethylpyrimidine (0.313 g, 2.55 mmol) was added slowly. The reaction mixture was stirred at room temperature for 3 h, then the solvent was removed under reduced pressure, and the crude product was used for the next step without further purification. ESI MS: m/z 139 $[M+H]^+$.

b. 2-(Chloromethyl)-5,7-dimethyl-[1,2,4]triazolo[1,5-a]pyrimidine

A suspension of 1-amino-4,6-dimethylpyridin-2(1H)-iminium-2,4,6-trimethyl-benzenesulfonate (crude product from the previous step, 2.55 mmol), methyl 2-chloroacetate (550 mg, 5.10 mmol) and NaOH (410 mg, 10.20 mmol) in EtOH (10 mL) was stirred at 80° C. for 4 h. After cooled to room temperature, the reaction mixture was concentrated, and the residue was purified by silica gel column chromatography (eluting with 25% v/v EtOAc in PE) to give the title compound (110 mg, yield 22%). ESI MS: m/z 197, 199 $[M+H]^+$.

10. General Procedure J

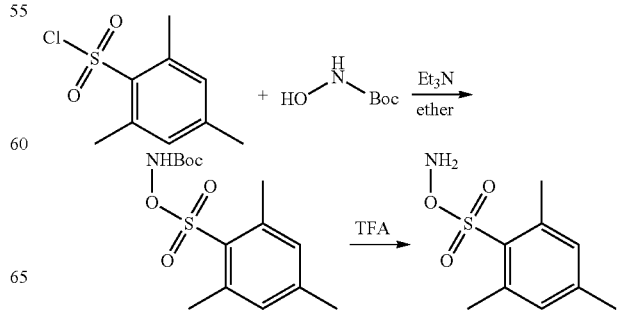

-continued

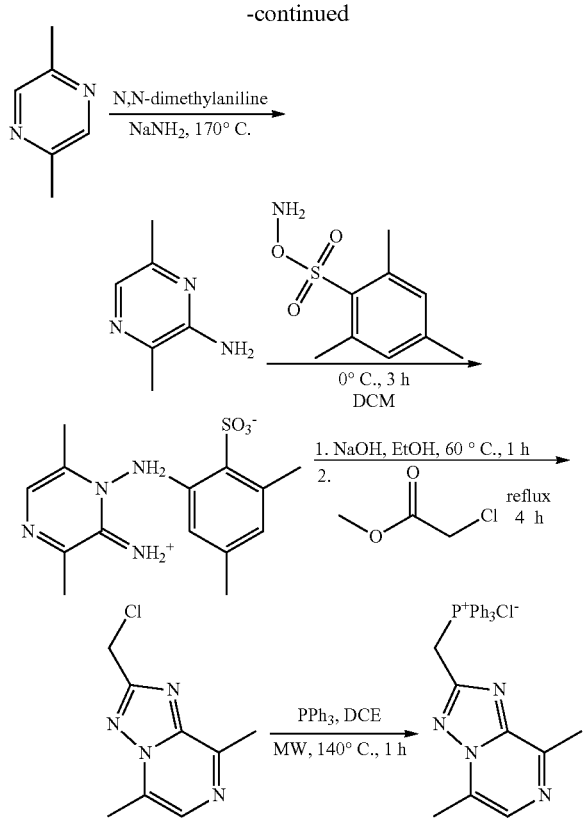

(a) O-(Mesitylsulfonyl)hydroxylamine

To a solution of 2,4,6-trimethylbenzene-1-sulfonyl chloride (30 g, 0.148 mol) and tert-butyl hydroxycarbamate (18 g, 0.148 mol) in Et$_2$O (500 mL) was added Et$_3$N (15 g, 0.148 mol) dropwise over 1 h. The reaction mixture was stirred at room temperature for 4 h, then filtered. The filtrate was concentrated. The product was purified by silica gel column chromatography (5% v/v EtOAc in PE) to give tert-butyl mesitylsulfonyloxycarbamate as a white solid (31 g, yield 72%). ESI MS: m/z 338 [M+Na]$^+$.

A solution of tert-butyl mesitylsulfonyloxycarbamate (3 g, 9.5 mmol) in trifluoroacetic acid (7 mL) was stirred at 10° C. for 40 min, then poured into ice/water (10 mL) and the resulting solid was collected by filtration. The solid was dissolved in DCM (12 mL), dried over Na$_2$SO$_4$, and filtered. The solution containing O-(mesitylsulfonyl)hydroxylamine was used without further purification.

(b) 3,6-Dimethylpyrazin-2-amine

A mixture of 2,5-dimethylpyrazine (14 g, 0.13 mol) in N,N-dimethylaniline (50 mL) was heated to 170° C. and NaNH$_2$ (22 g, 0.56 mol) was added in portions. The reaction mixture was stirred at 170° C. for 1 h, and the solvent was removed. The product was purified by silica gel column chromatography to give 3,6-dimethylpyrazin-2-amine as a brown solid (1.6 g, yield 10%). ESI MS: m/z 124 [M+1]$^+$.

(c) 1-Amino-3,6-dimethylpyrazin-2(1H)-iminium-2, 4,6-trimethylbenzenesulfonate

A mixture of 3,6-dimethylpyrazin-2-amine (1.23 g, 10 mmol) in DCM (20 mL) was cooled to 0° C. and a solution of O-(mesitylsulfonyl)hydroxylamine (4.3 g, 20 mmol) was added slowly. The reaction mixture was allowed to warm to room temperature for 3 h and filtered. The solid collected was washed with DCM (50 mL) to give 1-amino-3,6-dimethylpyrazin-2(1H)-iminium-2,4,6-trimethylbenzenesulfonate as a brown solid (2.0 g, yield 59%). ESI MS: m/z 139 [M+199]$^+$.

(d) 2-(Chloromethyl)-5,8-dimethyl[1,2,4]triazolo[1, 5-a]pyrazine

A mixture of 1-amino-3,6-dimethylpyrazin-2(1H)-iminium-2,4,6-trimethylbenzenesulfonate (2.0 g, 5.9 mmol) and NaOH (480 mg, 12 mmol) in EtOH (20 mL) was stirred at 60° C. for 1 h. Methyl 2-chloroacetate (1.34 g, 12.4 mmol) was then added slowly. The reaction mixture was refluxed for 4 h, then the solvent was removed. The product was purified by silica gel column chromatography to give 2-(chloromethyl)-5,8-dimethyl-[1,2,4]triazolo[1,5-a]pyrazine as a yellow solid (420 mg, yield 36.3%). ESI MS: m/z 197 [M+1]$^+$.

(e) ((5,8-Dimethyl-[1,2,4]triazolo[1,5-a]pyrazin-2-yl)methyl)triphenylphosphonium chloride A mixture of 2-(chloromethyl)-5,8-dimethyl-[1,2,4]triazolo[1,5-a]pyrazine (420 mg, 2.14 mmol) and triphenylphosphine (672 mg, 2.57 mmol) in 1,2-dichloroethane (10 mL) was heated to 140° C. in a microwave reactor for 1 h. The reaction mixture was cooled to room temperature and concentrated to give the title compound as a yellow solid (980 mg, yield 100%). ESI MS: m/z 424 [M−35]$^+$.

11. General Procedure K

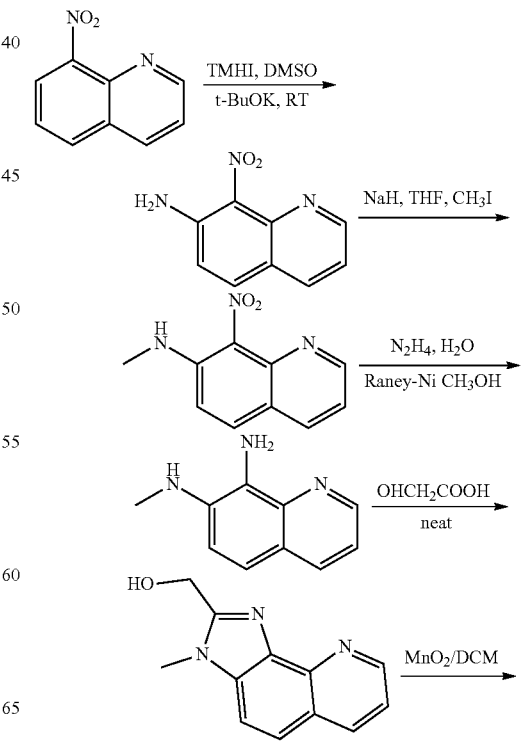

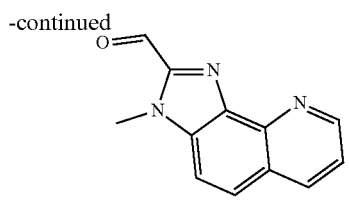

a. 8-Nitroquinolin-7-amine

To a solution of 8-nitroquinoline (1.88 g, 10 mmol) and 1,1,1-trimethylhydrazinium iodide (3.03 g, 15 mmol) in anhydrous dimethyl sulfoxide (DMSO) (20 mL) was added potassium tert-butoxide (3.36 g, 30 mmol) as a solid. The mixture was stirred at room temperature for 1 h. The mixture was then poured into saturated aqueous ammonium chloride and extracted with EtOAc. The organic layers were concentrated and the residue was purified by silica gel column chromatography (eluting with PE/EtOAc v/v 2:1) to give 8-nitroquinolin-7-amine as a yellow solid (300 mg, yield 18%). ESI MS: m/z 189 [M+H]$^+$. $^1$H NMR (400 MHz, CDCl$_3$): δ 8.93 (dd, 1H, $^1$J=3.2 Hz, $^2$J=1.6 Hz), 8.00 (dd, 1H, $^1$J=6.4 Hz, $^2$J=1.6 Hz), 7.69 (d, 1H, J=6.8 Hz), 7.29 (dd, 1H, $^1$J=6.0 Hz, $^2$J=3.2 Hz), 7.00 (d, 1H, J=7.2 Hz), 5.60 (s, 2H).

b. N-Methyl-8-nitroquinolin-7-amine

To a solution of 8-nitroquinolin-7-amine (1.89 g, 10 mmol) in tetrahydrofuran (THF) (10 mL) was added sodium hydride (60% wt in mineral oil, 800 mg, 20 mmol). The mixture was stirred at room temperature for 30 minutes, then iodomethane (1.42 g, 10 mmol) was added. The mixture was stirred at room temperature for 5 h. Then water (10 mL) was added. The mixture was extracted with EtOAc, and the organic layer was concentrated. The residue was purified by silica gel column chromatography (eluting with PE/EtOAc v/v 2:1) to give N-methyl-8-nitroquinolin-7-amine as a yellow solid (1.6 g, yield 79%). ESI MS: m/z 204 [M+H]$^+$.

c. N$^7$-Methylquinoline-7,8-diamine

To a solution of N-methyl-8-nitroquinolin-7-amine (1.6 g, 7.9 mmol) in MeOH (25 mL) was added hydrazine hydrate (2.25 g, 455 mmol) and Raney Ni (8 drops). The mixture was stirred at room temperature for 20 minutes. The catalyst was removed by filtration and the filtrate was concentrated to give N$^7$-methylquinoline-7,8-diamine as a yellow solid (1.2 g, yield 80%). ESI MS: m/z 174 [M+H]$^+$.

d. (3-Methyl-3H-imidazo[4,5-h]quinolin-2-yl)methanol

A mixture of N$^7$-methylquinoline-7,8-diamine (1.0 g, 5.8 mmol) and 2-hydroxy acetic acid (2.2 g, 29 mmol) was stirred at 115° C. for 2 h. Then saturated sodium bicarbonate solution was added. The mixture was extracted with EtOAc. The organic layer was concentrated to give a residue which was purified by silica gel column chromatography (eluting with DCM/MeOH v/v 30:1) to give (3-methyl-3H-imidazo-[4,5-h]quinolin-2-yl)methanol as a yellow solid (1.0 g, yield 83%). ESI MS: m/z 214 [M+H]$^+$.

e. 3-Methyl-3H-imidazo[4,5-h]quinoline-2-carbaldehyde

To a solution of (3-methyl-3H-imidazo[4,5-h]quinolin-2-yl)methanol (560 mg, 2.62 mmol) in DCM (10 mL) was added manganese (IV) oxide (2.28 g, 26.2 mmol). The mixture was stirred at room temperature for 12 h. The solid was removed by filtration and the filtrate was concentrated. The crude product was purified by silica gel column chromatography (eluting with PE/EtOAc v/v 2:1) to give 3-methyl-3H-imidazo[4,5-h]quinoline-2-carbaldehyde as a yellow solid (370 mg, yield: 67.5%). ESI MS: m/z 212 [M+H]$^+$.

f. 3-Methyl-3H-imidazo[4,5-f]quinoline-2-carbaldehyde

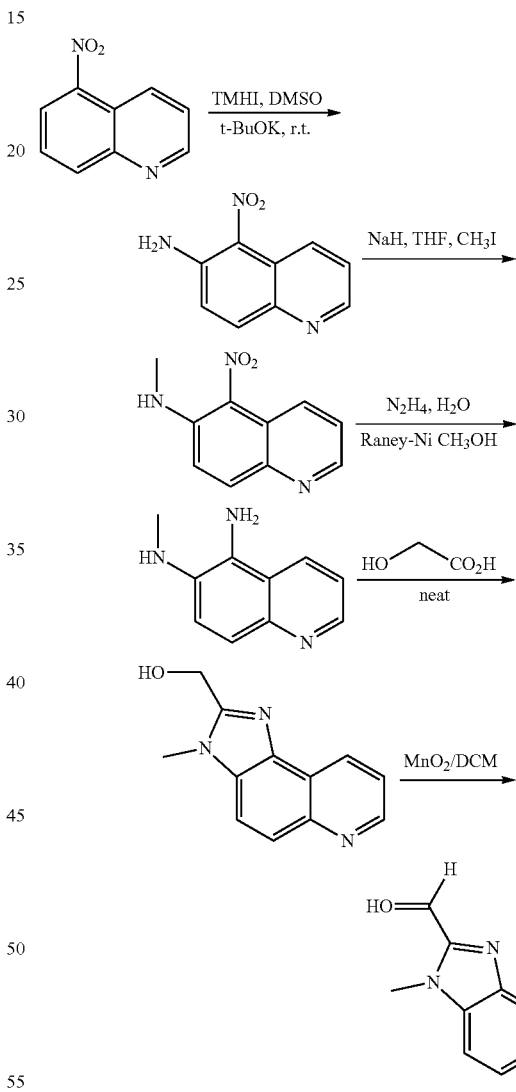

The methyl and desmethyl imidazo[4,5-f]quinoline were prepared using similar chemical procedures of the above steps of General Procedure K (e.g., steps a to e). In the above scheme, the crude aldehyde was purified by column chromatography (eluting with PE/EtOAc v/v 2:1) to give 3-methyl-3H-imidazo[4,5-f]quinoline-2-carbaldehyde as a yellow solid. ESI MS: m/z 212 [M+H]$^+$. $^1$H NMR (400 MHz, CDCl$_3$): δ 10.19 (s, 1H), 9.02-8.99 (m, 1H), 8.99 (s, 1H), 8.17 (d, J=5.2 Hz, 1H), 7.79 (d, J=5.2 Hz, 1H), 7.63 (dd, J=7.8, 4.2 Hz, 1H), 4.30 (s, 3H).

12. General Procedure L

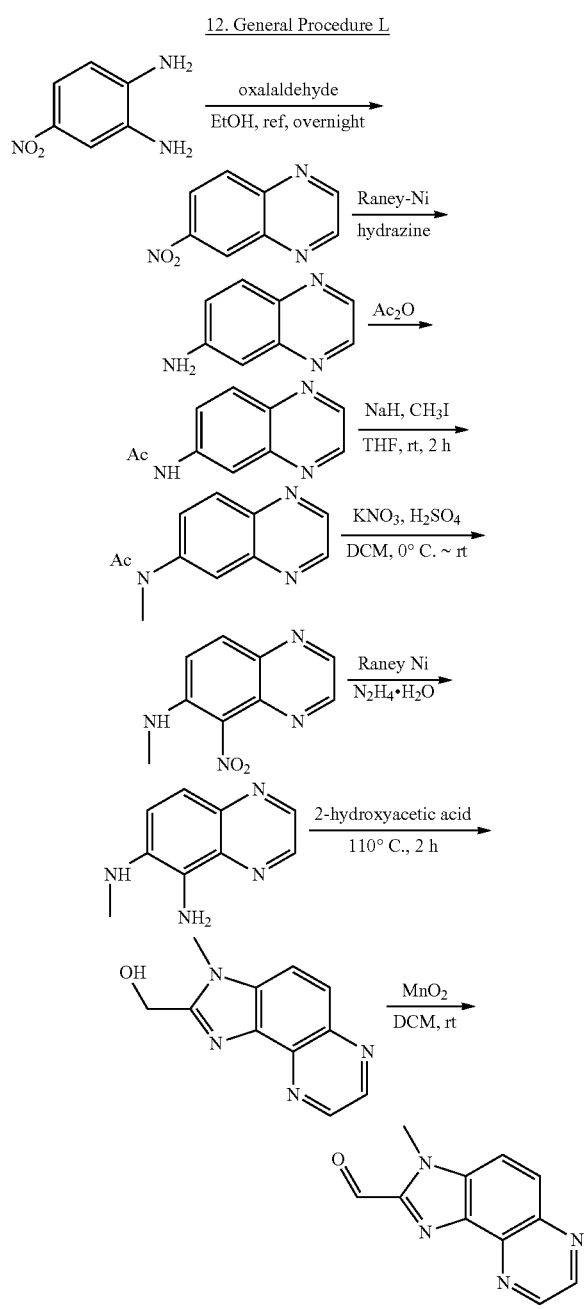

a. 6-Nitroquinoxaline

A suspension of 4-nitrobenzene-1,2-diamine (15.3 g, 0.1 mol) and oxalaldehyde (40% in water, 17.4 g, 0.12 mol) in EtOH (150 mL) was stirred at reflux for 16 h. The mixture was then filtered, and the solid was collected to give 6-nitroquinoxaline as a yellow solid (17.0 g, yield 97%). ESI MS: m/z 176.0 [M+H]$^+$.

b. Quinoxalin-6-amine

To a solution of 6-nitroquinoxaline (17.0 g, 0.097 mol) in MeOH (500 mL) was added hydrazine hydrate (19.4 g, 0.39 mol) and Raney Ni (2.0 g). The mixture was stirred at room temperature for 1 h. The mixture was then filtered, and the filtrate was concentrated under reduce pressure to give quinoxalin-6-amine as a yellow solid (14.0 g, yield 99%). ESI MS: m/z 146.1 [M+H]$^+$.

c. N-(Quinoxalin-6-yl)acetamide

A solution of quinoxalin-6-amine (14.0 g, 0.97 mol) in acetic anhydride (120 mL) was stirred at 100° C. for 1 h. Excess acetic anhydride was removed under reduced pressure. To the residue was added 150 mL of saturated aqueous sodium bicarbonate solution. The mixture was extracted with DCM (3×150 mL), and the combined organic layers were dried over sodium sulfate and concentrated under reduce pressure to give N-(quinoxalin-6-yl)acetamide as a yellow solid (8.4 g, yield 47%). ESI MS: m/z 188.1 [M+H]$^+$.

d. N-Methyl-N-(quinoxalin-6-yl)acetamide

To a solution of N-(quinoxalin-6-yl)acetamide (8.0 g, 0.043 mol) in THF (120 mL) was added sodium hydride (60% wt in mineral oil, 3.42 g, 0.086 mol). The mixture was stirred at room temperature for 10 min. Then iodomethane (7.28 g, 0.051 mol) was added. The mixture was stirred at room temperature for 2 h. Water (60 mL) was added carefully. The mixture was extracted with EtOAc (3×150 mL). The extracts were dried over sodium sulfate, concentrated to give N-methyl-N-(quinoxalin-6-yl)acetamide as a brown solid (8.04 g, yield 93%). ESI MS: m/z 202.1 [M+H]$^+$.

e. N-Methyl-5-nitroquinoxalin-6-amine

To a solution of N-methyl-N-(quinoxalin-6-yl)acetamide (4.02 g, 0.02 mol) in DCM (60 mL) was added a solution of potassium nitrate (4.02 g, 0.04 mol) in sulfuric acid (10 mL) cooled to 0° C. The mixture was then warmed and stirred at room temperature for 4 h. Water (20 mL) was added. The mixture was adjusted to pH ~9 with saturated NaOH aqueous solution. Then the mixture was extracted with EtOAc (5×150 mL). The extracts were dried over sodium sulfate and concentrated to give the crude product, which was purified by silica gel column chromatography (eluting with PE/EtOAc v/v 2:1) to give N-methyl-5-nitroquinoxalin-6-amine as a yellow solid (1.4 g, yield 35%). ESI MS: m/z 205.1 [M+H]$^+$. $^1$H NMR (400 MHz, CDCl$_3$) δ 8.85 (d, J=1.6 Hz, 1H), 8.62 (d, J=1.6 Hz, 1H), 8.07 (d, J=9.6 Hz, 1H), 7.67 (brs, 1H), 7.41 (d, J=9.2 Hz, 1H), 3.18 (s, 3H).

f. N$^6$-Methylquinoxaline-5,6-diamine

To a solution of N-methyl-5-nitroquinoxalin-6-amine (1.3 g, 6.4 mmol) in MeOH (100 mL) was added hydrazine hydrate (1.27 g, 25.5 mmol) and Raney Ni (0.2 g). The mixture was stirred at room temperature for 1 h. The mixture was then filtered, and the filtrate was concentrated under reduce pressure to give N$^6$-methylquinoxaline-5,6-diamine as a black solid (1.14 g, yield 100%). ESI MS: m/z 175.1 [M+H]$^+$.

g. (3-Methyl-3H-imidazo[4,5-f]quinoxalin-2-yl)methanol

A mixture of N$^6$-methylquinoxaline-5,6-diamine (1.14 g, 6.4 mmol) and 2-hydroxyacetic acid (486 mg, 6.4 mmol) was stirred at 110° C. for 2 h. Then the mixture was purified by silica gel column chromatography (eluting with DCM/MeOH v/v 30:1) to give (3-methyl-3H-imidazo[4,5-f]quinoxalin-2-yl)methanol as a yellow solid (880 mg, yield 39%). ESI MS: m/z 215.1 [M+H]+.

h. 3-Methyl-3H-imidazo[4,5-f]quinoxaline-2-carbaldehyde

To a solution of (3-methyl-3H-imidazo[4,5-f]quinoxalin-2-yl)methanol (880 mg, 4.03 mmol) in DCM (100 mL) was added activated manganese (IV) dioxide (3.5 g, 40.3 mmol). The mixture was stirred at room temperature for 16 h. Then the mixture was filtered and the filtrate was concentrated under reduce pressure to give the crude product, which was purified by silica gel column (eluting with DCM/MeOH v/v 30:1) to give 3-methyl-3H-imidazo[4,5-f]quinoxaline-2-carbaldehyde as a yellow solid (310 mg, yield 36%). ESE MS: m/z 213.0 [M+H]+. $^1$H NMR (400 MHz, CDCl$_3$): δ 10.25 (s, 1H), 9.02 (d, J=2.0 Hz, 1H), 8.95 (d, J=2.4 Hz, 1H), 8.15 (d, J=9.2 Hz, 1H), 7.88 (d, J=9.2 Hz, 1H), 4.33 (s, 3H).

13. General Procedure M

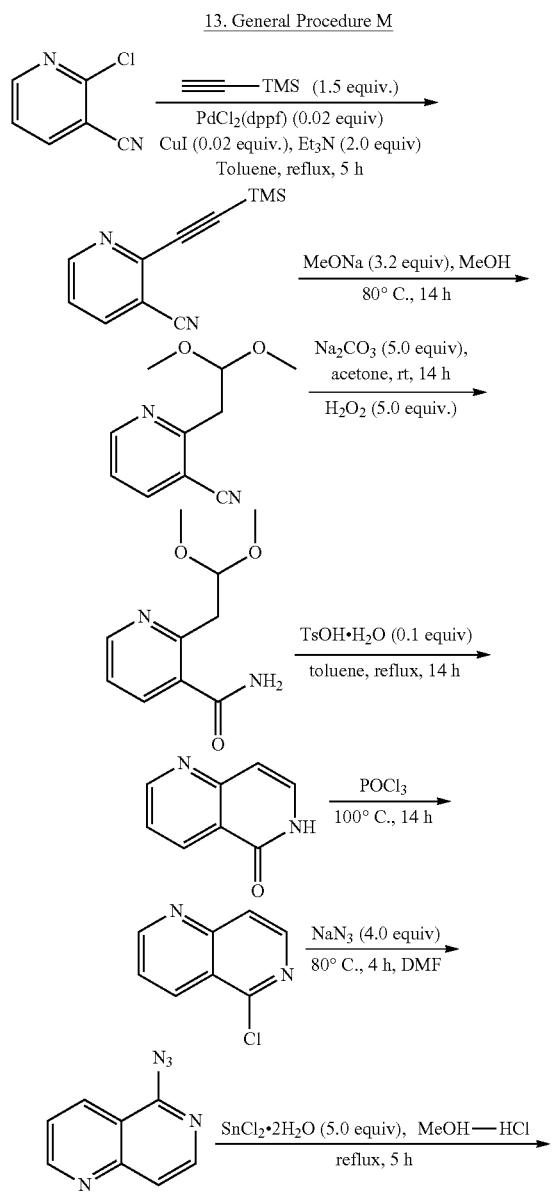

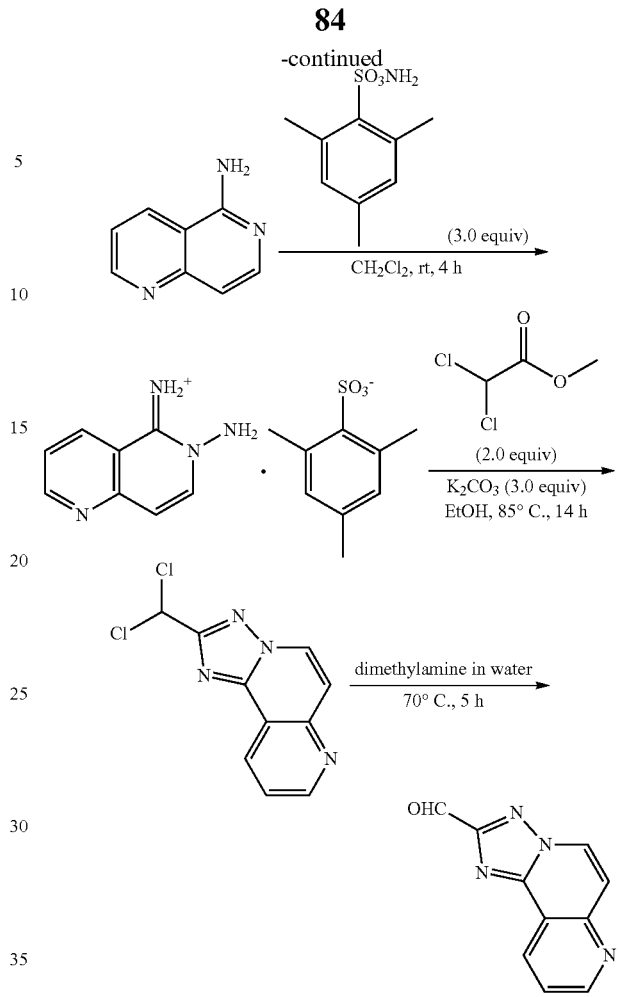

a. 2-((Trimethylsilyl)ethynyl)nicotinonitrile

To a solution of 2-chloronicotinonitrile (21.6 g, 156 mmol) in toluene (200 mL) was added Pd(dppf)Cl$_2$ (2.3 g, 3.12 mmol), copper (I) iodide (594 mg, 3.12 mmol), triethylamine (32 mL, 312 mmol) and ethynyltrimethylsilane (23 g, 234 mmol). The reaction mixture was stirred at 70° C. under N$_2$ for 5 h. The reaction mixture was filtered through a Celite pad. The filtrate was concentrated under reduced pressure to give a residue. 40 mL of water was added to the residue, and the mixture was extracted with EtOAc (3×100 mL). The combined organic layers were washed with brine (1×100 mL), dried over anhydrous Na$_2$SO$_4$, filtered, and concentrated under reduced pressure to give the crude product. The crude product was purified by silica gel column chromatography (eluting with a gradient of PE/EtOAc v/v 40:1, 20:1, 10:1, 5:1) to yield 2-((trimethylsilyl)ethynyl) nicotinonitrile as a yellow solid (19.14 g, yield 61%). ESI MS: m/z 201 [M+H]+.

b. 2-(2,2-Dimethoxyethyl)nicotinonitrile

To a solution of 2-((trimethylsilyl)ethynyl)nicotinonitrile (19.14 g, 95.7 mmol) in MeOH (200 mL) was added sodium methanolate (16.5 g, 306.2 mmol). The reaction mixture was refluxed at 80° C. for 14 h under N$_2$. After removal of the MeOH, the residue was diluted with H$_2$O and extracted with DCM (3×100 mL). The combined organic layers were washed with brine (100 mL), dried over anhydrous Na$_2$SO$_4$, filtered, and concentrated under reduced pressure to give the crude product. The crude product was purified by silica gel column chromatography (eluting with DCM) to yield 2-(2,2-dimethoxyethyl)nicotinonitrile as a yellow oil (13.76 g, yield 75%). ESI MS: m/z 193 [M+H]$^+$.

c. 2-(2,2-Dimethoxyethyl)nicotinamide

A mixture of 2-(2,2-dimethoxyethyl)nicotinonitrile (7 g, 36.42 mmol), aqueous Na$_2$CO$_3$ (3 N, 145 mL), H$_2$O$_2$ (15%, 145 mL) in acetone (73 mL) was stirred at room temperature for 14 h. After removal of acetone, the residue was diluted with water and extracted with DCM (3×100 mL). The combined organic layers were washed with brine (100 mL), dried over anhydrous Na$_2$SO$_4$, filtered, and concentrated under reduced pressure to give the crude product. The crude product was purified by silica gel column chromatography (eluting with PE/EtOAc v/v 1:1 and with EtOAc) to yield 2-(2,2-dimethoxyethyl)nicotinamide as a solid (6 g, yield 78%). ESI MS: m/z 211 [M+H]$^+$, 233 [M+Na]$^+$.

d. 1,6-Naphthyridin-5(6H)-one

A mixture of 2-(2,2-dimethoxyethyl)nicotinamide (8.33 g, 39.7 mmol) and TsOH.H$_2$O (940 mg) in toluene (100 mL) was refluxed for 14 h. Toluene was removed under reduced pressure, then the residue was purified by silica gel column chromatography (eluting with PE/EtOAc v/v 1:1 and with EtOAc) to yield 1,6-naphthyridin-5(6H)-one as a light yellow solid (3.87 g, yield 66%). ESI MS: m/z 147 [M+H]$^+$.

e. 5-Chloro-1,6-naphthyridine

A solution of 1,6-naphthyridin-5(6H)-one (500 mg, 3.42 mmol) in POCl$_3$ (10 mL) was stirred at 100° C. for 14 h. POCl$_3$ was removed under reduced pressure. The residue was dissolved with DCM (40 mL), and the solution was stirred at 0° C. Then aqueous Na$_2$CO$_3$ was added cautiously to adjust pH to 6-7. Then the organic phase was separated from the aqueous phase, and the aqueous phase was extracted with EtOAc (4×15 mL). The combined organic layers were washed with brine (100 mL), dried over anhydrous Na$_2$SO$_4$, filtered, and concentrated under reduced pressure to give 5-chloro-1,6-naphthyridine as a yellow solid (533 mg, yield 95%). ESI MS: m/z 165 [M+H]$^+$.

f. 5-Azido-1,6-naphthyridine

A solution of 5-chloro-1,6-naphthyridine (500 mg, 3.04 mmol) in DMF (5 mL) was stirred at room temperature. Sodium azide (592 mg, 9.12 mmol) was added to the mixture, and the mixture was stirred at 80° C. for 4 h. The mixture was cooled to room temperature and filtered through Celite to remove a white solid. The filtrate was diluted with EtOAc (25 mL) and washed with brine (5×5 mL). The combined organic layers were dried with Na$_2$SO$_4$, filtered, and the solvent was removed under reduced pressure to yield 5-azido-1,6-naphthyridine as a yellow solid, which was used in the next step without further purification (500 mg, yield 96%). ESI MS: m/z 172 [M+H]$^+$.

g. 1,6-Naphthyridin-5-amine

A solution of 5-azido-1,6-naphthyridine (3.2 g, 18.7 mmol) in MeOH (30 mL) was stirred at room temperature. SnCl$_2$.2H$_2$O (21 g, 93.6 mmol) was added to the mixture, followed by the addition of concentrated HCl (10 mL), then the mixture was refluxed for 5 h. The mixture was cooled to room temperature, and neutralized with sat. NaHCO$_3$ to adjust the pH to 7-8. The mixture was filtered, and the aqueous phase was extracted with EtOAc (5×30 mL). The combined organic layers were dried with Na$_2$SO$_4$, filtered, and the solvent was removed under reduced pressure to yield 1,6-naphthyridin-5-amine as a pale yellow solid, which was used in the next step without further purification (2.20 g, yield 81%). ESI MS: m/z 146 [M+H]$^-$. $^1$H NMR (400 MHz, CDCl$_3$) δ 8.91 (dd, $^1$J=1.6 Hz, $^2$J=4.8 Hz, 1H), 8.62 (d, J=8.0 Hz, 1H), 8.00 (d, J=6.0 Hz, 1H), 7.47 (dd, $^1$J=4.8 Hz, $^2$J=8.0 Hz, 1H), 7.09 (br, 2H), 6.98 (d, J=6.0 Hz, 1H).

h. 6-Amino-1,6-naphthyridin-5(6H)-iminium-2,4,6-trimethylbenzenesulfonate

To trifluoroacetic acid (10 mL), stirred at 0° C., was added tert-butyl mesitylsulfonyloxycarbamate (6.50 g, 20.6 mmol), and the mixture was stirred at 0° C. for 30 min. The mixture was poured into ice-water (10 mL). A white precipitate was formed, which was filtered and collected. The white precipitate was dissolved in DCM (20 mL), and dried with Na$_2$SO$_4$. To the DCM solution was added 1,6-naphthyridin-5-amine (1.0 g, 6.88 mmol), and the mixture was stirred at room temperature for 4 h. The solvent was removed under reduced pressure and the residue was washed with Et$_2$O (3×15 mL). The yellow solid obtained was used in the next step without further purification (3.30 g). ESI MS: m/z 161 [M+H]$^+$.

i. 2-(Dichloromethyl)-[1,2,4]triazolo[5,1-f][1,6]naphthyridine

A mixture of 6-amino-1,6-naphthyridin-5(6H)-iminium-2,4,6-trimethylbenzene-sulfonate (3.30 g, 9.17 mmol), methyl 2,2-dichloroacetate (3.93 g, 27.5 mmol) and K$_2$CO$_3$ (3.80 g, 27.5 mmol) in EtOH (30 mL) was refluxed for 14 h. The mixture was then cooled to room temperature, filtered, and washed with DCM (3×20 mL). The combined organic layers were concentrated under reduced pressure. The residue was dissolved in EtOAc (100 mL), washed with brine (5×10 mL), dried with Na$_2$SO$_4$, filtered, and concentrated. The residue was purified by silica gel column chromatography using DCM as eluent to yield 2-(dichloromethyl)-[1,2,4]triazolo[5,1-f][1,6]naphthyridine as a white solid (500 mg, yield 29%). ESI MS: m/z 253, 255 [M+H]$^+$.

j. [1,2,4]Triazolo[5,1-f][1,6]naphthyridine-2-carbaldehyde

A microwave tube was charged with a mixture of 2-(dichloromethyl)-[1,2,4]triazolo[5,1-f][1,6]naphthyridine (180 mg, 0.71 mmol) in dimethylamine in water (5 mL, 33% wt in water) and heated at 70° C. in oil bath for 5 h, and then cooled to room temperature. The mixture was extracted with EtOAc (3×20 mL). The combined organic layer was dried over Na$_2$SO$_4$, filtered, and concentrated. The residue was purified by silica gel column chromatography (eluting with DCM/MeOH v/v 100/1 and 50/1) to yield [1,2,4]triazolo[5,1-f][1,6]naphthyridine-2-carbaldehyde as a white solid (85 mg, yield 60%). ESI MS: m/z 199 [M+H]$^+$. $^1$H NMR (400 MHz, CDCl$_3$) δ 10.22 (s, 1H), 9.06 (m, 1H), 8.97 (m, 1H), 8.56 (d, J=7.2 Hz, 1H), 7.65 (m, 2H).

14. General Procedure N

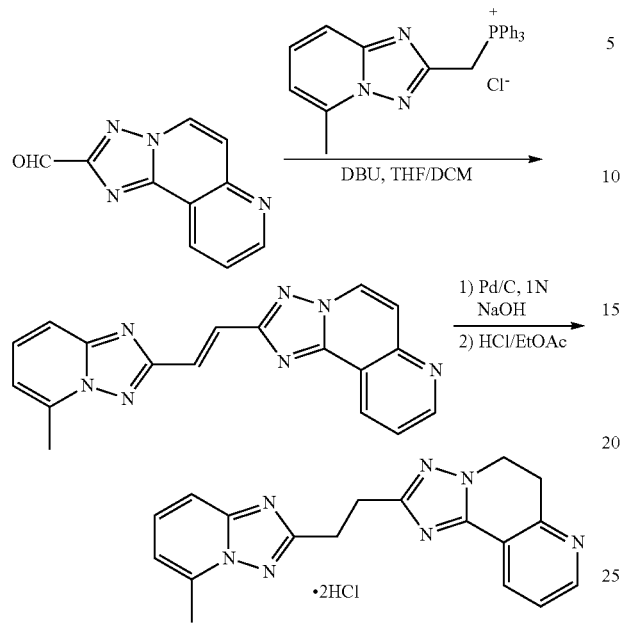

a. (E)-2-(2-(5-Methyl[1,2,4]triazolo[1,5-a]pyridin-2-yl)vinyl)-[1,2,4]triazolo[5,1-f][1,6]naphthyridine To a solution of [1,2,4]triazolo[5,1-f][1,6]naphthyridine-2-carbaldehyde (20 mg, 0.1 mmol) in THF (1 mL) was added a solution of ((5-methyl-[1,2,4]triazolo[1,5-a]pyridin-2-yl)methyl)triphenylphosphonium chloride (49 mg, 0.11 mmol) in DCM (3 mL), followed by the addition of DBU (45 mg, 0.3 mmol) at 0° C. under $N_2$. The resulting mixture was stirred for 4 h at room temperature and diluted with DCM (15 mL). The mixture was washed with water (10 mL), brine (10 mL), dried over anhydrous $Na_2SO_4$, filtered and concentrated to give a crude residue, which was purified by prep. TLC to afford the title compound (17 mg, yield 52%). ESI MS: m/z 328 $[M+H]^+$.

b. 2-(2-(5-Methyl-[1,2,4]triazolo[1,5-a]pyridin-2-yl)ethyl)-5,6-dihydro-[1,2,4]triazolo[5,1-f][1,6]naphthyridine To a solution of (E)-2-(2-(5-methyl-[1,2,4]triazolo[1,5-a]pyridin-2-yl)vinyl)-[1,2,4]triazolo[5,1-f][1,6]naphthyridine (17 mg, 0.52 mmol) in MeOH (3 mL) and aqueous NaOH (1 N, 1 mL) was added 10% Pd/C (17 mg) under a nitrogen atmosphere. The reaction vessel was degassed for three times, followed by treatment with $H_2$ for 1 h at room temperature. The mixture was then submitted for prep-HPLC purification to give a free base of the title compound as a white solid. The solid was triturated with a solution of HCl (gas) in EtOAc (2 mL) to afford the di-HCl salt of the title compound as a yellow solid (7.83 mg, yield 37%). ESI MS: m/z 332 $[M+H]^+$.

15. General Procedure O

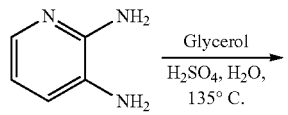

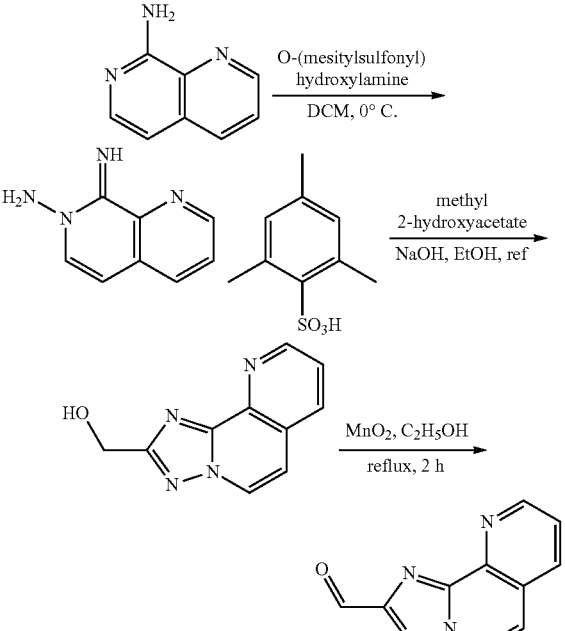

a. 1,7-Naphthyridin-8-amine

A mixture of pyridine-2,3-diamine (5.0 g, 45.9 mmol), glycerol (21.1 g, 229 mmol), sodium 3-nitrobenzenesulphonate (20.6 g, 91.7 mmol), sulfuric acid (20 mL) and water (30 mL) was heated to 135° C. and stirred for 16 h. The mixture was cooled to room temperature and then poured into ice/water (150 g). The mixture was adjusted to pH ~9 with saturated NaOH aqueous solution. Then the mixture was extracted with EtOAc (3×100 mL). The combined organic layers were dried over sodium sulfate and concentrated under reduce pressure to give the crude product, which was purified by silica gel column (eluting with PE/EtOAc v/v 2:1) to give 1,7-naphthyridin-8-amine as a yellow solid (2.6 g, yield 39%). ESI MS: m/z 146.1 $[M+H]^+$.

b. 8-Imino-1,7-naphthyridin-7(8H)-amine-2,4,6-trimethylbenzenesulfonate

To a solution of 1,7-naphthyridin-8-amine (600 mg, 4.13 mmol) in DCM (5 mL) was added a solution of O-(mesitylsulfonyl)hydroxylamine (2.7 g, 12.4 mmol) in DCM (10 mL) at 0° C. The mixture was stirred at 0° C. for 2 h. The precipitate was filtered and collected to give 8-imino-1,7-naphthyridin-7(8H)-amine-2,4,6-trimethylbenzenesulfonate as a brown solid (1.2 g, yield 67%). ESI MS: m/z 161.1 $[M+H]^+$.

c. [1,2,4]Triazolo[1,5-h][1,7]naphthyridin-2-yl-methanol

To a suspension of 8-imino-1,7-naphthyridin-7(8H)-amine-2,4,6-trimethylbenzene-sulfonate (1.2 g, 2.83 mmol) in EtOH (30 mL) was added NaOH (227 mg, 5.67 mmol). The mixture was stirred at 60° C. for 1 h. Then methyl 2-hydroxyacetate (773 mg, 8.50 mmol) was added. The resulting mixture was stirred at reflux for 2 h. The mixture was concentrated and purified by silica gel column chromatography (eluting with DCM/MeOH v/v 30:1) to give [1,2, 4]triazolo[1,5-h][1,7]naphthyridin-2-ylmethanol as a yellow solid (280 mg, yield 49%). ESI MS: m/z 201.1 [M+H]+, d. [1,2,4]Triazolo[1,5-h][1,7]naphthyridine-2-carbaldehyde

To a solution of [1,2,4]triazolo[1,5-h][1,7]naphthyridin-2-ylmethanol (280 mg, 1.4 mmol) in EtOH (20 mL) was added activated manganese (IV) dioxide (1.21 g, 14.0 mmol). The mixture was stirred at reflux for 2 h. Then the mixture was filtered and the filtrate was concentrated under reduce pressure to give [1,2,4]triazolo[1,5-h][1,7]naphthyridine-2-carbaldehyde as a yellow solid (280 mg, yield 88%). ESI MS: m/z 199.1 [M+H]+. $^1$H NMR (400 MHz, CDCl$_3$) δ 10.34 (s, 1H), 9.16 (dd, J=1.6, 4.4 Hz, 1H), 8.55 (d, J=7.2 Hz, 1H), 8.28 (dd, J=1.6, 8.0 Hz, 1H), 7.76 (dd J=4.4, 8.0 Hz, 1H), 7.47 (d, J=8.8 Hz, 1H).

16. General Procedure P

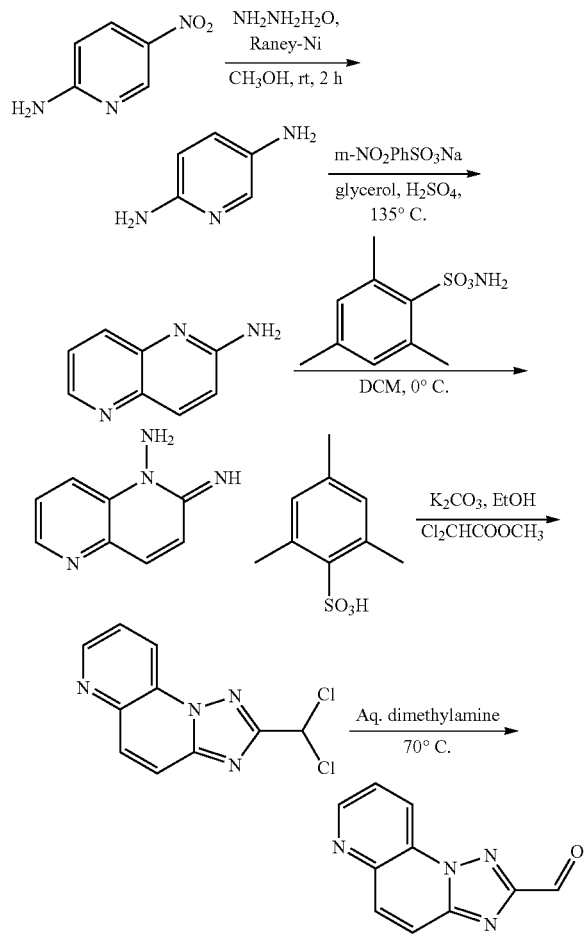

a. Pyridine-2,5-diamine

To a solution of 5-nitropyridin-2-amine (6.95 g, 50.0 mmol) in MeOH (100 mL) was added hydrazine hydrate (5.00 g, 100.0 mmol) and Raney Ni (700 mg). The mixture was stirred at room temperature for 2 h. The catalyst was then removed by filtration and the filtrate was concentrated to give the crude product as a dark oil (5.2 g, yield 68%). ESI MS: m/z 110 [M+H]+.

b. 1,5-Naphthyridin-2-amine

A mixture of pyridine-2,5-diamine (5.2 g, 33.9 mmol), glycerol (15.6 g, 169.5 mmol), sodium 3-nitrobenzenesulphonate (15.2 g, 67.8 mmol), sulfuric acid (20 mL) and water (30 mL) was heated to 135° C. and stirred for 16 h. The mixture was cooled to room temperature and then poured into ice/water (150 g). The pH of the mixture was adjusted to ~9 with saturated aqueous NaOH solution. Then the mixture was extracted with EtOAc (3×100 mL) and the combined organic layers were dried over anhydrous sodium sulfate and concentrated under reduce pressure to give the crude product, which was purified by silica gel column chromatography (eluting with DCM/MeOH v/v 20:1) to afford the product as a yellow solid (2.0 g, yield 41%). ESI MS: m/z 146 [M+H]+. $^1$H NMR (400 MHz, DMSO-d$_6$): δ 8.50 (dd, J=1.6 Hz, 4.4 Hz, 1H), 7.94 (d, J=8.8 Hz, 1H), 7.82-7.80 (m, 1H), 7.47 (dd, J=4.0 Hz, 8.4 Hz, 1H), 7.00 (d, J=9.2 Hz, 1H), 6.72 (s, 2H).

c. 1-Amino-1,5-naphthyridin-2(1H)-iminium-2,4,6-trimethyl-benzenesulfonate

To a solution of 1,5-naphthyridin-2-amine (2.0 g, 13.8 mmol) in DCM (10 mL) was added a solution of O-(mesitylsulfonyl)hydroxylamine (8.9 g, 41.3 mmol) in DCM (20 mL) at 0° C. The mixture was stirred at 0° C. for 3 h. The precipitate was filtered and collected to give the crude product as a yellow solid (4.2 g, yield 85%). ESI MS: m/z 161 [M+H]+.

d. 2-(Dichloromethyl)-[1,2,4]triazolo[1,5-a][1,5]naphthyridine

A suspension of 1-amino-1,5-naphthyridin-2(1H)-iminium-2,4,6-trimethyl-benzenesulfonate (crude product from the previous step, 3.0 mmol), methyl 2,2-dichloroacetate (0.86 g, 6.0 mmol) and potassium carbonate (0.62 g, 4.5 mmol) in EtOH (30 mL) was stirred at 80° C. for 16 h. After cooled to room temperature, the reaction mixture was concentrated and the residue was purified by silica gel column chromatography (eluting with 2% v/v MeOH in DCM) to give the title compound as a purple solid (300 mg, yield 39%). ESI MS: m/z 253, 255 [M+H]+.

e. [1,2,4]Triazolo[1,5-a][1,5]naphthyridine-2-carbaldehyde

A suspension of 2-(dichloromethyl)-[1,2,4]triazolo[1,5-a][1,5]naphthyridine (115 mg, 0.455 mmol) in aqueous dimethylamine (3 mL, 33% wt in water) was heated to 70° C. for 3 h. The mixture was cooled to room temperature, diluted with DCM (10 mL), filtered through a short plug filled with silica gel to remove basic impurities, and concentrated to give the title compound as a white solid (65 mg, yield 72%). ESI MS: m/z 199 [M+H]+.

17. General Procedure Q

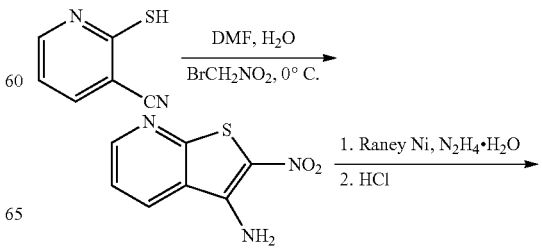

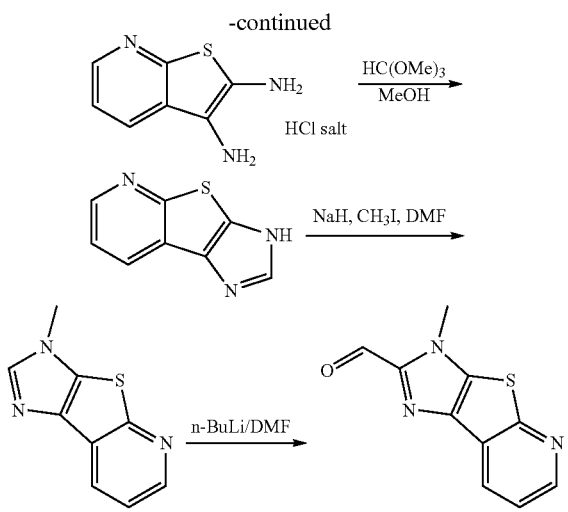

a. 2-Nitrothieno[2,3-b]pyridin-3-amine

To a solution of 2-mercaptonicotinonitrile (1 g, 7.4 mmol) in DMF (20 mL) was added a solution of NaOH (0.88 g, 22 mmol) in water (5 mL) at 0° C. The mixture was stirred for 20 min, then bromonitromethane (2 g, 14.7 mmol) was added dropwise. The resulting mixture was stirred for 1 h at 0° C., diluted with water (100 mL), and filtered. The filter cake was washed with water (20 mL×3) to give a yellow solid (1.1 g, yield 78%), which was used in the next step without further purification. ESI MS: m/z 196 [M+H]$^+$.

b. Thieno[2,3-b]pyridine-2,3-diamine HCl Salt

To a suspension of 2-nitrothieno[2,3-b]pyridin-3-amine (1.1 g, 5.6 mmol) in EtOH (60 mL) was added Raney Ni (1 g), followed by slow addition of N$_2$H$_4$.H$_2$O (1.4 g, 22 mmol). The mixture was stirred at room temperature for 2 h. A solution of HCl in EtOAc (1 M, 18 mL, 18 mmol) was added to the reaction mixture slowly, and the mixture was filtered. The filter cake was washed with EtOAc (20 mL×3), then dried under reduced pressure to give the crude product as a yellow solid (2.7 g). ESI MS: m/z 166 [M+H]$^+$.

c. 3H-Thieno[2,3-b]pyridine[2,3-d]imidazole

A suspension of thieno[2,3-b]pyridine-2,3-diamine HCl salt (2.7 g, crude from the previous step, 5.6 mmol) and methyl orthoformate (3 mL) in MeOH (10 mL) was heated at reflux overnight, then concentrated to give the crude residue as a yellow solid, which was used in the next step without further purification (900 mg, yield 92%). ESI MS: m/z 176 [M+H]$^+$.

d. 3-Methyl-3H-thieno[2,3-b]pyridine[2,3-d]imidazole

To a solution of 3H-thieno[2,3-b]pyridine[2,3-d]imidazole (900 mg, 5.14 mmol) in DMF (5 mL) was added sodium hydride (60% wt in mineral oil, 412 mg, 10.3 mmol) slowly at 0° C. The mixture was stirred for 0.5 h then treated with methyl iodide (730 mg, 5.14 mmol) at 0° C., and the resulting mixture was stirred for 16 h. The mixture was diluted with DCM (15 mL), washed with water (15 mL×3), brine (15 mL), dried over anhydrous Na$_2$SO$_4$, filtered, and concentrated to give a crude residue, which was purified by prep. HPLC to afford the title compound as a yellow solid (194 mg, yield 20%). ESI MS: m/z 190 [M+H]$^+$.

e. 3-Formyl-3H-thieno[2,3-b]pyridine[2,3-d]imidazole

To a pre-cooled solution of 3-methyl-3H-thieno[2,3-b]pyridine[2,3-d]imidazole (57 mg, 0.3 mmol) in THF (2.0 mL) was added n-BuLi (0.48 mL, 1.2 mmol) at 78° C. and the mixture was stirred for 0.5 h. The mixture was then treated with a solution of DMF (44 mg, 0.6 mmol) in THF (0.5 mL) at −78° C., and the resulting mixture was stirred for 1 h at −78° C., then allowed to warm to room temperature. The reaction mixture was quenched with sat. ammonium chloride (5 mL), diluted with DCM (10 mL), washed with water (5 mL), brine (15 mL), dried over anhydrous Na$_2$SO$_4$, filtered, and concentrated to give a crude residue, which was used in the next step without further purification (50 mg, yield 51%). ESI MS: m/z 218 [M+H]$^+$. See, e.g., *J. Het. Chem.*, 1975, 119-22; *Chem. Pharm. Bull.*, 1985, 33, 626-33.

18. General Procedure R

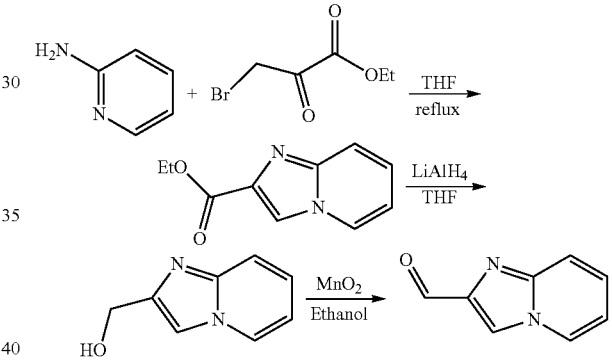

a. Ethyl imidazo[1,2-a]pyridine-2-carboxylate

A solution of 2-aminopyridine (5.0 g, 53.2 mmol) in THF (150 mL) was treated with ethyl bromopyruvate (10.32 g, 57.0 mmol) at room temperature followed by heating the mixture at reflux for 16 h. The resulting white precipitate was collected by filtration and washed with THF (10 mL). Recrystallization of the solids from boiling EtOH (20 mL) gave ethyl imidazo[1,2-a]pyridine-2-carboxylate (6.10 g, 60% yield). ESI MS: m/z 191 [M+1]$^+$. See, e.g., *J. Med. Chem.*, 2003, 46, 3914-29.

b. Imidazo[1,2-a]pyridin-2-ylmethanol

To an ice-cold solution of ethyl imidazo[1,2-a]pyridine-2-carboxylate (6.1 g, 32 mmol) in dry THF (300 mL) was added lithium aluminium hydride (LAH) (2.4 g, 64 mmol) in portions, and the temperature was maintained at <5° C. for 2 h. THF and water (50 mL, 1:1 v/v) were added slowly and the mixture was filtered. The filtrate was evaporated to dryness. The residue was re-dissolved in EtOAc (60 mL), and washed with brine (10 mL×3). The organic layers were combined, and the solvent was removed to give the title compound (4.3 g, yield 90%). ESI MS: m/z 149 [M+H]$^+$.

c. Imidazo[1,2-a]pyridine-2-carbaldehyde

To a solution of imidazo[1,2-a]pyridin-2-ylmethanol (3.0 g, 20 mmol) in EtOH (50 mL) was added manganese (IV) oxide (8.8 g, 100 mmol). The mixture was refluxed for 2 days. After cooling to room temperature, the mixture was filtered through Celite, and the filtrate was concentrated. The residue was purified by reverse phase column chromatography (eluting with acetonitrile in water 25% v/v, with 0.01% $NH_3 \cdot H_2O$) to afford the title compound (0.45 g, 15% yield) as a yellow solid. ESI MS: m/z 147 [M+H]$^+$.

19. General Procedure S

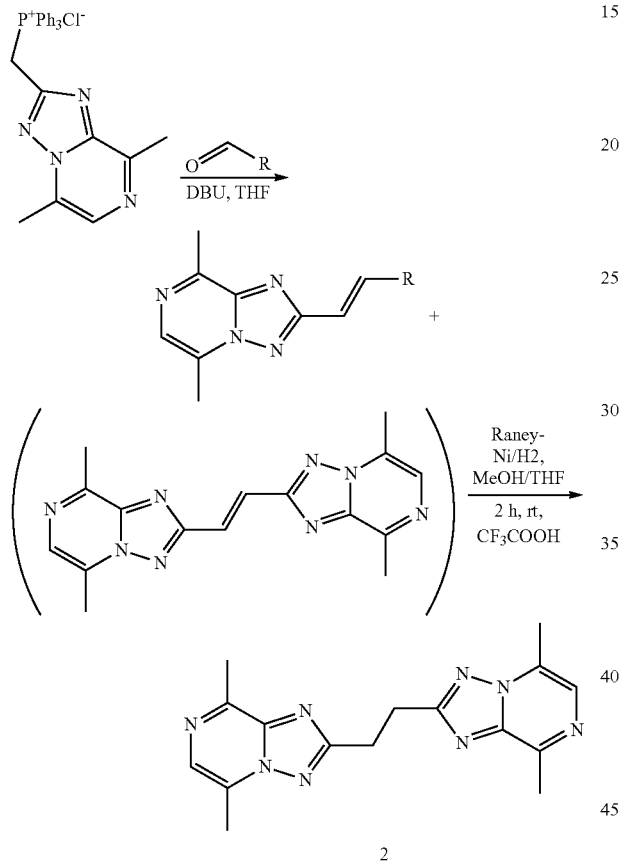

Dimerized triazolopyrazine was prepared by the following method: the Wittig reagent prepared from General Procedure J was employed as the starting material. In the course of a subsequent reaction with an aryl halide (RCHO), the dimerized triazolopyridine was formed as a by-product in about 20% yield. The olefin by-product was purified by flash column chromatography and reduced using standard protocols to afford the dimer compound.

20. General Procedure T

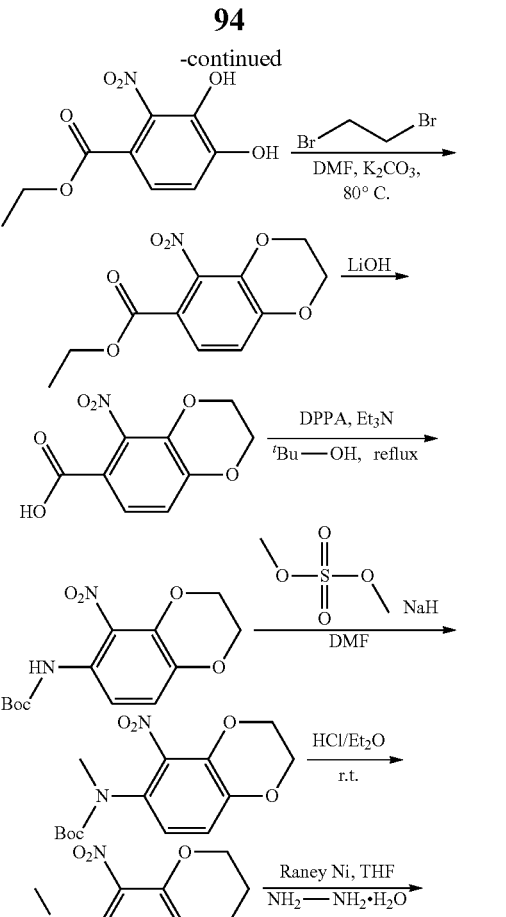

a. Ethyl 3,4-dihydroxy-2-nitrobenzoate

To a solution of ethyl 3,4-dihydroxybenzoate (9.5 g, 52.2 mmol), isopropyl nitrate (13.5 g, 130.5 mmol), and tetrabutylammonium hydrogensulfate (0.884 g, 2.61 mmol) in DCM (100 mL), was added sulfuric acid (14.25 g, 145.6 mmol) slowly at 0° C. The reaction mixture was warmed to room temperature and stirred for 45 min, then quenched with ice/water (150 mL), and extracted with DCM (150 mL×2). The extracts were combined, and the solvent removed under vacuum. The product was purified by silica gel column (20% v/v EtOAc in PE) to give ethyl 3,4-dihydroxy-2-nitrobenzoate (4.97 g, 40% yield). ESI MS: m/z 228 [M+H]$^+$.

b. Ethyl 5-nitro-2,3-dihydrobenzo[b][1,4]dioxine-6-carboxylate

A mixture of ethyl 3,4-dihydroxy-2-nitrobenzoate (4.97 g, 21.9 mmol), 1,2-dibromoethane (6.70 g, 43.8 mmol), and potassium carbonate (6.04 g, 43.8 mmol) in DMF (100 mL) was stirred at 80° C. overnight. To the reaction mixture was added ice/water (100 mL), and the resulting mixture was extracted with EtOAc (200 mL×2). The extracts were combined and dried, and the solvent removed. The product was purified by silica gel column (10% v/v EtOAc in PE) to give ethyl 5-nitro-2,3-dihydrobenzo[b][1,4]dioxine-6-carboxylate (4.30 g, 78% yield). ESI MS: m/z 254 [M+H]⁺.

c. 5-Nitro-2,3-dihydrobenzo[b][1,4]dioxine-6-carboxylic acid

A mixture of ethyl 5-nitro-2,3-dihydrobenzo[b][1,4]dioxine-6-carboxylate (4.30 g, 17.0 mmol) and lithium hydroxide (2.86 g, 68 mmol) in acetonitrile (20 mL) and water (20 mL) was stirred at room temperature for 6 h. The acetonitrile was then removed, and the resulting mixture was extracted with EtOAc (100 mL×2). The extracts were combined and dried, and the solvent removed. The crude product was used in the next step without further purification. ESI MS: m/z 226 [M+H]⁺.

d. tert-Butyl 5-nitro-2,3-dihydrobenzo[b][1,4]dioxin-6-ylcarbamate

A mixture of 5-nitro-2,3-dihydrobenzo[b][1,4]dioxine-6-carboxylic acid (3.80 g, 16.9 mmol), diphenylphosphoryl azide (5.10 g, 18.6 mmol) and triethylamine (1.88 g, 18.6 mmol) in tert-butanol (50 mL) was stirred at 100° C. for 16 h. The reaction mixture was cooled to 20° C., and the solvent removed. The residue was dissolved in DCM (150 mL) and washed with water (150 mL×2), and the solvent was removed. The residue was purified by silica gel column (10% v/v EtOAc in PE) to give tert-butyl 5-nitro-2,3-dihydrobenzo[b][1,4]dioxin-6-ylcarbamate (2.30 g, 46% yield). ESI MS: m/z 297 [M+H]⁺.

e. tert-Butyl methyl(5-nitro-2,3-dihydrobenzo[b][1,4]dioxin-6-yl)carbamate

A mixture of tert-butyl 5-nitro-2,3-dihydrobenzo[b][1,4]dioxin-6-ylcarbamate (2.3 g, 7.8 mmol) in DMF (25 mL) was stirred at 0° C. Sodium hydride (373 mg, 9.3 mmol) was added slowly. Dimethyl sulfate (1.017 g, 9.3 mmol) was added dropwise and the mixture was stirred at 0° C. for 0.5 h. To the reaction mixture was slowly added water (40 mL). The mixture was extracted with toluene (40 mL), the organic phase was washed with water (40 mL) and dried, and the solvent removed. The product was purified by silica gel column (5% v/v EtOAc in PE) to give tert-butyl methyl(5-nitro-2,3-dihydrobenzo[b][1,4]dioxin-6-yl)carbamate (2.2 g, 92% yield). ESI MS: m/z 311 [M+H]⁺.

f. N-Methyl-5-nitro-2,3-dihydrobenzo[b][1,4]dioxin-6-amine tert-Butyl methyl(5-nitro-2,3-dihydrobenzo[b][1,4]dioxin-6-yl)carbamate (2.2 g, 7.1 mmol) in 2.0 M hydrochloric acid in Et₂O (30 mL) was stirred at room temperature for 3 h. The volatiles were removed to give N-methyl-5-nitro-2,3-dihydrobenzo[b][1,4]dioxin-6-amine (1.42 g, 95% yield). ESI MS: m/z 211 [M+H]⁺.

g. N-6-Methyl-2,3-dihydrobenzo[b][1,4]dioxine-5,6-diamine

A mixture of N-methyl-5-nitro-2,3-dihydrobenzo[b][1,4]dioxin-6-amine (1.42 g, 6.7 mmol) and Raney Ni (192 mg) in THF (40 mL) was stirred at room temperature. Hydrazine hydrate (1.14 g, 22.86 mmol) was added drop-wise. The reaction mixture was stirred at room temperature for 1 h, then filtered, and the solvent removed to give the crude product. The crude product was purified by silica gel column (20% v/v EtOAc in PE) to give N-6-methyl-2,3-dihydrobenzo[b][1,4]dioxine-5,6-diamine (1.0 g, 83% yield). ESI MS: m/z 181 [M+H]⁺.

21. General Procedure U

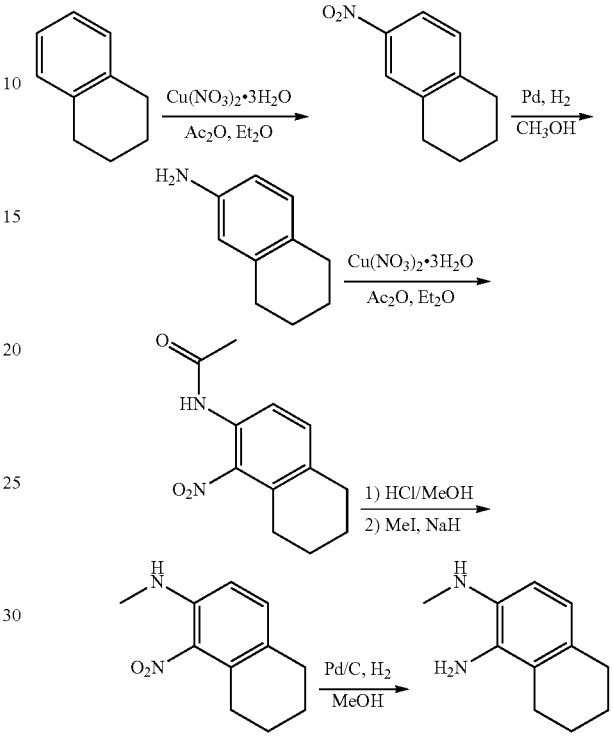

a. 6-Nitro-1,2,3,4-tetrahydronaphthalene and 5-nitro-1,2,3,4-tetrahydronaphthalene To a solution of 1,2,3,4-tetrahydronaphthalene (26.4 g, 200 mmol) in Et₂O (200 mL) was added acetic anhydride (67 mL, 760 mmol) and cupric nitrate trihydrate (48.4 g, 200 mmol). The resulting mixture was stirred at room temperature for 16 h. After filtration, the filtrate was concentrated, and the residue was purified by silica gel column (PE/EtOAc v/v 100:2) to give a yellow oil (5.5 g, yield 15.6%) as a mixture of 6-nitro-1,2,3,4-tetrahydronaphthalene and 5-nitro-1,2,3,4-tetrahydronaphthalene, which was used in the next step. ESI MS: m/z 178 [M+H]⁺.

b. 5,6,7,8-Tetrahydronaphthalen-2-amine

To a solution of 6-nitro-1,2,3,4-tetrahydronaphthalene and 5-nitro-1,2,3,4-tetrahydronaphthalene (5.5 g, 31.1 mmol) in MeOH (50 mL) was added 10% palladium on carbon (3.18 g, 3.0 mmol) under nitrogen, then replaced with hydrogen atmosphere (2 L). The resulting mixture was stirred at room temperature for 16 h, and filtered through Celite. The filtrate was concentrated, and the residue was purified by silica gel column (PE/EtOAc v/v 10:1) to give 5,6,7,8-tetrahydronaphthalen-2-amine as a white solid (2 g, 40% yield). ESI MS: m/z 148 [M+H]⁺. ¹H NMR (400 MHz, CDCl₃): δ 6.88 (d, J=8.0 Hz, 1H), 6.49 (dd, J=2.0 Hz, J=8.0 Hz, 1H), 6.44 (d, J=2.0 Hz, 1H), 3.49 (s, 2H), 2.69-2.67 (m, 4H), 1.78-1.75 (m, 4H).

c. N-(1-Nitro-5,6,7,8-tetrahydronaphthalen-2-yl) acetamide

To a solution of 5,6,7,8-tetrahydronaphthalen-2-amine (2 g, 13.6 mmol) in Et$_2$O (50 mL) was added acetic anhydride (4.6 mL, 51.7 mmol) and cupric nitrate trihydrate (3.3 g, 13.6 mmol). The resulting mixture was stirred at room temperature for 4 h and filtered. The filtrate was concentrated, and the residue was purified by silica gel column chromatography (PE/EtOAc v/v 5:1) to give N-(1-nitro-5,6,7,8-tetrahydronaphthalen-2-yl)acetamide as a white solid (800 mg, 25% yield). ESI MS: m/z 235 [M+H]$^+$.

d. N-Methyl-1-nitro-5,6,7,8-tetrahydronaphthalen-2-amine

A mixture of N-(1-nitro-5,6,7,8-tetrahydronaphthalen-2-yl)acetamide (800 mg, 3.88 mmol) in a 10 M solution of hydrochloric acid in MeOH were heated to reflux for 4 h. After concentration, the residue was basified with 2 N aqueous solution of NaOH to pH 9, then extracted with EtOAc (50 mL×2). The organic layer was washed with brine (30 mL), dried, and concentrated. The residue was dissolved in DMF (20 mL), cooled to 0° C., and NaH (60% dispersion in mineral oil, 0.155 mg, 3.88 mml) was added in one portion. Iodomethane (582 mg, 3.88 mmol) was added dropwise. The resulting mixture was stirred at the same temperature for another 2 h. The reaction mixture was quenched by ice (20 g) and then extracted with EtOAc (50 mL×2). The organic layer was washed with brine (20 mL), dried, and concentrated to give a yellow solid (190 mg). ESI MS: m/z 207 [M+H]$^-$.

e. N$^2$-Methyl-5,6,7,8-tetrahydronaphthalene-1,2-diamine

To a solution of N-methyl-1-nitro-5,6,7,8-tetrahydronaphthalen-2-amine (crude product from the previous step, 190 mg, 0.918 mmol) in MeOH (20 mL) was added 10% Pd on carbon (98 mg, 0.0918 mmol) under nitrogen, then replaced with hydrogen atmosphere (1 L). The resulting mixture was stirred at room temperature for 16 h. After filtration through Celite, the filtrate was concentrated and the residue was purified by prep-TLC (DCM/MeOH v/v 10:1) to give N$^2$-methyl-5,6,7,8-tetrahydronaphthalene-1,2-diamine as a white solid (100 mg, 61% yield). ESI MS: m/z 177 [M+H]$^+$

22. General Procedure V

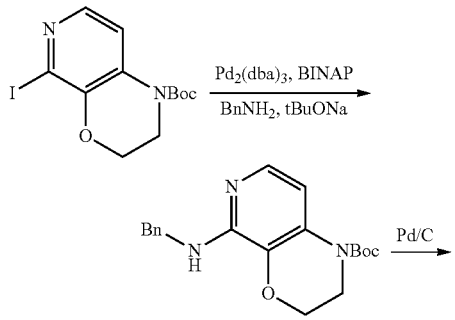

a. tert-Butyl 5-(benzylamino)-2,3-dihydropyrido[3,4-b][1,4] oxazine-1-carboxylate A mixture of tert-butyl 5-iodo-2,3-dihydropyrido[3,4-b][1,4]oxazine-1-carboxylate (5 g, 13.8 mmol), benzylamine (1.776 g, 16.6 mmol), bis(dibenzylideneacetone)palladium (397 mg, 0.79 mmol), (+/−)-2,2'-bis(diphenylphosphino)-1,1'-binaphthyl (858 mg, 1.38 mmol), and sodium tert-butoxide (2.65 g, 27.6 mmol) in dioxane (50 mL) was heated to 120° C. for 16 h under nitrogen. The mixture was filtered. The filtrate was concentrated. The residue was purified by silica gel column chromatography (PE/EtOAc v/v 1:1) to give tert-butyl 5-(benzylamino)-2,3-dihydropyrido[3,4-b][1,4]oxazine-1-carboxylate (3.6 g, 76% yield) as a yellow solid. ESI MS: m/z 342 [M+H]$^+$.

b. tert-Butyl 5-amino-2,3-dihydropyrido[3,4-b][1,4] oxazine-1-carboxylate

A mixture of tert-butyl 5-(benzylamino)-2,3-dihydropyrido[3,4-b][1,4]oxazine-1-carboxylate (3.6 g, 10.56 mmol) and 10% Pd on carbon (1.12 g, 1.06 mmol) in MeOH (100 mL) was stirred under hydrogen atmosphere (2 L) at 35° C. for 48 h. The mixture was then filtered through Celite and washed with MeOH (3×25 mL). The combined organic layer was concentrated under reduced pressure. The residue was re-dissolved in EtOAc (100 mL) and washed with brine (2×50 mL). The combined organic layer was dried over sodium sulfate, filtered, and the solvent removed under reduced pressure. The residue was purified by reverse phase column chromatography (eluting with 22% acetonitrile in water, with 0.1% NH$_3$.H$_2$O) to give tert-butyl 5-amino-2,3-dihydropyrido[3,4-b][1,4]oxazine-1-carboxylate (2.1 g, 79% yield) as a yellow solid. ESI MS: m/z 252 [M+H]$^+$.

c. tert-Butyl 4-(hydroxymethyl)-5-methyl-13-oxa-3,6,10-triazatricyclo[7.4.0.0$^{\{2,6\}}$]trideca-1(9),2,4,7-tetraene-10-carboxylate To a solution of tert-butyl 5-amino-2,3-dihydropyrido[3,4-b][1,4]oxazine-1-carboxylate (2.1 g, 8.37 mmol) in 100 mL of THF was added ethyl 3-bromo-2-oxobutanoate (3.482 g, 16.74 mmol). The mixture was stirred under reflux overnight. After removal of the solvent, the crude product was purified by silica gel column chromatography (EtOAc/PE v/v 2:1) to give 10-tert-butyl 4-ethyl 5-methyl-13-oxa-3,6,10-triazatricyclo[7.4.0.0$^{\{2,6\}}$]trideca-1(9),2,4,7-tetraene-4,10-dicarboxylate (757 mg, 25% yield).

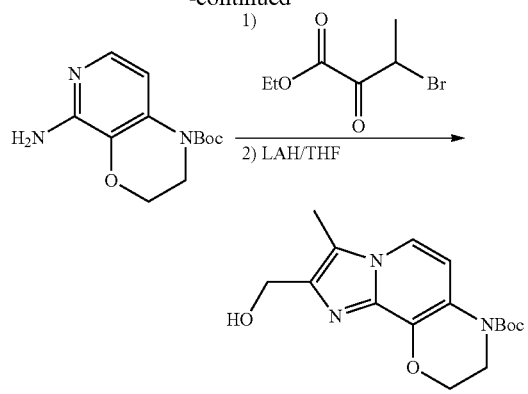

To a solution of 10-tert-butyl 4-ethyl 5-methy-13-oxa-3,6,10-triazatricyclo [7.4.0.0{2,6}]trideca-1(9),2,4,7-tetraene-4,10-dicarboxylate (757 mg, 2.09 mmol) in 50 mL of THF was added LAH (2.364 g, 6.27 mmol) at 0° C. The mixture was stirred for 3 h at room temperature. To the mixture was added sodium sulfate decahydrate (257 mg) and the mixture was stirred for 15 min at room temperature. The solid was removed by filtration and the filtrate was concentrated. The residue was purified by reverse phase column chromatography (eluting with 15% acetonitrile in water, with 0.1% NH$_3$.H$_2$O) to give tert-butyl 4-(hydroxymethyl)-5-methyl-13-oxa-3,6,10-triazatricyclo[7.4.0.0{2,6}]trideca-1(9),2,4,7-tetraene-10-carboxylate (630 mg, 94% yield) as a white solid. ESI MS: m/z 320 [M+H]$^+$.

EtOAc (100 mL×3). The combined organic layer was dried over sodium sulfate and concentrated to give ethyl 2-oxobutanoate (7.5 g, 98% yield). ESI MS: m/z 131 [M+H]$^+$.

c. Ethyl 3-bromo-2-oxobutanoate

To a suspension of cupric bromide (14.7 g, 66.9 mmol) in EtOAc (150 mL) was added a solution of ethyl 2-oxobutanoate (2.9 g, 22.3 mmol) in chloroform (75 mL). The mixture was heated at reflux for 18 h and then cooled. The solid was filtered through a short pad of diatomite. The filtrate was concentrated and purified by silica gel column chromatography (EtOAc/PE v/v 1:1) to give ethyl 3-bromo-2-oxobutanoate as a yellow oil (3.2 g, 47% yield). ESI MS:

23. General Procedure W

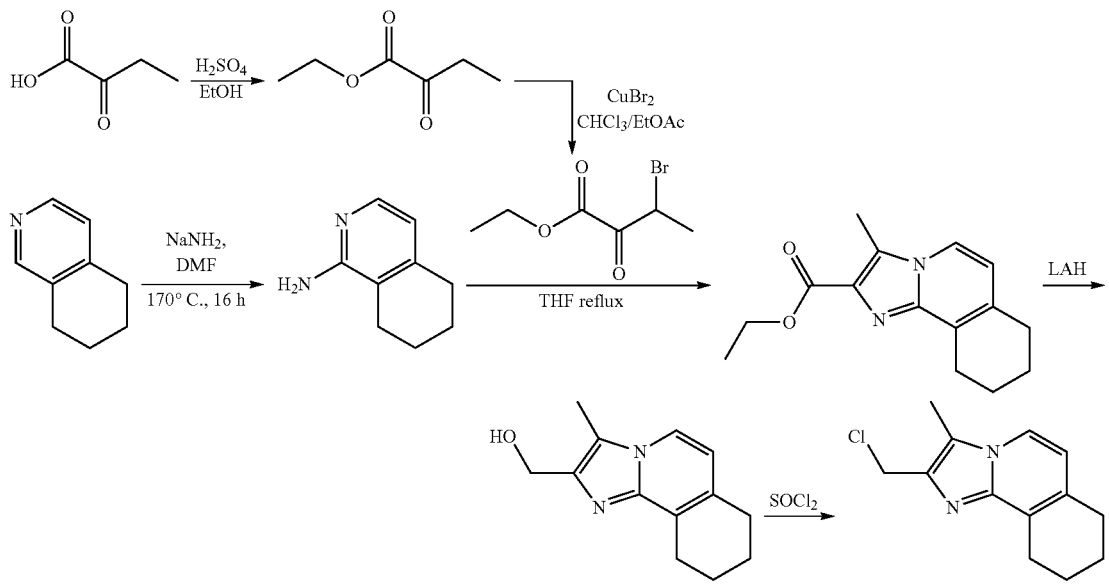

a. 5,6,7,8-Tetrahydroisoquinolin-1-amine

To a solution of 5,6,7,8-tetrahydroisoquinoline (5.0 g, 37.6 mmol) in DMF (8 mL) was added sodium amide (2.55 g, 63.9 mmol). The resulting mixture was heated to 170° C. for 16 h and cooled to room temperature. To the mixture was added aqueous 2 N NaOH (50 mL). The mixture was extracted with DCM (100 mL×3), and the combined organic phase was dried over sodium sulfate and concentrated. The residue was purified by silica gel column chromatography (eluting with DCM/MeOH v/v 10:1) to give 5,6,7,8-tetrahydroisoquinolin-1-amine as a yellow solid (2.6 g, yield 46%). ESI MS: m/z 149 [M+H]$^+$. $^1$H NMR (400 MHz, CDCl$_3$): δ 7.80 (d, J=5.2 Hz, 1H), 6.44 (d, J=5.2 Hz, 1H), 4.34 (br, 2H), 2.67 (t, J=12 Hz, 2H), 2.39 (t, J=12 Hz, 2H), 1.88 (m, 2H), 1.78 (m, 2H).

b. Ethyl 2-oxobutanoate

To a solution of 2-oxobutanoic acid (6.0 g, 58.8 mmol) in EtOH (100 mL) was added sulfuric acid (1 mL) at room temperature. The resulting mixture was stirred for 4 h under reflux. The solvent was removed, and the residue was diluted with water (50 mL) and the pH was adjusted to ~7 with a solution of NaOH (1 N). The mixture was extracted with m/z 209 [M+H]$^+$. $^1$H NMR (400 MHz, CDCl$_3$): δ 5.19 (m, 1H), 4.40 (m, 2H), 1.82 (m, 3H), 1.42 (m, 3H).

d. Ethyl 3-methyl-7,8,9,10-tetrahydroimidazo[2,1-a]isoquinoline-2-carboxylate

To a solution of 5,6,7,8-tetrahydroisoquinolin-1-amine (444 mg, 3 mmol) in 10 mL of THF was added ethyl 3-bromo-2-oxobutanoate (1.248 g, 6 mmol). The mixture was stirred overnight under reflux. After removal of the solvent, the crude product was purified by silica gel column chromatography (EtOAc/PE v/v 4:1) to give ethyl 3-methyl-7,8,9,10-tetrahydro imidazo[2,1-a]isoquinoline-2-carboxylate as a white solid (170 mg, 22% yield). ESI MS: m/z 259 [M+H]$^+$. $^1$H NMR (400 MHz, CDCl$_3$): δ 7.66 (d, J=7.2 Hz, 1H), 6.63 (d, J=7.2 Hz, 1H), 4.48 (q, J=7.2 Hz, 2H), 3.09 (br, 2H), 2.745 (m, 5H), 1.87 (m, 4H), 1.46 (q, J=7.2 Hz, 3H).

e. 3-Methyl-7,8,9,10-tetrahydroimidazo[2,1-a]isoquinolin-2-yl)methanol

To a solution of ethyl 3-methyl-7,8,9,10-tetrahydroimidazo[2,1-a]isoquinoline-2-carboxylate (210 mg, 0.81 mmol) in 5 mL of THF was added LAH (920 mg, 2.44 mmol) at 0° C. The mixture was stirred for 3 h at room temperature. To the mixture was added sodium sulfate decahydrate (100 mg)

and the mixture was stirred for 15 min at room temperature. The solid was removed by filtration and the filtrate was concentrated to give the crude product of (3-methyl-7,8,9,10-tetrahydroimidazo[2,1-a]isoquinolin-2-yl)methanol (200 mg). ESI MS: m/z 217 [M+H]$^+$. This crude product was used in the next step without further purification.

f. 2-(Chloromethyl)-3-methyl-7,8,9,10-tetrahydroimidazo[2,1-a] isoquinoline

The crude product of (3-methyl-7,8,9,10-tetrahydroimidazo[2,1-a]isoquinolin-2-yl)methanol (200 mg) was dissolved in 5 mL of DCM. To the mixture was added thionyl chloride (0.5 mL) at 0° C. The mixture was stirred overnight at room temperature. After removal of the solvent, the residue was dried under vacuum to give 2-(chloromethyl)-3-methyl-7,8,9,10-tetrahydroimidazo[2,1-a]isoquinoline (200 mg). ESI MS: m/z 235 [M+H]$^+$.

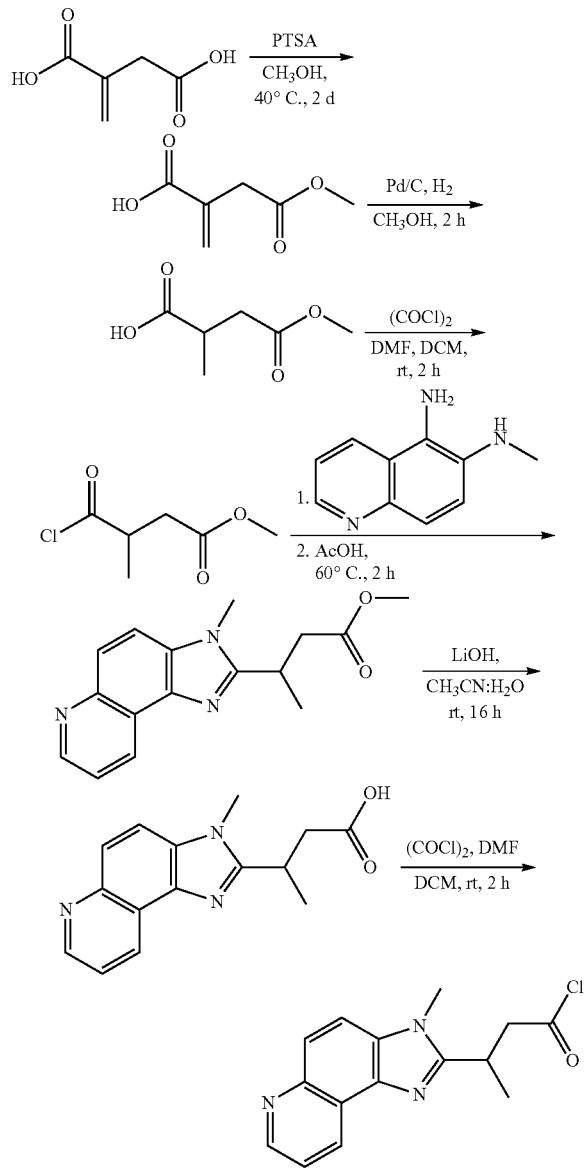

24. General Procedure X a. 4-Methoxy-2-methylene-4-oxobutanoic acid

To a solution of 2-methylenesuccinic acid (5.0 g, 38.4 mmol) in MeOH (200 mL) was added p-toluenesulfonamide (100 mg). The mixture was stirred at 40° C. for 2 days. The mixture was concentrated to dryness. To the residue was added DCM (200 mL). The precipitate was removed by filtration and the filtrate was concentrated to dryness to give the product as a white solid (5.5 g, 99% yield). ESI MS: m/z 145.1 [M+H]$^+$. $^1$H NMR (400 MHz, CDCl$_3$): δ 11.17 (bs, 1H), 6.48 (s, 1H), 5.85 (s, 1H), 3.71 (s, 3H), 3.36 (s, 2H).

b. 4-Methoxy-2-methyl-4-oxobutanoic acid

To a solution of 4-methoxy-2-methylene-4-oxobutanoic acid (1.44 g, 10.0 mmol) in MeOH (100 mL) was added 10% Pd on carbon (200 mg). The mixture was stirred under H$_2$ at room temperature for 2 h. The mixture was filtered and the filtrate was concentrated to dryness to give the product as a colorless oil (1.4 g, 96% yield). ESI MS: m/z 147.1 [M+H]$^+$. $^1$H NMR (400 MHz, CDCl$_3$): δ 3.69 (s, 3H), 2.99-2.94 (m, 1H), 2.77 (d, J=8.0 Hz, 0.5H), 2.73 (d, J=8.4 Hz, 0.5H), 2.46 (d, J=5.6 Hz, 0.5H), 2.42 (d, J=6.4 Hz, 0.5H), 1.27 (d, J=7.6 Hz, 3H).

c. Methyl-4-chloro-3-methyl-4-oxobutanoate

To a solution of 4-methoxy-2-methyl-4-oxobutanoic acid (1.2 g, 8.2 mmol) in oxalyl dichloride (15 mL) and DCM (15 mL) was added DMF (20 mg). The mixture was stirred at room temperature for 2 h. The mixture was concentrated to dryness to give the product as a yellow solid (1.3 g, 96% yield). $^1$H NMR (400 MHz, CDCh): δ 3.71 (s, 3H), 3.35-3.30 (m, 1H), 2.87 (d, J=8.0 Hz, 0.5H), 2.82 (d, J=8.0 Hz, 0.5H), 2.56 (d, J=5.6 Hz, 0.5H) 2.52 (d, J=5.6 Hz, 0.5H), 1.37 (d, J=7.2 Hz, 3H).

d. Methyl 3-(3-methyl-3H-imidazo[4,5-f]quinolin-2-yl)butanoate

To a solution of N$^6$-methylquinoline-5,6-diamine (914 mg, 5.28 mmol) in DCM (30 mL) was added triethylamine (1.07 g, 10.57 mmol). A solution of methyl 4-chloro-3-methyl-4-oxobutanoate (1.3 g, 7.90 mmol) in DCM (10 mL) was added dropwise to the above solution over 5 min. The resulting mixture was stirred at room temperature for 20 min. The mixture was concentrated to dryness. To the residue was added acetic acid (10 mL). The solution was stirred at 60° C. for 2 h. The solvent was removed under reduce pressure and to the residue was added saturated sodium bicarbonate aqueous solution (20 mL). The mixture was extracted with DCM (3×40 mL). The combined organic layer was dried over sodium sulfate, filtered, and concentrated to dryness to give the crude product, which was purified by silica gel column chromatography (DCM/MeOH v/v 30:1) to give the title compound as a yellow solid (560 mg 33% yield). ESI MS: m/z 284.1 [M+H]$^+$. $^1$H NMR (400 MHz, CDCl$_3$): δ 8.94-8.88 (m, 2H), 7.95 (d, J=9.2 Hz, 1H), 7.71 (d, J=8.8 Hz, 1H), 7.50 (dd, J=4.4, 8.4 Hz, 1H), 3.94 (s, 3H), 3.70-3.63 (m, 4H), 3.28 (d, J=8.4 Hz, 0.5H), 3.23 (d, J=8.4 Hz, 0.5H), 2.86 (d, J=6.0 Hz, 0.5H), 2.82 (d, J=6.0 Hz, 0.5H), 1.47 (d, J=6.8 Hz, 3H).

e. 3-(3-Methyl-3H-imidazo[4,5-f]quinolin-2-yl)butanoic acid

To a solution of methyl 3-(3-methyl-3H-imidazo[4,5-f]quinolin-2-yl)butanoate (560 mg, 1.97 mmol) in acetonitrile (20 mL) and water (8 mL) was added lithium hydroxide hydrate (249 mg, 5.94 mmol). The mixture was stirred at room temperature overnight. The mixture was concentrated to about 8 mL. The pH of the solution was adjusted to ~4 with 1N HCl aqueous solution. The mixture was concentrated to dryness and to the residue was added 50 mL of DCM/MeOH v/v 10:1. The precipitate was removed by filtration and the filtrate was concentrated to dryness to give the product as a yellow solid (480 mg, 90% yield). ESI MS: m/z 270.1 [M+H]+.

f. 3-(3-Methyl-3H-imidazo[4,5-f]quinolin-2-yl)butanoyl chloride

To a solution of 3-(3-methyl-3H-imidazo[4,5-f]quinolin-2-yl)butanoic acid (200 mg, 0.74 mmol) in oxalyl chloride (8 mL) and DCM (8 mL) was added DMF (5 mg). The mixture was stirred at room temperature for 2 h. The mixture was concentrated to dryness to give the product as a yellow solid (160 mg, 75% yield). See, e.g., *Indian Journal of Chemistry, Section B: Organic Chemistry Including Medicinal Chemistry*, 2000, 294-296; *Tetrahedron Letters*, 2000, 4165-4168.

25. General Procedure Y

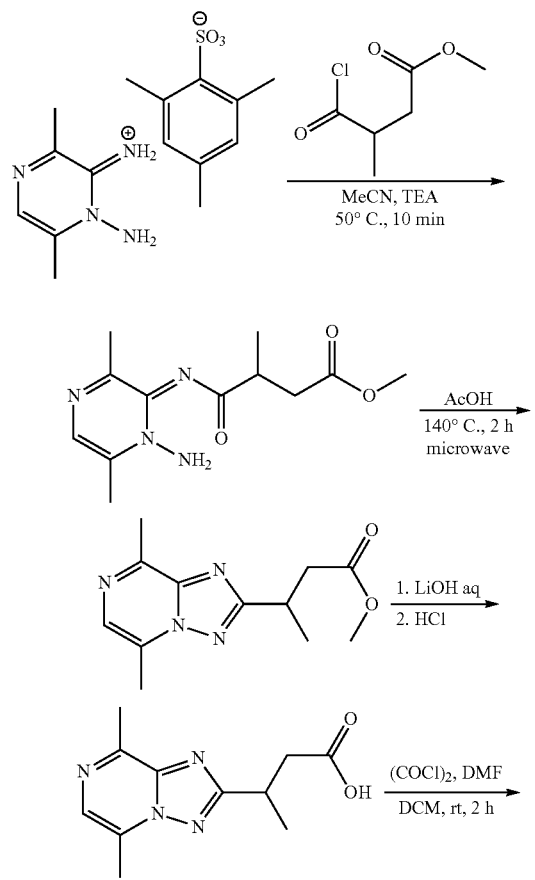

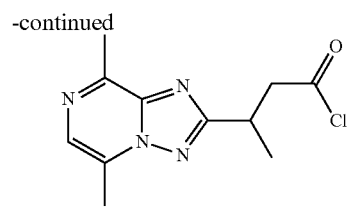

a. Methyl (Z)-4-(1-amino-3,6-dimethylpyrazin-2(1H)-ylideneamino)-3-methyl-4-oxobutanoate To a solution of 2-imino-3,6-dimethylpyrazin-1(2H)-amine-2,4,6-trimethylbenzene-sulfonate (2 g, 5.92 mmol) in acetonitrile (60 mL) was added triethylamine (1.8 g, 17.76 mmol). The mixture was stirred at 50° C. for 30 min. Methyl 4-chloro-3-methyl-4-oxobutanoate (1.35 g, 8.23 mmol) was added. The mixture was stirred for an additional 10 min. Then the solution was evaporated to give 1.1 g of the crude product as a brown solid. ESI MS: m/z 267 [M+H]+.

b. Methyl 3-(5,8-dimethyl-[1,2,4]triazolo[1,5-a]pyrazin-2-yl)butanoate

A solution of (Z)-methyl-4-(1-amino-3,6-dimethyl-pyrazin-2(1H)-ylideneamino)-3-methyl-4-oxobutanoate (1.10 g, 4.14 mmol) in acetic acid (15 mL) was stirred at 140° C. for 2 h in a microwave reactor. The solution was evaporated to give 1.15 g of the product as a brown solid. ESI MS: m/z 248 [M+H]+.

c. 3-(5,8-Dimethyl[1,2,4]triazolo[1,5-a]pyrazin-2-yl)butanoic acid

Methyl 3-(5,8-dimethyl-[1,2,4]triazolo[1,5-a]pyrazin-2-yl)butanoate (1.15 g, 4.64 mmol) in lithium hydroxide aqueous solution (15 mL) was stirred at room temperature for 16 h. Then the pH of the mixture was adjusted to 6 with aqueous hydrogen chloride. The mixture was concentrated and purified by reverse phase column chromatography (eluting with 15% acetonitrile in water, with 0.1% trifluoroacetic acid) to give the product as a yellow solid (420 mg, 39% yield). ESI MS: m/z 235 [M+H]+.

d. 3-(5,8-Dimethyl-[1,2,4]triazolo[1,5-a]pyrazin-2-yl)butanoyl chloride

To a solution of 3-(5,8-dimethyl-[1,2,4]triazolo[1,5-a]pyrazin-2-yl)butanoic acid (200 mg, 0.086 mmol) in DCM (15 mL) was added oxalyl chloride (3 mL) and DMF (0.1 mL). The mixture was stirred at room temperature for 2 h. The mixture was then evaporated under reduced pressure to give the product as a brown solid (208 mg, 96% yield).

26. General Procedure Z

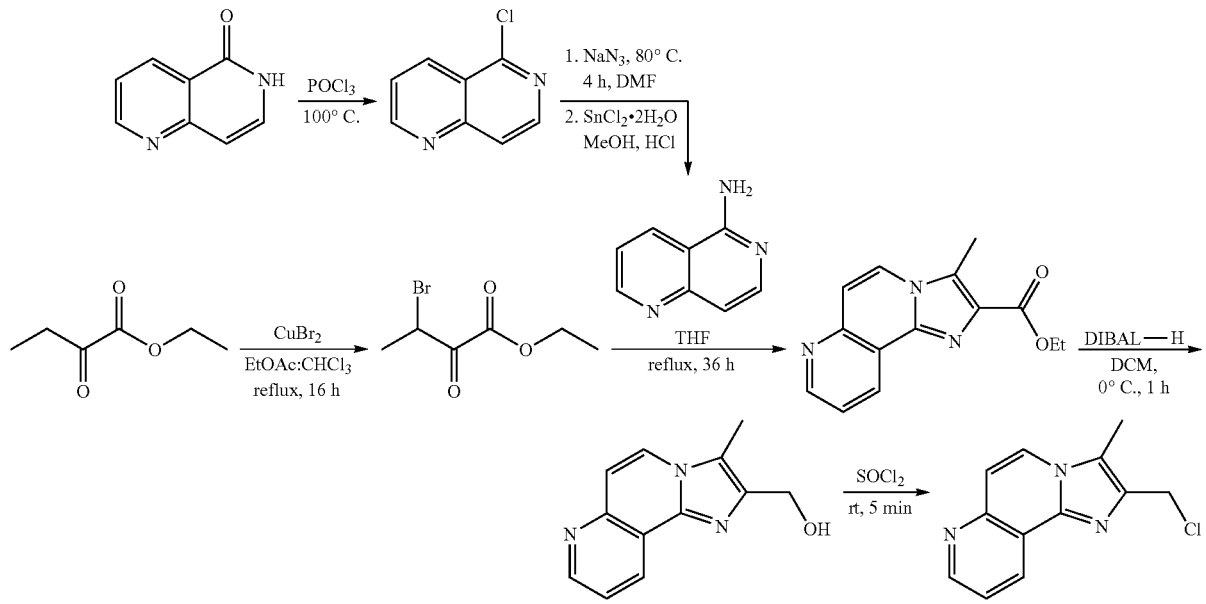

a. 5-Chloro-1,6-naphthyridine

A solution of 1,6-naphthyridin-5(6H)-one (3.2 g, 21.9 mmol) in phosphoryl trichloride (50 mL) was stirred at 100° C. overnight. The volatiles were removed under reduced pressure. The residue was cooled to 0° C. NaOH (saturated aqueous solution) was added to adjust the pH to 9. The mixture was extracted with EtOAc (200 mL×3). The combined organic layers were dried over sodium sulfate and concentrated to give 3.3 g of the crude product as a yellow solid. ESI MS: m/z 165 [M+H]$^+$.

b. 5-Azido-1,6-naphthyridine

To a solution of 5-chloro-1,6-naphthyridine (3.3 g, 20.1 mmol) in DMF (40 mL) was added sodium azide (6.0 g, 88.5 mmol). The mixture was stirred at 80° C. for 4 h. The mixture was then poured into water (120 mL). The aqueous phase was extracted with EtOAc (150 mL×4). The combined organic layers were washed with brine (100 mL×3), dried over sodium sulfate, and concentrated under reduced pressure to give 3.4 g of the crude product as a brown solid. ESI MS: m/z 172 [M+H]$^+$.

c. 1,6-Naphthyridin-5-amine

To a suspension of 5-azido-1,6-naphthyridine (3.4 g, 19.9 mmol) in MeOH (40 mL) was added hydrochloric acid (30 mL). Stannous chloride dihydrate (22.5 g, 99.5 mmol) was added. The mixture was stirred at 75° C. for 3.5 h. A yellow precipitate was formed. The mixture was filtered to give a yellow solid. The solid was suspended in EtOAc (200 mL). NaOH (saturated aqueous solution) was added to adjust pH to 9. A white precipitate was formed. The mixture was filtered and the filtrate was extracted with EtOAc (200 mL×6). The organic phase was dried over sodium sulfate and concentrated under reduced pressure to give 2.0 g of the crude product as a yellow solid. ESI MS: m/z 146 [M+H]$^+$.

d. Ethyl 3-bromo-2-oxobutanoate

To a suspension of CuBr$_2$ (20.6 g, 92.3 mmol) in EtOAc (500 mL) was added a solution of ethyl 2-oxobutanoate (4.0 g, 30.7 mmol) in 250 mL of chloroform. The mixture was heated at reflux for 16 h. The mixture was then cooled and filtered through a short pad of silica gel. The filtrate was concentrated under reduced pressure to give the product as a light green liquid (3.8 g).

e. Methyl 3-methylimidazo[2,1-f][1,6]naphthyridine-2-carboxylate

A solution of 1,6-naphthyridin-5-amine (700 mg, 4.83 mmol) in THF (25 mL) was added ethyl 3-bromo-2-oxobutanoate (1.51 g, 7.24 mmol). The mixture was stirred at reflux for 36 h. Then the mixture was concentrated under reduced pressure, and purified by column chromatography to give the product as a yellow solid (740 mg, 60% yield). ESI MS: m/z 256.1 [M+H]$^+$.

f. (3-Methylimidazo[2,1-f][1,6]naphthyridin-2-yl)methanol

A solution of methyl 3-methylimidazo[2,1-f][1,6]naphthyridine-2-carboxylate (100 mg, 0.39 mmol) in DCM (8 mL) was cooled to 0° C. DIBAL-H (1 M in cyclohexane, 1.2 mL, 1.2 mmol) was added dropwise over 10 min. The mixture was stirred at 0° C. for 1 h. 2 mL of saturated ammonium chloride aqueous solution was added slowly to quench the reaction. Then 5 mL of saturated sodium bicarbonate aqueous solution was added. The mixture was extracted with DCM (3×10 mL). The combined organic layers were dried over sodium sulfate, filtered, and concentrated to give the crude product, which was purified by column chromatography to give 42 mg of the product as a yellow solid. ESI MS: m/z 214.1 [M+H]$^+$.

g. 2-(Chloromethyl)-3-methylimidazo[2,1-f][1,6]naphthyridine

The title compound was prepared according to General Procedure W-(f). ESI MS: m/z 232.1 [M+H]$^+$.

B. Compounds

The following compounds were prepared using the above procedures.

| Compound No. | Structure | Methods of Preparation | Analytical Data |
|---|---|---|---|
| 1 | 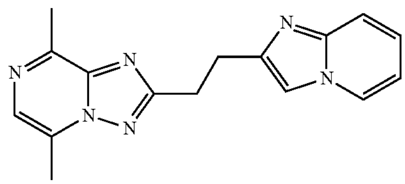 [SMILES: Cc1ncc(C)n2nc(CCc3cn4ccccc4n3)nc12] | J, R | LC-MS: m/z 293.1 (MH$^+$) @ 1.29 min; $^1$H NMR (CDCl$_3$, 400 MHz): δ 8.04 (dt, J = 6.8, 1.2 Hz, 1H), 7.82 (d, J = 0.8 Hz, 1H), 7.54 (dd, J = 9.2, 1.2 Hz, 1H), 7.41 (s, 1H), 7.13 (ddd, J = 8.8, 6.8, 1.2 Hz, 1H), 6.73 (td, J = 6.8, 1.6 Hz, 1H), 3.52-3.41 (m, 4H), 2.89 (s, 3H), 2.72 (s, 3H). |
| 2 | 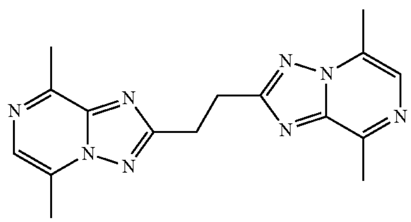 [SMILES: Cc1ncc(C)n2nc(CCc3nc4c(C)ncc(C)n4n3)nc12] | J, S | LC-MS: m/z 323.1 (MH$^+$) @ 1.27 min; $^1$H NMR (CDCl$_3$, 400 MHz): δ 7.83 (d, J = 0.8 Hz, 2H), 3.62 (s, 4H), 2.88 (s, 6H), 2.69 (s, 6H). |
| 3 | 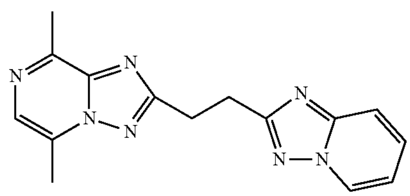 [SMILES: Cc1ncc(C)n2nc(CCc3nc4ccccn4n3)nc12] | J, G | MS (ESI): m/z 294 (MH$^+$); $^1$H NMR (CDCl$_3$, 400 MHz): δ 8.50-8.53 (q, J = 1.2 Hz, 1H), 7.81 (d, J = 1.2 Hz, 1H), 7.67-7.69 (d, J = 8.8 Hz, 1H), 7.46-7.50 (m, 1H), 6.95-6.99 (m, 1H), 3.55-3.61 (m, 4H), 2.87 (s, 3H), 2.69 (s, 3H). |
| 4 | 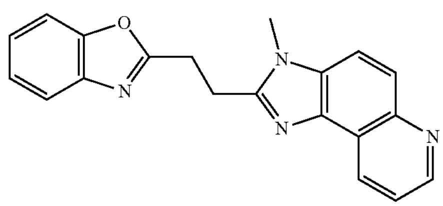 [SMILES: Cn1c(CCc2nc3ccccc3o2)nc2c3cccnc3ccc21] | K | LC-MS: m/z 329.2 (MH$^+$) @ 1.28 min; $^1$H NMR (CDCl$_3$, 500 MHz): δ 8.92-8.89 (m, 2H), 7.96 (d, J = 9.0 Hz, 1H), 7.70-7.66 (m, 1H), 7.69 (d, J = 9.0 Hz, 1H), 7.52-7.49 (m, 2H), 7.34-7.30 (m, 2H), 3.92 (s, 3H), 3.71-3.67 (m, 2H), 3.61-3.57 (m, 2H). |
| 5 | 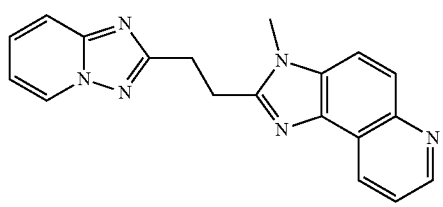 [SMILES: Cn1c(CCc2nc3ccccn3n2)nc2c3cccnc3ccc21] | G, K | LC-MS: m/z 329.1 (MH$^+$) @ 0.85 min; $^1$H NMR (CDCl$_3$, 400 MHz): δ 8.95 (ddd, J = 8.4, 1.6, 0.8 Hz, 1H), 8.89 (dd, J = 4.4, 1.6 Hz, 1H), 8.52 (dt, J = 6.8, 1.2 Hz, 1H), 7.95 (dd, J = 9.0, 0.8 Hz, 1H), 7.69 (d, J = 9.0 Hz, 2H), 7.53-7.49 (m, 2H), 6.99 (td, J = 6.8, 1.2 Hz, 1H), 3.91 (s, 3H), 3.64-3.59 (m, 4H). |
| 6 | 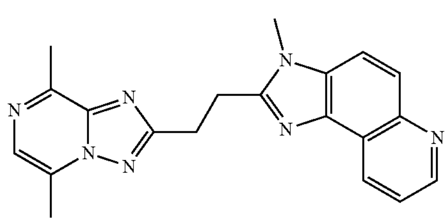 [SMILES: Cc1ncc(C)n2nc(CCc3nc4c5cccnc5ccc4n3C)nc12] | J, K | LC-MS: m/z 358.1 (MH$^+$) @ 1.28 min; $^1$H NMR (CD$_3$OD, 400 MHz): δ 8.93 (dd, J = 8.4, 1.2 Hz, 1H), 8.80 (dd, J = 4.8, 2.0 Hz, 1H), 7.93 (ABq, J$_{AB}$ = 9.2 Hz, V$_{AB}$ = 29 Hz, 2H), 7.86 (brd, J = 0.4 Hz, 1H), 7.62 (dd, J = 8.4, 4.4 Hz, 1H), 4.02 (s, 3H), 3.65 (m, 4H), 2.79 (s, 3H), 2.65 (s, 3H). |

-continued

| Compound No. | Structure | Methods of Preparation | Analytical Data |
|---|---|---|---|
| 7 | 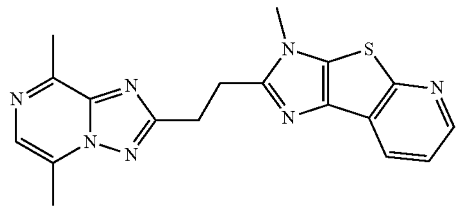 [SMILES: Cc1ncc(C)n2nc(CCc3nc4c5cccnc5sc4n3C)nc12] | J, Q | LC-MS: m/z 364.0 (MH+) @ 1.36 min; $^1$H NMR (CDCl$_3$, 400 MHz): δ 8.42 (dd, J = 4.8, 1.2 Hz, 1H), 8.29 (brd, J = 7.2 Hz, 1H), 7.83 (s, 1H), 7.35 (dd, J = 8.4, 4.8 Hz, 1H), 3.88 (s, 3H), 3.65-3.60 (m, 2H), 3.53-3.49 (m, 2H), 2.87 (s, 3H), 2.69 (s, 3H). |
| 8 | 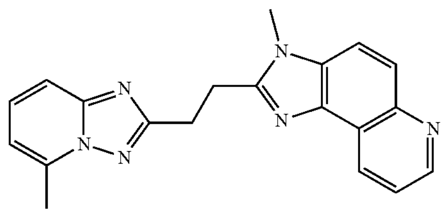 [SMILES: Cc1cccc2nc(CCc3nc4c5cccnc5ccc4n3C)nn12] | E, K | LC-MS: m/z 343.1 (MH+) @ 1.23 min; $^1$H NMR (CDCl$_3$, 400 MHz): δ 8.98 (d, J = 8.8 Hz, 1H), 8.91 (dd, J = 4.4, 1.6 Hz, 1H), 7.85 (ABq, J$_{AB}$ = 8.8 Hz, V$_{AB}$ = 108 Hz, 2H), 7.57 (d, J = 6.8 Hz, 1H), 7.53 (dd, J = 8.8, 4.4 Hz, 1H), 7.43 (dd, J = 8.8, 6.8 Hz, 1H), 6.81 (d, J = 7.2 Hz, 1H), 3.94 (s, 3H), 3.67-3.60 (m, 4H), 2.76 (s, 3H). |
| 9 | 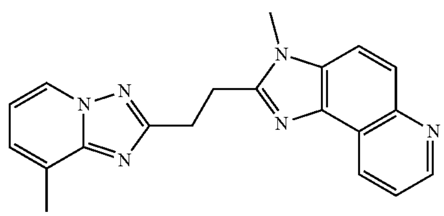 [SMILES: Cc1cccn2nc(CCc3nc4c5cccnc5ccc4n3C)nc12] | F, K | LC-MS: m/z 343.0 (MH+) @ 1.09 min; $^1$H NMR (CD$_3$OD, 400 MHz): δ 9.40 (d, J = 8.4 Hz, 1H), 9.11 (dd, J = 5.2, 1.2 Hz, 1H), 8.55 (d, J = 6.8 Hz, 1H), 8.26 (ABq, J$_{AB}$ = 9.2 Hz, V$_{AB}$ = 104.4 Hz, 2H), 8.06 (dd, J = 9.2, 5.2 Hz, 1H), 7.51 (d, J = 6.8 Hz, 1H), 7.11 (dd, J = 6.8, 6.8 Hz, 1H), 4.16 (s, 3H), 3.81-3.77 (m, 2H), 3.69-3.31 (m, 2H), 2.57 (s, 3H). |
| 10 | 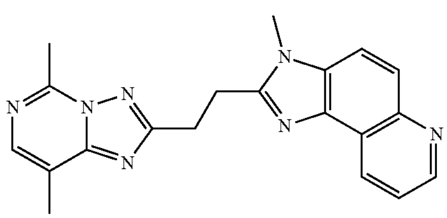 [SMILES: Cc1cnc(C)n2nc(CCc3nc4c5cccnc5ccc4n3C)nc12] | H, K | LC-MS: m/z 358.1 (MH+) @ 1.01 min; $^1$H NMR (DMSO-d$_6$, 500 MHz): δ 8.85 (d, J = 3.0 Hz, 1H), 8.78 (d, J = 8.5 Hz, 1H), 8.02 (s, 1H), 7.92 (ABq, J$_{AB}$ = 8.5 Hz, V$_{AB}$ = 92.6 Hz, 2H), 7.58 (dd, J = 8.0, 4.0 Hz, 1H), 3.96 (s, 3H), 3.53 (m, 4H), 2.82 (s, 3H), 2.45 (s, 3H). |
| 11 | 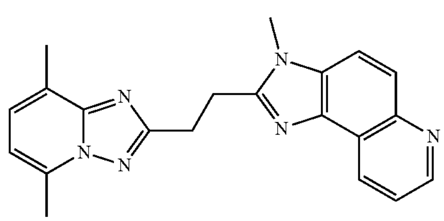 [SMILES: Cc1ccc(C)n2nc(CCc3nc4c5cccnc5ccc4n3C)nc12] | D, K | LC-MS: m/z 357.1 (MH+) @ 1.06 min; $^1$H NMR (CD$_3$OD, 400 MHz): δ 8.91 (d, J = 8.4 Hz, 1H), 8.78 (dd, J = 4.4, 1.2 Hz, 1H), 7.87 (ABq, J$_{AB}$ = 4.8 Hz, V$_{AB}$ = 22.3 Hz, 2H), 7.59 (dd, J = 8.4, 4.4 Hz, 1H), 7.29 (d, J = 7.2 Hz, 1H), 6.81 (d, J = 7.2 Hz, 1H), 3.96 (s, 3H), 3.61-3.51 (m, 4H), 2.601 (s, 3H), 2.50 (s, 3H). |
| 12 | 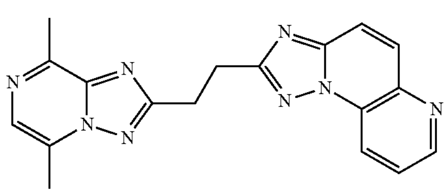 [SMILES: Cc1ncc(C)n2nc(CCc3nc4ccc5ncccc5n4n3)nc12] | J, P | LC-MS: m/z 345.1 (MH+) @ 1.30 min; $^1$H NMR (CDCl$_3$, 400 MHz): δ 8.91 (dd, J = 4.4, 1.2 Hz, 1H), 8.78 (dd, J = 4.8, 0.8 Hz, 1H), 7.97 (ABq, J$_{AB}$ = 10.0 Hz, V$_{AB}$ = 88.2 Hz, 2H), 7.83 (brs, 1H), 7.68 (dd, J = 8.4, 4.4 Hz, 1H), 3.66-3.62 (m, 4H), 2.88 (s, 3H), 2.70 (s, 3H). |

-continued

| Compound No. | Structure | Methods of Preparation | Analytical Data |
|---|---|---|---|
| 13 | 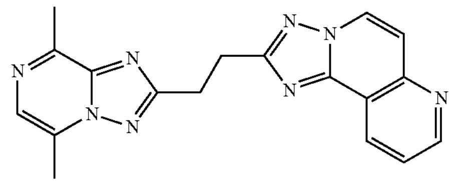 [SMILES: Cc1ncc(C)n2nc(CCc3nc4c5cccnc5ccn4n3)nc12] | J, M | LC-MS: m/z 345.2 (MH+) @ 1.40 min; $^1$H NMR (CDCl$_3$, 400 MHz): δ 9.04 (dd, J = 4.8, 1.6 Hz, 1H), 8.89 (dd, J = 8.0, 1.6 Hz, 1H), 8.49 (d, J = 7.6 Hz, 1H), 7.83 (s, 1H), 7.63 (dd, J = 8.8, 4.8 Hz, 1H), 7.50 (d, J = 7.6 Hz, 1H), 3.65-3.61 (m, 4H), 2.88 (s, 3H), 2.70 (s, 3H). |
| 14 | 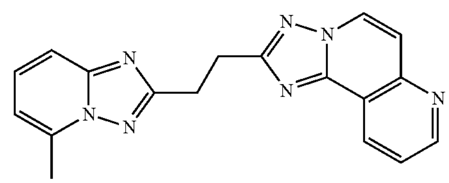 [SMILES: Cc1cccc2nc(CCc3nc4c5cccnc5ccn4n3)nn12] | E, M | LC-MS: m/z 330.1 (MH+) @ 1.32 min; $^1$H NMR (CDCl$_3$, 400 MHz): δ 9.03 (d, J = 4.0 Hz, 1H), 8.90 (d, J = 8.0 Hz, 1H), 8.49 (d, J = 7.6 Hz, 1H), 7.62 (dd, J = 8.0, 4.0 Hz, 1H), 7.49 (d, J = 7.6 Hz, 1H), 7.48 (ABq, J$_{AB}$ = 8.4 Hz, V$_{AB}$ = 67.1 Hz, 2H), 6.79 (d, J = 7.2 Hz, 1H), 3.61 (n, 4H), 2.76 (s, 3H). |
| 15 | 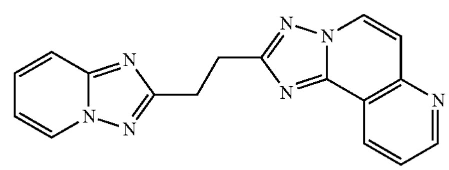 [SMILES: c1cnc2ccn3nc(CCc4nc5ccccn5n4)nc3c2c1] | G, M | LC-MS: m/z 316.1 (MH+) @ 1.24 min; $^1$H NMR (CDCl$_3$, 400 MHz): δ 9.03 (dd, J = 4.5, 2.0 Hz, 1H), 8.90 (dd, J = 8.0, 1.5 Hz, 1H), 8.52 (d, J = 6.5 Hz, 1H), 8.49 (d, J = 7.5 Hz, 1H), 7.68 (d, J = 9.0 Hz, 1H), 7.61 (dd, J = 8.0, 4.5 Hz, 1H), 7.49-7.46 (m, 2H), 6.96 (dt, J = 6.5, 1.0 Hz, 1H), 3.62-3.58 (m, 4H). |
| 16 | 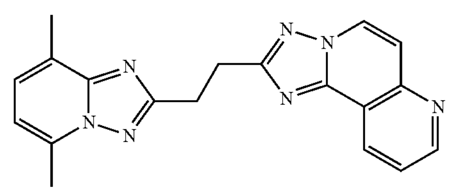 [SMILES: Cc1ccc(C)n2nc(CCc3nc4c5cccnc5ccn4n3)nc12] | D, M | LC-MS: m/z 344.1 (MH+) @ 1.48 min; $^1$H NMR (CDCl$_3$, 400 MHz): δ 9.03 (dd, J = 4.8, 1.6 Hz, 1H), 8.90 (dd, J = 7.2, 2.0 Hz, 1H), 8.50 (d, J = 7.6 Hz, 1H), 7.62 (dd, J = 8.0, 3.6 Hz, 1H), 7.48 (d, J = 7.6 Hz, 1H), 7.17 (d, J = 7.2 Hz, 1H), 6.68 (d, J = 7.6 Hz, 1H), 3.61 (m, 4H), 2.70 (s, 3H), 2.60 (s, 3H). |
| 17 | 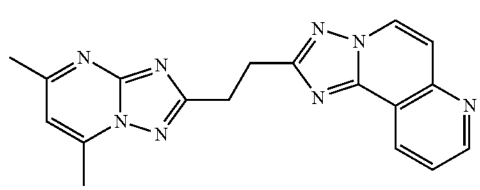 [SMILES: Cc1cc(C)n2nc(CCc3nc4c5cccnc5ccn4n3)nc2n1] | I, M | LC-MS: m/z 345.1 (MH+) @ 1.23 min; $^1$H NMR (CDCl$_3$, 400 MHz): δ 9.03 (d, J = 3.6 Hz, 1H), 8.91 (d, J = 8.4 Hz, 1H), 8.49 (d, J = 7.2 Hz, 1H), 7.63 (dd, J = 8.0, 4.4 Hz, 1H), 7.49 (d, J = 7.6 Hz, 1H), 6.75 (s, 1H), 3.62-3.57 (m, 4H), 2.76 (s, 3H), 2.64 (s, 3H). |
| 18 | 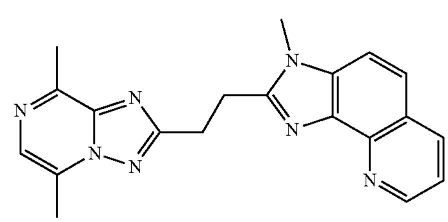 [SMILES: Cc1ncc(C)n2nc(CCc3nc4c5ncccc5ccc4n3C)nc12] | J, K | LC-MS: m/z 358.1 (MH+) @ 1.36 min; $^1$H NMR (CDCl$_3$, 400 MHz): δ 9.00 (dd, J = 4.0, 1.2 Hz, 1H), 8.23 (dd, J = 8.0, 1.2 Hz, 1H), 7.81 (s, 1H), 7.59 (ABq, J$_{AB}$ = 8.4 Hz, V$_{AR}$ = 34.6, 2H), 7.40 (dd, J = 8.0, 4.4 Hz, 1H), 3.94 (s, 3H), 3.83-3.79 (m, 2H), 3.62-3.58 (m, 2H), 2.87 (s, 3H), 2.69 (s, 3H). |

-continued

| Compound No. | Structure | Methods of Preparation | Analytical Data |
|---|---|---|---|
| 19 | 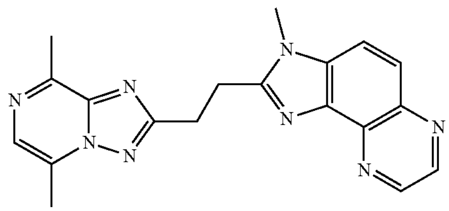 [SMILES: Cc1ncc(C)n2nc(CCc3nc4c5nccnc5ccc4n3C)nc12] | J, L | LC-MS: m/z 359.2 (MH$^+$) @ 0.99 min; $^1$H NMR (CDCl$_3$, 400 MHz): δ 8.94 (d, J = 2.0 Hz, 1H), 8.84 (d, J = 2.0 Hz, 1H), 7.87 (ABq, J$_{AB}$ = 9.2 Hz, V$_{AB}$ = 62.1 Hz, 2H), 7.82 (s, 1H), 3.99 (s, 3H), 3.82 (d, J = 9.6 Hz, 1H), 3.80 (d, J = 8.8 Hz, 1H), 3.62 (d, J = 8.8 Hz, 1H), 3.61 (d, J = 9.6 Hz, 1H), 2.87 (s, 3H), 2.69 (s, 3H). |
| 20 | 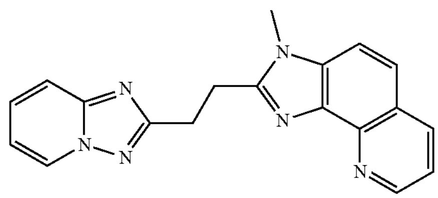 [SMILES: Cn1c(CCc2nc3ccccn3n2)nc2c3ncccc3ccc21] | G, K | LC-MS: m/z 329.0 (MH$^+$) @ 1.34 min; $^1$H NMR (CDCl$_3$, 400 MHz): δ 9.01 (dd, J = 4.4, 1.6 Hz, 1H), 8.53 (d, J = 6.8 Hz, 1H), 8.23 (dd, J = 8.4, 1.6 Hz, 1H), 7.68 (d, J = 8.0 Hz, 1H), 7.58 (ABq, J$_{AB}$ = 9.2 Hz, V$_{AB}$ = 36.9 Hz, 2H), 7.51-7.46 (m, 1H), 7.39 (dd, J = 8.4, 4.4 Hz, 1H), 6.97 (td, J = 8.4, 1.2 Hz, 1H), 3.90 (s, 3H), 3.77-3.73 (m, 2H), 3.60-3.55 (m, 2H). |
| 21 | 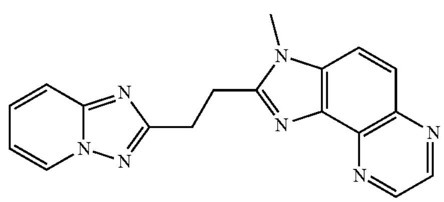 [SMILES: Cn1c(CCc2nc3ccccn3n2)nc2c3nccnc3ccc21] | G, L | MS (ESI): m/z 330 (MH$^+$); $^1$H NMR (CDCl$_3$, 400 MHz): δ 8.95 (d, J = 2 Hz, 1H), 8.85 (d, J = 2 Hz, 1H), 8.53 (ddd, J = 0.8, 2.4, 6.8 Hz, 1H), 7.95 (d, J = 8.8 Hz, 1H), 7.79 (d, J = 8.8 Hz, 1H), 7.69 (d, J = 8.8 Hz, 1H), 7.50 (ddd, J = 1.2, 6.8, 8.4 Hz, 1H), 6.99 (d, J = 1.2, 6.8 Hz, 1H), 3.95 (s, 3H), 3.75 (m, 2H), 3.60 (m, 2H). |
| 22 | 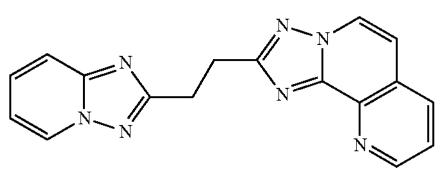 [SMILES: c1cnc2c(c1)ccn1nc(CCc3nc4ccccn4n3)nc21] | G, O | LC-MS: m/z 316.0 (MH$^+$) @ 1.22 min; $^1$H NMR (CDCl$_3$, 400 MHz): δ 9.07 (dd, J = 4.0, 1.2 Hz, 1H), 8.52 (d, J = 6.8 Hz, 1H), 8.40 (d, J = 7.6 Hz, 1H), 8.17 (dd, J = 8.4, 1.6 Hz, 1H), 7.69 (d, J = 8.4 Hz, 1H), 7.64 (dd, J = 8.0, 4.4 Hz, 1H), 7.50-7.45 (m, 1H), 7.21 (d, J = 7.2 Hz, 1H), 6.96 (td, J = 6.8, 1.2 Hz, 1H), 3.65 (brs, 4H). |
| 23 | 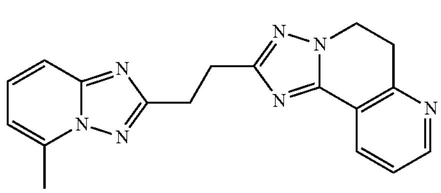 [SMILES: Cc1cccc2nc(CCc3nc4n(n3)CCc3ncccc3-4)nn12] | E, N | LC-MS: m/z 332.1 (MH$^+$) @ 1.27 min; $^1$H NMR (CDCl$_3$, 400 MHz): δ 8.57 (d, J = 4.8 Hz, 1H), 8.25 (d, J = 8.0 Hz, 1H), 7.56 (d, J = 8.8 Hz, 1H), 7.41 (dd, J = 8.8, 7.2 Hz, 1H), 7.33 (dd, J = 7.6, 5.2 Hz, 1H), 6.79 (d, J = 6.8 Hz, 1H), 4.49 (t, J = 7.2 Hz, 2H), 3.50-3.46 (m, 4H), 3.42-3.37 (m, 2H), 2.77 (s, 3H). |
| 24 | 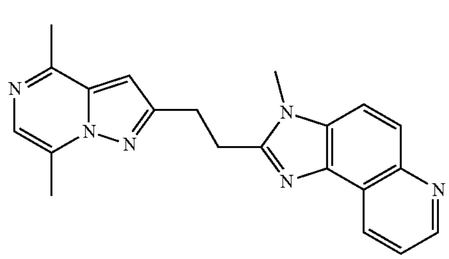 [SMILES: Cc1ncc(C)n2nc(CCc3nc4c5cccnc5ccc4n3C)cc12] | A, K | LC-MS: m/z 357.1 (MH$^+$) @ 1.37 min; $^1$H NMR (CDCl$_3$, 400 MHz): δ 9.01 (dd, J = 8.4, 1.2 Hz, 1H), 8.92 (dd, J = 4.0, 1.2 Hz, 1H), 7.86 (ABq, J$_{AB}$ = 8.8 Hz, V$_{AB}$ = 115.7 Hz, 2H), 7.56 (s, 1H), 7.55 (dd, J = 8.0, 4.4 Hz, 1H), 6.59 (s, 1H), 3.85 (s, 3H), 3.59-3.49 (m, 4H), 2.65 (s, 3H), 2.64 (s, 3H). |

| Compound No. | Structure | Methods of Preparation | Analytical Data |
|---|---|---|---|
| 25 | 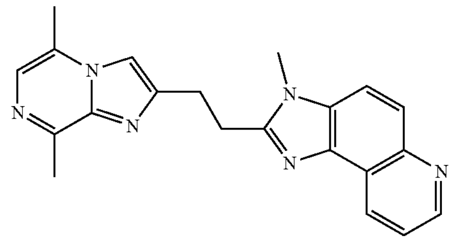 [SMILES: Cc1ncc(C)n2cc(CCc3nc4c5cccnc5ccc4n3C)nc12] | C, K | LC-MS: m/z 357.1 (MH+) @ 1.26 min; ¹H NMR (CD₃OD, 400 MHz): δ 8.87 (dd, J = 8.0, 0.8 Hz, 1H), 8.72 (dd, J = 4.0, 1.6 Hz, 1H), 7.83 (ABq, $J_{AB}$ = 9.2 Hz, $V_{AB}$ = 21.3, 2H), 7.70 (s, 1H), 7.54 (dd, J = 8.8, 4.4 Hz, 1H), 7.48 (brs, 1H), 3.84 (s, 3H), 3.49-3.36 (m, 4H), 2.67 (s, 3H), 2.43 (s, 3H). |
| 26 | 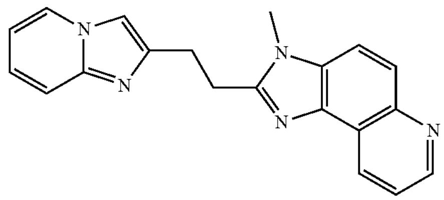 [SMILES: Cn1c(CCc2cn3ccccc3n2)nc2c3cccnc3ccc21] | B, K | LC-MS: m/z 328.1 (MH+) @ 1.31 min; ¹H NMR (CD₃OD, 400 MHz): δ 8.98 (dd, J = 8.4, 1.2 Hz, 1H), 8.81 (dd, J = 4.8, 2.0 Hz, 1H), 8.32 (d, J = 6.8 Hz, 1H), 7.90 (ABq, $J_{AB}$ = 9.2 Hz, $V_{AB}$ = 15.0 Hz, 2H), 7.64 (dd, J = 8.4, 4.0 Hz, 1H), 7.63 (s, 1H), 7.50 (d, J = 9.2 Hz, 1H), 7.31 (ddd, J = 9.2, 6.8, 1.2 Hz, 1H), 6.89 (td, J = 6.8, 0.8 Hz, 1H), 3.86 (s, 3H), 3.51-3.47 (m, 2H), 3.39-3.34 (m, 2H). |
| 27 | 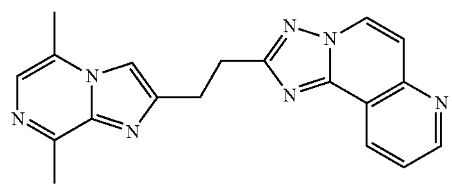 [SMILES: Cc1ncc(C)n2cc(CCc3nc4c5cccnc5ccn4n3)nc12] | C, M | LC-MS: m/z 344.2 (MH+) @ 1.21 min; ¹H NMR (CDCl₃, 400 MHz): δ 9.04 (dd, J = 4.4, 1.6 Hz, 1H), 8.89 (dd, J = 8.4, 1.6 Hz, 1H), 8.49 (d, J = 7.6 Hz, 1H), 7.63 (dd, J = 8.0, 4.4 Hz, 1H), 7.57 (brs, 1H), 7.50 (d, J = 7.2 Hz, 1H), 7.43 (s, 1H), 3.57-3.50 (m, 4H), 2.89 (s, 3H), 2.51 (s, 3H). |
| 28 | 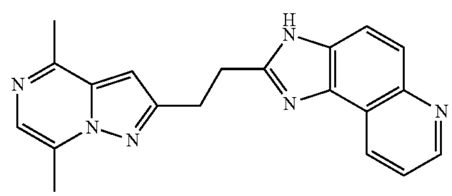 [SMILES: Cc1ncc(C)n2nc(CCc3nc4c(ccc5ncccc54)[nH]3)cc12] | A, K | LC-MS: m/z 343.1 (MH+) @ 1.37 min; ¹H NMR (CDCl₃, 400 MHz): δ 12.30 (brs, 1H), 8.87 (s, 1H), 8.25 (d, J = 8.0 Hz, 1H), 7.90 (m, 1H), 7.64 (s, 1H), 7.60 (d, J = 7.6 Hz, 1H), 7.39 (dd, J = 8.4, 4.0 Hz, 1H), 6.62 (s, 1H), 3.53 (ddd, J = 18.0, 7.2, 4.0 Hz, 4H), 2.90 (s, 3H), 2.69 (s, 3H). |
| 29 | 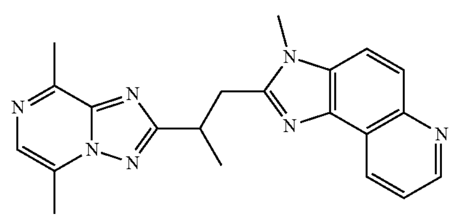 [SMILES: Cc1ncc(C)n2nc(C(C)Cc3nc4c5cccnc5ccc4n3C)nc12] | Y, K | LC-MS: m/z 372.1 (MH+) @ 1.36 min; ¹H NMR (CDCl₃, 400 MHz): δ 8.98 (d, J = 8.4 Hz, 1H), 8.90 (dd, J = 4.8, 2.0 Hz, 1H), 7.89 (d, J = 9.2 Hz, 1H), 7.81 (s, 1H), 7.71 (d, J = 8.8 Hz, 1H), 7.54 (dd, J = 8.4, 4.4 Hz, 1H), 4.11 (sxt, J = 7.2 Hz, 1H), 4.0 (s, 3H), 3.73 (dd, J = 14.8, 7.6 Hz, 1H), 3.42 (dd, J = 14.8, 7.2 Hz, 1H), 2.85 (s, 3H), 2.66 (s, 3H), 1.62 (d, J = 7.2 Hz, 3H). |
| 30 | 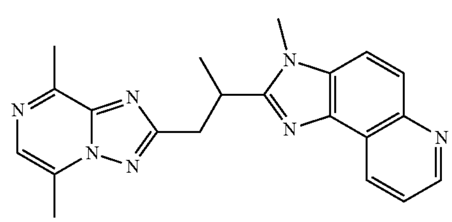 [SMILES: Cc1ncc(C)n2nc(CC(C)c3nc4c5cccnc5ccc4n3C)nc12] | J, X | LC-MS: m/z 372.1 (MH+) @ 1.36 min; ¹H NMR (CDCl₃, 400 MHz): δ 8.96 (dd, J = 8.0, 1.2 Hz, 1H), 8.86 (dd, J = 4.0, 1.6 Hz, 1H), 7.92 (d, J = 8.8 Hz, 1H), 7.78 (s, 1H), 7.68 (d, J = 9.2 Hz, 1H), 7.49 (dd, J = 8.0, 4.0 Hz, 1H), 4.00 (sxt, J = 7.2 Hz, 1H), 3.96 (s, 3H), 3.80 (dd, J = 15.2, 7.2 Hz, 1H), 3.51 (dd, J = 14.8, 6.8 Hz, 1H), 2.83 (s, 3H), 2.62 (s, 3H), 1.57 (d, J = 7.2 Hz, 3H). |

| Compound No. | Structure | Methods of Preparation | Analytical Data |
|---|---|---|---|
| 31 | 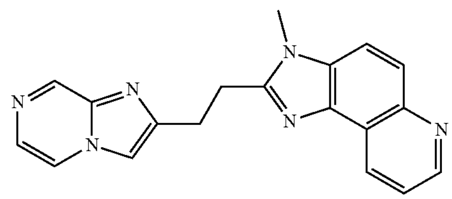 [SMILES: Cn1c(CCc2cn3ccncc3n2)nc2c3cccnc3ccc21] | C, K | LC-MS: m/z 329.1 (MH+) @ 1.22 min; 1H NMR (CDCl3, 400 MHz): δ 8.96 (dd, J = 4.8, 1.2 Hz, 1H), 8.91 (s, 1H), 8.81 (dd, J = 4.4, 1.6 Hz, 1H), 8.42 (dd, J = 4.4, 1.2 Hz, 1H), 7.95-7.85 (m, 3H), 7.83 (d, J = 4.4 Hz, 1H), 7.63 (dd, J = 8.4, 4.4 Hz, 1H), 3.91 (s, 3H), 3.55-3.45 (m, 4H). |
| 32 | 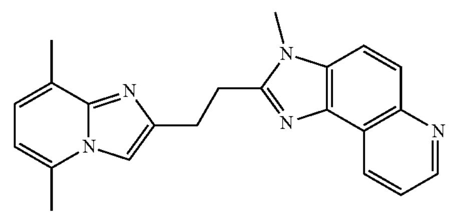 [SMILES: Cc1ccc(C)n2cc(CCc3nc4c5cccnc5ccc4n3C)nc12] | C, K | LC-MS: m/z 356.1 (MH+) @ 1.44 min; 1H NMR (CDCl3, 400 MHz): δ 8.97 (dd, J = 8.4, 1.2 Hz, 1H), 8.90 (dd, J = 8.0, 1.6 Hz, 1H), 7.94 (d, J = 9.2 Hz, 1H), 7.65 (d, J = 8.8 Hz, 1H), 7.53 (dd, J = 8.4, 4.4 Hz, 1H), 7.24 (s, 1H), 6.93 (d, J = 7.2 Hz, 1H), 6.49 (d, J = 6.8 Hz, 1H), 3.80 (s, 3H), 3.55-3.44 (m, 4H), 2.61 (s, 3H), 2.51 (s, 3H). |
| 33 | 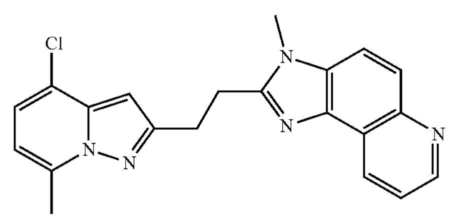 [SMILES: Cc1ccc(Cl)c2cc(CCc3nc4c5cccnc5ccc4n3C)nn12] | A, K | LC-MS: m/z 376.1 (MH+) @ 1.81 min; 1H NMR (CDCl3, 400 MHz): δ 8.97 (dd, J = 8.4, 0.8 Hz, 1H), 8.90 (dd, J = 8.0, 1.6 Hz, 1H), 7.96 (d, J = 8.8 Hz, 1H), 7.69 (d, J = 8.8 Hz, 1H), 7.53 (dd, J = 8.4, 4.4 Hz, 1H), 7.07 (d, J = 7.2 Hz, 1H), 6.54 (s, 1H), 6.51 (dd, J = 7.2, 0.8 Hz, 1H), 3.84 (s, 3H), 3.55-3.46 (m, 4H), 2.69 (s, 3H). |
| 34 | 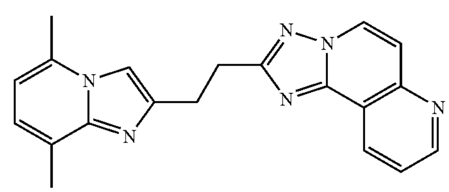 [SMILES: Cc1ccc(C)n2cc(CCc3nc4c5cccnc5ccn4n3)nc12] | C, M | LC-MS: m/z 343.1 (MH+) @ 1.13 min; 1H NMR (CDCl3, 400 MHz): δ 9.04 (dd, J = 4.4, 1.6 Hz, 1H), 8.90 (dd, J = 8.0, 1.6 Hz, 1H), 8.50 (d, J = 7.6 Hz, 1H), 7.63 (dd, J = 7.6, 4.4 Hz, 1H), 7.50 (d, J = 7.6 Hz, 1H), 7.32 (s, 1H), 6.94 (brs, 1H), 6.53 (brs, 1H), 3.55-3.45 (m, 4H), 2.62 (s, 3H), 2.50 (s, 3H). |
| 35 | 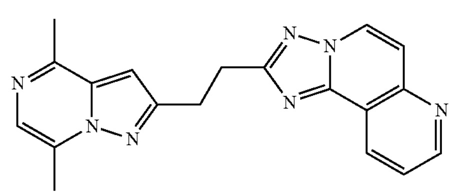 [SMILES: Cc1ncc(C)n2nc(CCc3nc4c5cccnc5ccn4n3)cc12] | A, M | LC-MS: m/z 344.2 (MH+) @ 1.40 min; 1H NMR (CDCl3, 400 MHz): δ 9.05 (dd, J = 8.4, 1.6 Hz, 1H), 8.90 (dd, J = 8.0, 1.6 Hz, 1H), 8.50 (d, J = 7.6 Hz, 1H), 7.63 (dd, J = 8.0, 4.8 Hz, 1H), 7.55 (brs, 1H), 7.51 (d, J = 7.2 Hz, 1H), 6.65 (s, 1H), 3.58-3.45 (m, 4H), 2.69 (s, 3H), 2.62 (s, 3H). |
| 36 | 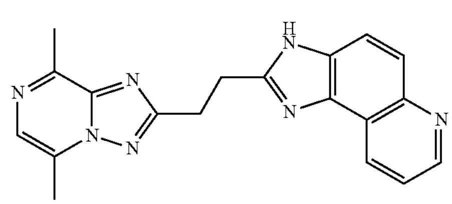 [SMILES: Cc1ncc(C)n2nc(CCc3nc4c(ccc5ncccc54)[nH]3)nc12] | J, K | LC-MS: m/z 344.2 (MH+) @ 1.18 min; 1H NMR (CD3OD), 400 MHz): δ 8.75 (m, 2H), 7.83 (d, J = 8.4 Hz, 1H), 7.82-7.72 (m, 2H), 7.55 (d, J = 4.4 Hz, 1H), 3.56 (brs, 4H), 2.73 (s, 3H), 2.58 (s, 3H). |

| Compound No. | Structure | Methods of Preparation | Analytical Data |
|---|---|---|---|
| 37 | 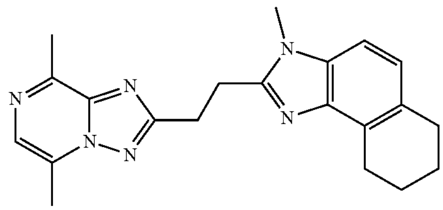 [SMILES: Cc1ncc(C)n2nc(CCc3nc4c5c(ccc4n3C)CCCC5)nc12] | J, U | LC-MS: m/z 361.2 (MH$^+$) @ 1.35 min; $^1$H NMR (CDCl$_3$, 400 MHz): δ 7.82 (s, 1H), 7.00 (ABq, J$_{AB}$ = 8.4 Hz, V$_{AB}$ = 29.6 Hz, 2H), 3.78 (s, 3H), 3.61-3.55 (m, 2H), 3.53-3.48 (m, 2H), 3.14 (apt, J = 6.0 Hz, 2H), 2.88-2.68 (m, 5H), 2.68 (s, 3H), 1.92-1.83 (m, 4H). |
| 38 | 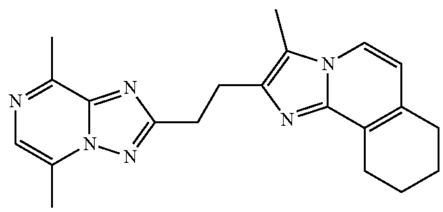 [SMILES: Cc1ncc(C)n2nc(CCc3nc4c5c(ccn4c3C)CCCC5)nc12] | J, W | LC-MS: m/z 361.1 (MH$^+$) @ 2.08 min; $^1$H NMR (CDCl$_3$, 400 MHz): δ 7.80 (s, 1H), 7.54 (d, J = 6.8 Hz, 1H), 6.52 (d, J = 6.8 Hz, 1H), 3.48-3.43 (m, 2H), 3.39-3.34 (m, 2H), 3.04 (apt, J = 5.6 Hz, 2H), 2.88 (d, J = 0.8 Hz, 3H), 2.72 (apt, J = 5.6 Hz, 2H), 2.69 (s, 3H), 2.35 (s, 3H), 1.89-1.84 (m, 4H). |
| 39 | 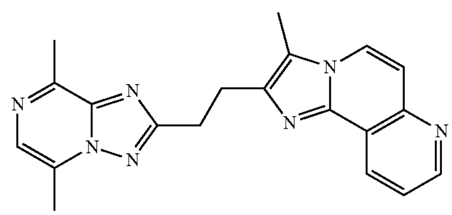 [SMILES: Cc1ncc(C)n2nc(CCc3nc4c5cccnc5ccn4c3C)nc12] | J, Z | LC-MS: m/z 358.1 (MH$^+$) @ 1.35 min; $^1$H NMR (CDCl$_3$, 400 MHz): δ 8.95-8.85 (m, 1H), 8.86 (d, J = 3.2 Hz, 1H), 7.88 (d, J = 8.4 Hz, 1H), 7.82 (s, 1H), 7.52 (dd, J = 7.6, 5.2 Hz, 1H), 7.32 (d, J = 6.8 Hz, 1H), 3.56-3.49 (m, 2H), 3.48-3.39 (m, 2H), 2.89 (s, 3H), 2.71 (s, 3H), 2.48 (s, 3H). |
| 40 | 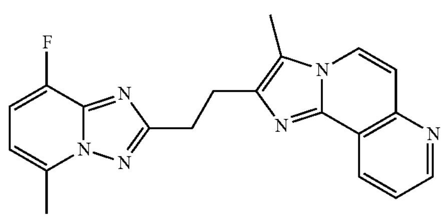 [SMILES: Cc1c(CCc2nc3c(F)ccc(C)n3n2)nc2c3cccnc3ccn12] | D, Z | LC-MS: m/z 361.1 (MH$^+$) @ 1.42 min; $^1$H NMR (CDCl$_3$, 400 MHz): δ 8.89 (d, J = 8.0 Hz, 1H), 8.85 (dd, J = 4.4, 1.6 Hz, 1H), 7.88 (d, J = 7.6 Hz, 1H), 7.52 (dd, J = 7.6, 4.4 Hz, 1H), 7.31 (d, J = 7.2 Hz, 1H), 7.14 (dd, J = 9.6, 8.0 Hz, 1H), 6.69 (dd, J = 7.6, 4.4 Hz, 1H), 3.52-3.46 (m, 2H), 3.45-3.39 (m, 2H), 2.72 (s, 3H), 2.47 (s, 3H). |
| 41 | 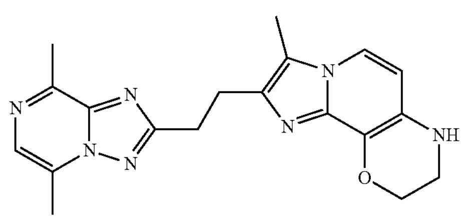 [SMILES: Cc1ncc(C)n2nc(CCc3nc4c5c(ccn4c3C)NCCO5)nc12] | J, V | LC-MS: m/z 364.1 (MH$^+$) @ 1.28 min; $^1$H NMR (CDCl$_3$, 400 MHz): δ 7.88 (s, 1H), 7.60 (d, J = 7.6 Hz, 1H), 6.76 (d, J = 7.2 Hz, 1H), 4.35 (t, J = 4.4 Hz, 2H), 3.58 (t, J = 4.4 Hz, 2H), 3.38-3.28 (m, 4H), 2.79 (s, 3H), 2.68 (s, 3H), 2.33 (s, 3H). |
| 42 | 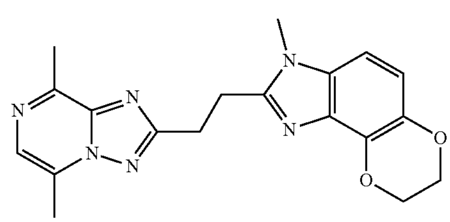 [SMILES: Cc1ncc(C)n2nc(CCc3nc4c5c(ccc4n3C)OCCO5)nc12] | J, T | LC-MS: m/z 365.1 (MH$^+$) @ 1.70 min; $^1$H NMR (CDCl$_3$, 400 MHz): δ 7.82 (d, J = 1.2 Hz, 1H), 6.79 (ABq, J$_{AB}$ = 8.4 Hz, V$_{AB}$ = 29.2 Hz, 2H), 4.44-4.41 (m, 2H), 4.32-4.29 (m, 2H), 3.75 (s, 3H), 3.69-3.63 (m, 2H), 3.47-3.41 (m, 2H), 2.89 (s, 3H), 2.69 (s, 3H). |

C. In Vitro Pharmacology

In one embodiment, the compounds provided herein were assayed for their ability to inhibit human PDE-10A. In one embodiment, the activities of the compounds were determined using the Molecular Devices IMAP PDE Fluorescence Polarization assay using recombinant human PDE-10 enzyme expressed in a baculoviral system. Briefly, 10 μL of a compound (0.2 nM-20 μM) was added to either a 96-well half area black plate or a 384-well black plate along with 10 μL of Fluorescein-labeled cAMP/cGMP substrate as per manufacturer's instructions and 10 μL of PDE enzyme (activity 0.1 U). Following a 40-minute incubation at 37° C., 60 μL of IMAP binding reagent was added. The plate was then read on a Perkin Elmer Victor (480-535 nm). The data was analyzed using Prism Software (GraphPad Inc, San Diego, Calif.).

The potency of the compounds provided herein in human PDE-10 inhibition assay (enzyme assay $IC_{50}$) is summarized in the table below.

| Compound No. | PDE-10 $IC_{50}$ (µM) |
|---|---|
| 1 | +++ |
| 2 | + |
| 3 | + |
| 4 | ++ |
| 5 | +++ |
| 6 | ++++ |
| 7 | ++++ |
| 8 | ++++ |
| 9 | ++++ |
| 10 | +++ |
| 11 | ++++ |
| 12 | ++ |
| 13 | +++ |
| 14 | +++ |
| 15 | + |
| 16 | ++++ |
| 17 | +++ |
| 18 | ++++ |
| 19 | ++++ |
| 20 | ++ |
| 21 | ++ |
| 22 | + |
| 23 | + |
| 24 | ++++ |
| 25 | +++ |
| 26 | + |
| 27 | +++ |
| 28 | +++ |
| 29 | ++++ |
| 30 | +++ |
| 31 | + |
| 32 | +++ |
| 33 | ++++ |
| 34 | ++ |
| 35 | +++ |
| 36 | ++++ |
| 37 | ++++ |
| 38 | ++++ |
| 39 | ++++ |
| 40 | ++++ |
| 41 | +++ |
| 42 | ++++ |

$IC_{50} \leq 0.01$ µM ++++;
$0.01 < IC_{50} \leq 0.1$ µM +++;
$0.1 < IC_{50} \leq 0.5$ µM ++;
$IC_{50} > 0.5$ µM +.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein by reference in their entireties. Citation or identification of any reference in this application is not an admission that such reference is available as prior art to this application. The full scope of the disclosure is better understood with reference to the appended claims.

What is claimed:

1. A compound of formula (I):

A-L-B (I)

or a pharmaceutically acceptable salt or stereoisomer thereof, wherein:

A is

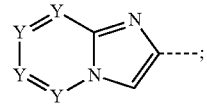

each Y is independently $CR^3$;
each $R^3$ is independently hydrogen, halogen, cyano, alkyl, trifluoromethyl, aminoalkyl, heteroalkyl, alkenyl, amido, amino, alkoxy, thiol, cycloalkyl, aryl, heterocyclyl, or heteroaryl;

B is

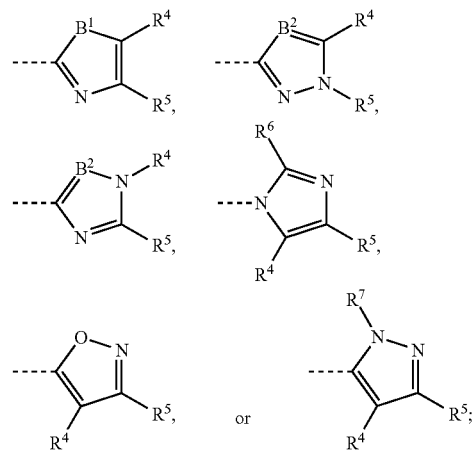

$B^1$ is $NR^8$, O, or S;
$B^2$ is $CR^9$ or N;
L is —$C(R^{10})_2$—$C(R^{10})_2$—;
$R^4$ and $R^5$, together with the atoms to which they are attached, form a cycloalkyl ring, a monocyclic aryl ring, a multicyclic aryl ring, a heterocyclyl ring, or a heteroaryl ring, each of which is substituted with one or more $R^{12}$;
$R^6$ is hydrogen, halogen, cyano, alkyl, aminoalkyl, heteroalkyl, aralkyl, heteroaralkyl, alkenyl, amido, amino, alkoxy, thiol, cycloalkyl, aryl, heterocyclyl, or heteroaryl;
$R^7$ is hydrogen, alkyl, heteroalkyl, alkenyl, cycloalkyl, aryl, heterocyclyl, or heteroaryl;
$R^8$ is hydrogen, alkyl, heteroalkyl, alkenyl, cycloalkyl, aryl, heterocyclyl, or heteroaryl;
$R^9$ is hydrogen, halogen, cyano, alkyl, aminoalkyl, heteroalkyl, aralkyl, heteroaralkyl, alkenyl, amido, amino, alkoxy, thiol, cycloalkyl, aryl, heterocyclyl, or heteroaryl;
each $R^{10}$ is independently hydrogen;
each occurrence of $R^{12}$ is independently (i) hydrogen, halogen, cyano, $C(O)R^{13}$, $C(O)NR^{13}R^{14}$, $C(O)OR^{13}$, $NR^{13}R^{14}$, $N(R^{13})C(O)R^{14}$, $OR^{13}$, $OC(O)R^{13}$, $SR^{13}$, $S(O)R^{13}$, $S(O)_2R^{13}$, or $S(O)_2NR^{13}R^{14}$; or (ii) alkyl, heteroalkyl, aralkyl, heteroaralkyl, cycloalkyl, aryl, heterocyclyl, or heteroaryl; and
each occurrence of $R^{13}$ and $R^{14}$ is independently hydrogen, alkyl, heteroalkyl, aralkyl, heteroaralkyl, cycloakyl, aryl, heterocyclyl, or heteroaryl; or $R^{13}$ and $R^{14}$, together with the nitrogen atom to which they are attached, may form a 3 to 10 membered ring.

2. The compound of claim 1, or a pharmaceutically acceptable salt or stereoisomer thereof, wherein each $R^3$ is independently hydrogen, methyl, ethyl, or trifluoromethyl.

3. The compound of claim 1, or a pharmaceutically acceptable salt or stereoisomer thereof, wherein B is:

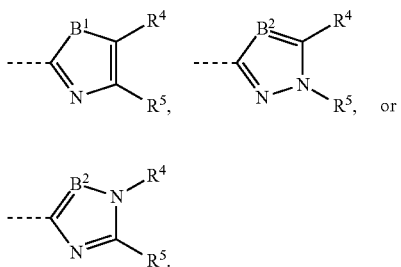

4. The compound of claim 3, or a pharmaceutically acceptable salt or stereoisomer thereof, wherein:
   $R^4$ and $R^5$, together with the atoms to which they are attached, form a multicyclic aryl ring; and
   B is a bicyclic ring system.

5. The compound of claim 3, or a pharmaceutically acceptable salt or stereoisomer thereof, wherein:
   $R^4$ and $R^5$, together with the atoms to which they are attached, form a multicyclic aryl ring; and
   B is a tricyclic ring system.

6. The compound of claim 5, or a pharmaceutically acceptable salt or stereoisomer thereof, wherein B is:

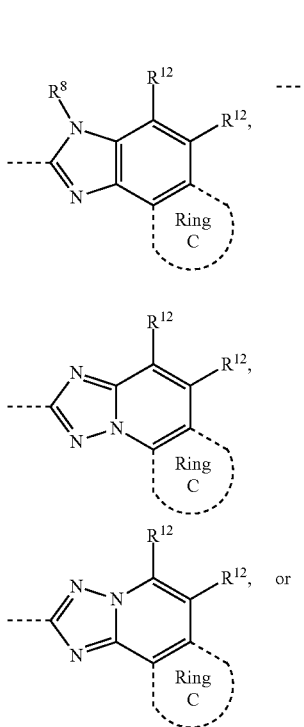

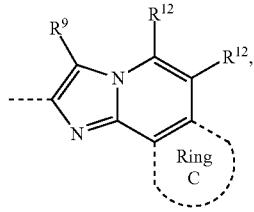

wherein:
   Ring C is a 5- to 7-membered cycloalkyl ring, a 5- to 7-membered heterocyclyl ring, or a 5- or 6-membered heteroaryl ring.

7. The compound of claim 6, or a pharmaceutically acceptable salt or stereoisomer thereof, wherein:
   $R^8$ is hydrogen or methyl; and
   $R^9$ is hydrogen or methyl.

8. The compound of claim 6, or a pharmaceutically acceptable salt or stereoisomer thereof, wherein each occurrence of $R^{12}$ is independently hydrogen.

9. The compound of claim 1, wherein the compound is:

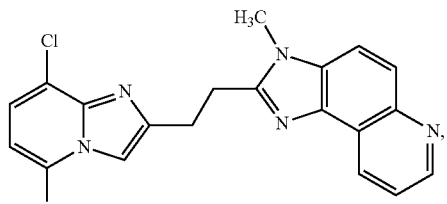

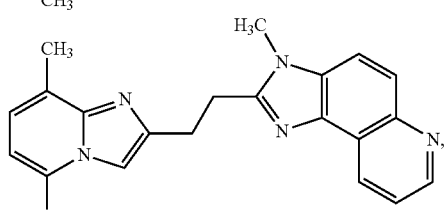

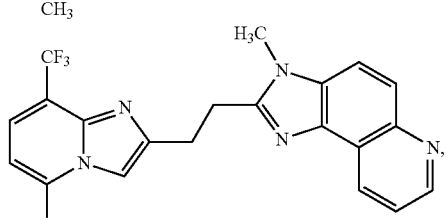

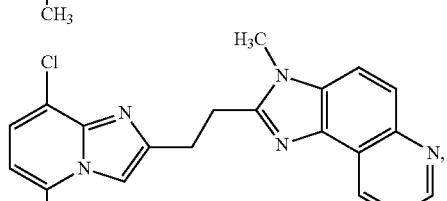

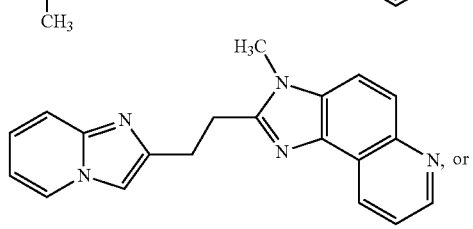

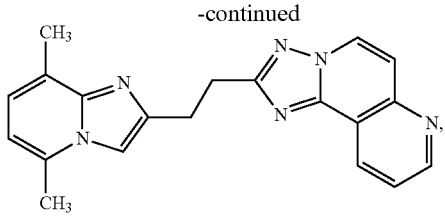

or a pharmaceutically acceptable salt or stereoisomer thereof.

10. A pharmaceutical composition comprising a compound of claim 1, or a pharmaceutically acceptable salt or stereoisomer thereof, and at least one pharmaceutically acceptable excipient, diluent, or carrier.

11. The pharmaceutical composition of claim 10, wherein the pharmaceutical composition further comprises one or more additional active agents.

12. A method for inhibiting phosphodiesterase-10A activity in a subject, comprising administering to a subject in need thereof a therapeutically or prophylactically effective amount of a compound of claim 1, or a pharmaceutically acceptable salt or stereoisomer thereof.

13. The method of claim 12, wherein the subject suffers from a neurological disorder, a schizophrenia-related disorder, a disease having a psychosis component, a psychotic disorder, a behavior disorder, a neurodegenerative disease, a mood disorder, a manic disorder, a movement disorder, a sleep disorder, an addiction, or an eating disorder.

14. The method of claim 13, wherein the subject suffers from schizophrenia, psychosis, Huntington's disease, depression, or cognitive impairment.

15. The method of claim 12, wherein the subject suffers from schizophrenia, schizophrenia spectrum disorder, schizoaffective disorder, schizophreniform disorder, paraphrenia, paranoid personality disorder, schizoid personality disorder, schizotypal personality disorder, delusional disorder, psychosis, psychoaffective disorder, aggression, delirium, Tourette's syndrome, convulsion, seizure, agitation, posttraumatic stress disorder, Huntington's disease, Alzheimer's disease, Parkinson's disease, dyskinesia, dementia, bipolar disorder, anxiety, depression, major depressive disorder, dysthymia, affective disorder, obsessive-compulsive disorder, attention deficit disorder, attention deficit hyperactivity disorder, vertigo, pain, sensitization accompanying neuropathic pain, fibromyalgia, migraine, cognitive impairment, cognitive deficit in Alzheimer's disease, cognitive deficit in Parkinson's disease, restless leg syndrome, multiple sclerosis, substance abuse, substance dependency, autism, obesity, undesirable weight retention, undesirable weight gain, metabolic syndrome, diabetes, impaired glucose tolerance, or hyperglycemia.

16. The method of claim 12, wherein the subject suffers from acute schizophrenia, chronic schizophrenia, not otherwise specified schizophrenia, brief psychotic disorder, Alzheimer's psychosis, Parkinson's psychosis, shared psychotic disorder, substance-induced psychotic disorder, a psychotic disorder due to a general medical condition, excitative psychosis, organic psychosis, not otherwise specified psychosis, unipolar depression, treatment resistant depression, seasonal affective disorder, neuropathic pain, inflammatory pain, cognitive impairment associated with schizophrenia, or non-insulin dependent diabetes.

17. The method of claim 12, wherein the method further comprises administering to the subject in need thereof a therapeutically or prophylactically effective amount of a second active agent.

18. A method for inhibiting phosphodiesterase-10A activity in a subject, comprising administering to a subject in need thereof a therapeutically or prophylactically effective amount of a compound of claim 9, or a pharmaceutically acceptable salt or stereoisomer thereof.

* * * * *